US008237013B2

(12) United States Patent
Nielsen et al.

(10) Patent No.: US 8,237,013 B2
(45) Date of Patent: Aug. 7, 2012

(54) MEANS AND METHODS FOR CONTROLLING FLOWERING IN PLANTS

(75) Inventors: Klaus K Nielsen, Copenhagen Nv (DK); Claus H. Andersen, Koege (DK); Marianne Folling, Roennede (DK); Caixa Gao, Solroed Strand (DK); Ingo Lenk, Roskilde (DK); Thomas Didion, Valby (DK); Christian Sig Jensen, Rigsted (DK); Klaus Petersen, Kbh V (DK); Morten Storgaard, Frederiksberg C (DK)

(73) Assignee: DLF-Trifolium A/S, Store Heddinge (DK)

( * ) Notice: Subject to any disclaimer, the term of this patent is extended or adjusted under 35 U.S.C. 154(b) by 1463 days.

(21) Appl. No.: 11/571,656

(22) PCT Filed: Jul. 7, 2005

(86) PCT No.: PCT/EP2005/007367
§ 371 (c)(1),
(2), (4) Date: May 4, 2007

(87) PCT Pub. No.: WO2006/005520
PCT Pub. Date: Jan. 19, 2006

(65) Prior Publication Data
US 2011/0131682 A1 Jun. 2, 2011

Related U.S. Application Data

(60) Provisional application No. 60/586,062, filed on Jul. 8, 2004.

(51) Int. Cl.
*C12N 15/29* (2006.01)
*C12N 15/82* (2006.01)
*C12N 15/87* (2006.01)
*C12N 5/04* (2006.01)
*A01H 5/00* (2006.01)

(52) U.S. Cl. ...... 800/278; 800/298; 536/23.1; 536/23.6; 435/410; 435/320.1; 435/419

(58) Field of Classification Search .................. None
See application file for complete search history.

(56) References Cited

U.S. PATENT DOCUMENTS
7,888,122 B2 * 2/2011 Amasino et al. ............. 435/468

FOREIGN PATENT DOCUMENTS

| WO | WO-93/21334 | 10/1993 |
|---|---|---|
| WO | WO-97/10339 | 3/1997 |
| WO | WO-99/53070 | 10/1999 |
| WO | WO-01/09357 | 2/2001 |
| WO | WO-02/14524 | 2/2002 |
| WO | WO-02/44390 | 6/2002 |
| WO | WO 02/44390 A2 * | 6/2002 |
| WO | WO-03/076612 | 9/2003 |
| WO | WO-2004/022755 | 3/2004 |
| WO | WO-2004/101791 | 11/2004 |
| WO | WO-2004/101792 | 11/2004 |

OTHER PUBLICATIONS

Bohlenius et al (2006, Science 312:1040-1043).*
Bowie et al, Science 247:1306-1310.*
McConnell et al, Nature 411 (6838):709-713, 2001.*
Fourgoux-Nicol et al (1999, Plant Molecular Biology 40 :857-872).*
Ahn, J.H. et al.,"A putative external loop domain in the 4th exon determines functional specificity of FT and TFL1," International Conference on Arabidopsis Research, Wisconsin, Madison, 2001.
Storgaard Morten et al., "Expression of a 434:VP16 chimeric activator leads to high-level activation of gene expression in stable transformants of Arabidopsis," Transgenic Research, vol. 11, No. 2, Apr. 2002, pp. 151-159.
Kardailsky I et al., "Activation tagging of the floral inducer FT," Science, American Association for the Advancement of Science, US, vol. 286, No. 5446, Dec. 3, 1999, pp. 1962-1965.
Jesen Chrisitian S et al., "Floral inhibition in red Fescue (Festuca Rubra L.) through expression of a heterologous flowering repressor from Lolium." Molecular Breeding, vol. 13, No. 1, Jan. 2004, pp. 37-78.
Pnueli, L. et al., "The Self-Pruning gene of tomato regulates vegetative to reproductive switching of sympodial meristems and is the ortholog of CEN and TFL1", Development, 1998, vol. 125, pp. 1979-1989.
Carmel-Goren, Lea et al., "The Self-Pruning gene family in tomato", Plant Molecular Biology, 2003, vol. 52, pp. 1215-1222.
EMBL Accession No. ADU71339, Kardailsky et al., Feb. 10, 2005.
EMBL Accession No. ADU87259, Kardailsky et al., Feb. 10, 2005.
Ahn, Ji Hoon et al., "A divergent external loop confers antagonistic activity on floral regulators FT and TFL1", The EMBO Journal, 2006, vol. 25, pp. 605-614.

* cited by examiner

*Primary Examiner* — Stuart F. Baum
(74) *Attorney, Agent, or Firm* — Birch, Stewart, Kolasch & Birch, LLP

(57) ABSTRACT

Described are means and methods for controlling flowering in plants. In particular, described are nucleic acid molecules which, when expressed in sense orientation or in antisense orientation, respectively, in plants lead to a prevention of flowering. Moreover, a method for controlling flowering in plants is provided which comprises the inducible restoration of flowering in plants in which flowering is prevented.

16 Claims, 22 Drawing Sheets

Figure 1:
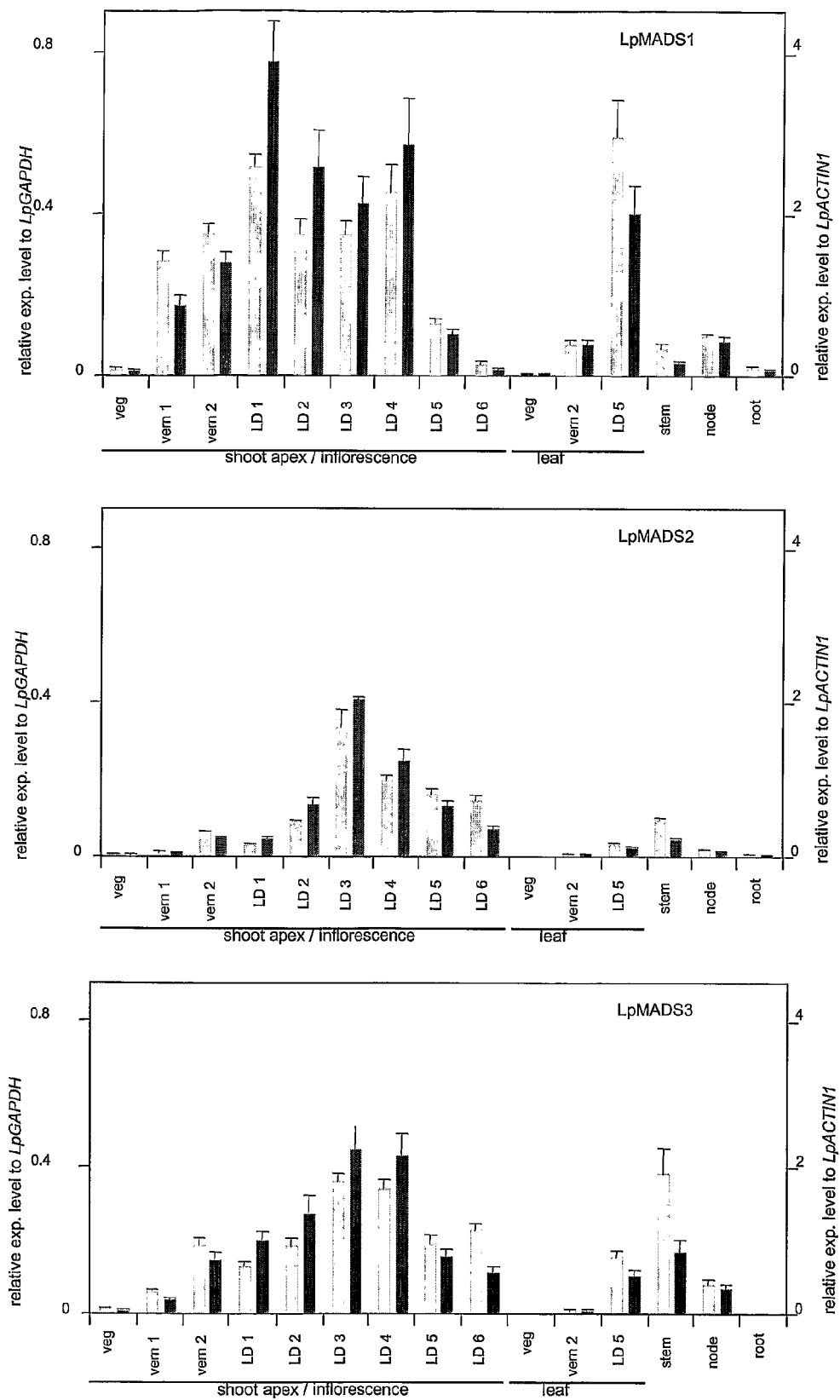

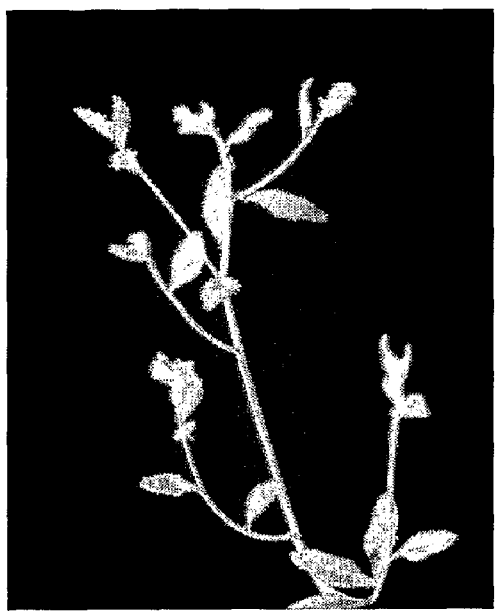
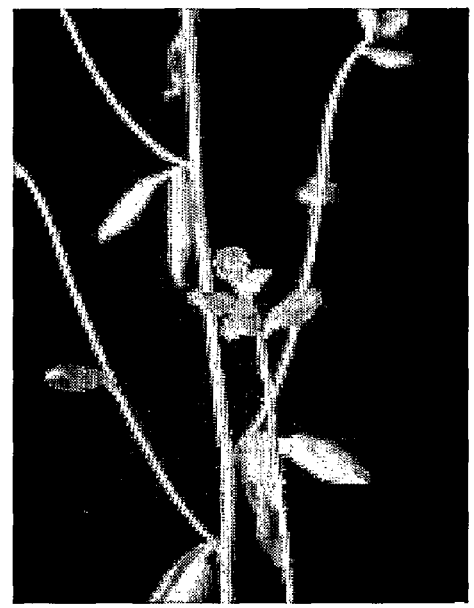
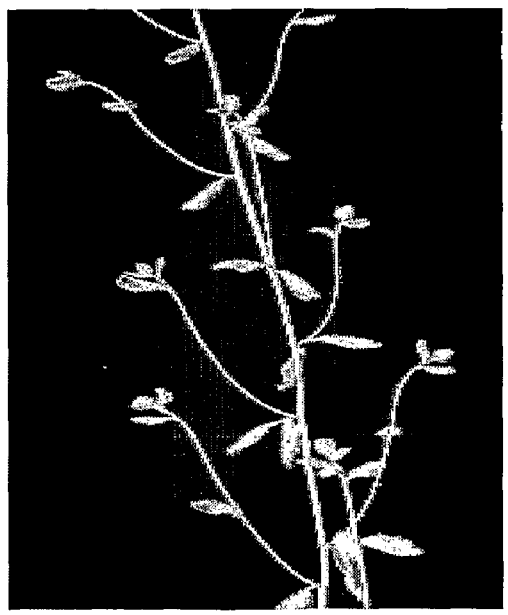
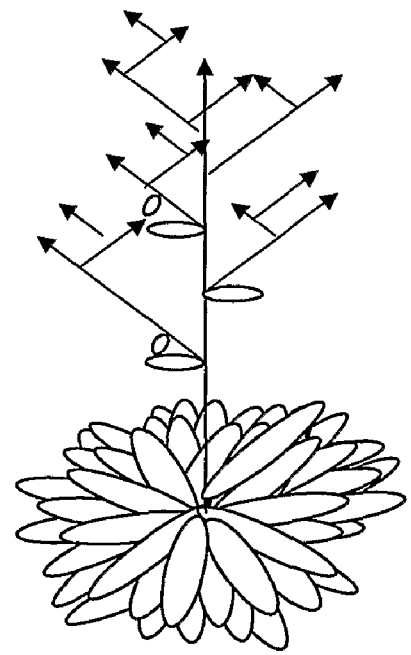
Figure 4

LpTFL1 + LpFT-like    LpTFL    Col

◄─────────────────────────
Flowering time

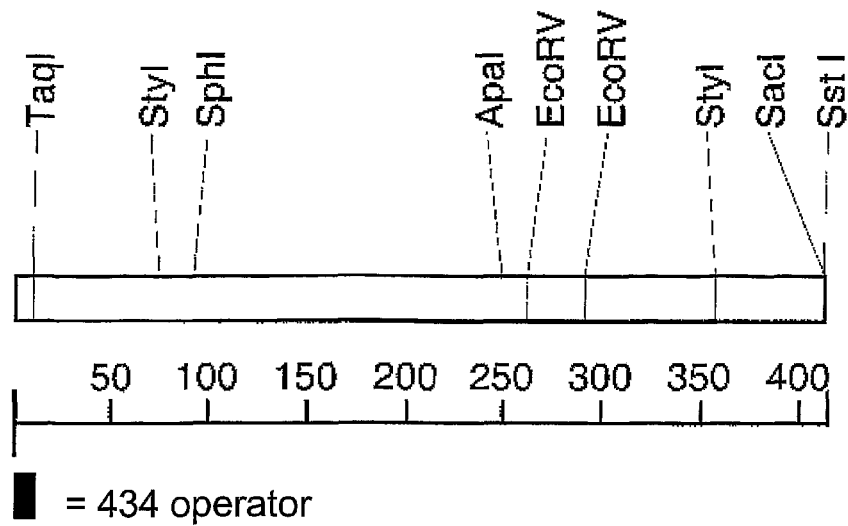

■ = 434 operator alcA promoter sequence with the two 434 O$_R$2 operator sequences (bold and underlined)

```
CTGCTGATTGTCGATAGTTGTGATAGTTCCCACTTGTCCGTCCGCATCGGCATCCGCAGCTCSGGATAGT
TCCGACCTAG
GATTGGATGCATGCGGAACCGCACGAGGGCGGGGCGGAAATTGACACACCACTCCTCTCCACGCACCGTT
CAAGAGGTAC
GCGTATAGAGCCGTATAGAGCAGAGACGGAGCACTTTCTGGTACTGTCCGCACGGGATGTCCGCACGGAG
AGCCACAAWC
GAGCGGGGCCCCGTAACAAGATATCTTGTTTGAAGATAGAAAATAACAAGATATCTTGTCGTGCTCTCCT
ACCCCAGGAT
CGCATCCCCGCATAGCTGAACATCTATATAAAGACCCCCAAGGTTCTCAGTCTCACCAACATCATCAACC
AACAATCAAC
AGTTCTCTGAGCTC    (SEQ ID No: 74)
```

Figure 15

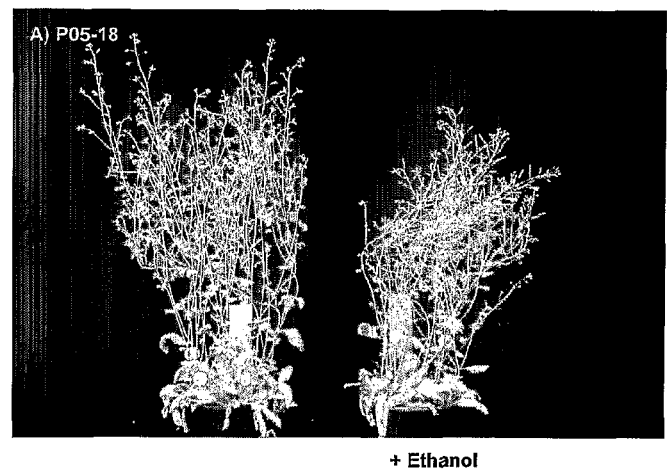
+ Ethanol
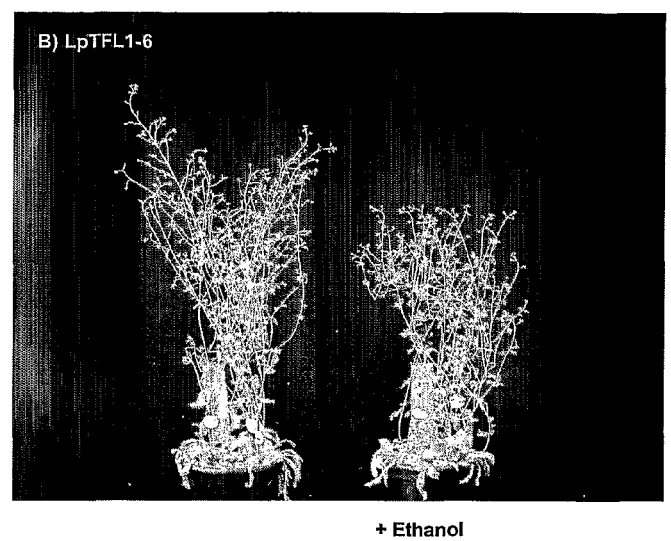
+ Ethanol
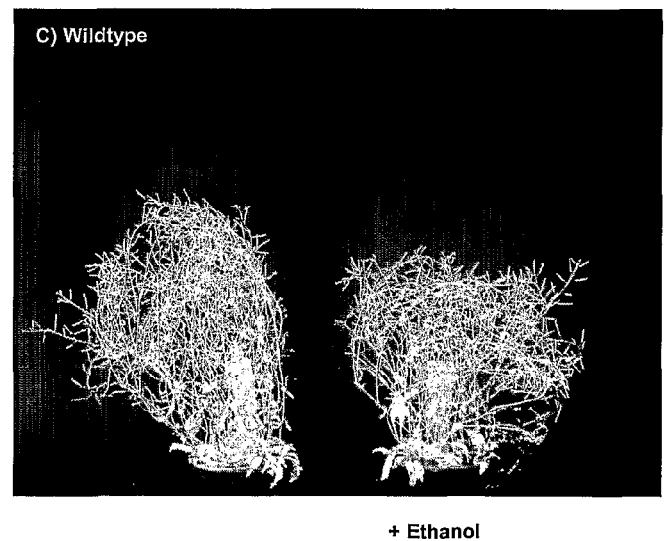
+ Ethanol
Figure 17

MEANS AND METHODS FOR CONTROLLING FLOWERING IN PLANTS

The present invention relates to nucleic acid molecules involved in the control of flowering in plants as well as to methods for controlling flowering in plants.

It is known that the production of culm (stem) and seed head (inflorescence) formation may decrease the feeding value of various kinds of fodder plants such as forage grasses. In forage grasses the leaf blades are more digestible, richer in crude protein and poorer in cell-wall constituents than sheaths and culms (Deinum and Dirvan, Neth. J. Agri. Sci. 23 (1975) 69-82; Wilman et al., J. Br. Grassl. Soc. 31 (1976), 73-79). The ageing of grasses (development towards flowering and seed setting) is associated with an increase in lignification and a decrease in digestibility, which is markedly higher for the stems than for the leaves (Delagarde et al., Anim. Feed. Sci. Technol. 84 (2000), 49-68). In consequence, the digestibility of grasses becomes markedly reduced during the course of the growth season. This reduction is largely caused by an increase in the content of poorly digestible cell wall structural components, mainly lignins. In parallel, there is a decrease in content of soluble carbohydrates. Poorly digestible structural components create an imbalance between carbohydrate and protein levels during ruminant fermentation, leading to a loss of nitrogen (ammonia) to the environment. Grass varieties with an increased level of soluble carbohydrates and increased digestibility will lead to a more efficient uptake of proteins in ruminants and, thus, an enhanced milk and meat production. Feeding trials on cows have documented that increasing the digestibility of forage grass is directly associated with a daily increase in feed uptake and milk production (Oba and Allen, J. Dairy Sci. 82 (1999), 589-596). Secondly, flowering in many plants is associated with an uncontrollable gene flow from cultivated to wild relatives via the active spread of pollen. Systems to control flowering will provide a means to avoid spread of pollen, e.g. in the grass field, and thus provide systems for biological containment of transgenes. Thirdly, flowering in many perennial plants is also associated with an exposure to pollen allergens, such as grass pollen allergens. A cultivar, in particular a grass cultivar, with an extended vegetative growth associated with decreased or even eliminated inflorescence production would thus be attractive to agriculture and society.

It would be desirable to have methods of controlling plant life cycles and growth phases, e.g. the transition from the vegetative to the reproductive stage, flowering processes, and inflorescence and flower development in plants, including dicots and monocots and in particular including grass species such as ryegrasses (*Lolium* species) and fescues (*Festuca* species). This would facilitate the production of, for example, pasture and turf grasses with enhanced or shortened or modified life cycles, enhanced or reduced or otherwise modified inflorescence and flower development, male and female sterility, inhibited flowering (e.g. non-flowering), modified flowering architecture (e.g. indeterminate and determinate), earlier or delayed flowering, enhanced or modified number of leaves, enhanced or reduced or otherwise modified number of reproductive shoots, enhanced persistence and improved herbage quality, enhanced seed and leaf yield, altered growth and development, leading to improved seed production, improved biomass production, improved pasture production, and improved pasture quality.

The life cycle of flowering plants in general can be divided into three growth phases: vegetative, inflorescence, and floral (Poethig, Science 250 (1990), 923-930). In the vegetative phase, the shoot apical meristem (SAM) generates leaves that will later ensure the resources necessary to produce fertile offspring. Upon receiving the appropriate environmental and developmental signals, the plant switches to floral, or reproductive, growth and the SAM enters the inflorescence phase ($I_1$) and gives rise to an inflorescence with flower primordia. During this phase, the fate of the SAM and the secondary shoots that arise in the axils of the leaves is determined by a set of meristem identity genes, some of which prevent and some of which promote the development of floral meristems.

The regulation of meristem identity and floral transition has been investigated in a number of dicotyledonous plants including *Arabidopsis, Antirrhinum*, tomato, and tobacco. However, in agronomically important seed crops such as wheat, barley, rice, forage grasses, and other monocotyledonous plants, information on the genetic regulation of floral transition is still limited.

Perennial ryegrass will not flower unless it receives a vernalisation period. This cold treatment is required to alleviate a natural flowering "roadblock" that ensures that flowering occurs in the spring. In growth chamber conditions, flowering in perennial ryegrass is induced by a vernalization period of 12 to 14 weeks below 5° C. followed by secondary induction with long-day photoperiods (generally, more daylight hours than dark hours and, more specifically, LD, 16 hours of light, 8 hours of darkness) and temperatures above 15 to 20° C.

The TERMINAL FLOWER 1 (TFL1) gene from *Arabidopsis thaliana* has been identified to specify an indeterminate identity of inflorescence meristems. Mutations in TFL1 result in the conversion of the inflorescence into a terminal flower (Shannon and Meeks-Wagner, Plant Cell 3 (1991), 877-892), and in addition, TFL1 has been found to extend the vegetative growth phase of *Arabidopsis* (Shanon and Meeks-Wagner, loc. cit.; Ratcliff et al., Development 126 (1998), 1109-1120). TFL1 proteins have sequence similarity with mammalian phosphatidylethanolamine-binding proteins (PEBPs).

Previously, *Arabidopsis thaliana*, red fescue (*Festuca rubra* L.), and perennial ryegrass (*Lolium perenne* L) were transformed with LpTFL1 and it was shown that overexpression of LpTFL1 results in a dramatic extension of the vegetative growth phase correlating to the level of gene expression with the highest expressing lines remaining non-flowering (Jensen et al., Plant Physiol. 125 (2001), 1517-1528; Jensen et al., Mol. Breeding 13 (2004), 37-48; P11792US-20030226). In addition, it was shown that LpTFL1 is capable of preventing flowering in red fescue and perennial ryegrass in subsequent years.

FLC/FLF represents a major floral inhibitor in *Arabidopsis* integrating several of the floral inductive pathways and was recently identified as a MADS box protein (Michaels and Amasino, Plant Cell 11 (1999), 949-956; Sheldon et al., Plant Cell 11 (1999), 445-458). The use of FLC/FLF to alter the flowering time/behavior in plants has been described in WO 00/50615 and WO 00/32780.

The INDETERMINATE1 (ID1) gene of maize controls the transition of flowering in this species by encoding a transcriptional regulator of the floral transition (Colasanti et al., Cell 93 (1998), 513-603). In this study, ID1 was identified by a mutation with the phenotype of dramatic reduction in the ability of maize to undergo the transition to reproductive growth. Homozygous id1 maize mutant plants produced many more leaves than did wild-type maize plants, and remained in a prolonged vegetative growth state. The use of the maize ID1 gene as a method for producing plants with altered time of floral transition has been suggested, but not demonstrated, in WO 96/34088. In WO 02/38768, a method of using ID1 homologues isolated from perennial ryegrass to modify plant life cycles and/or growth phases has been suggested, in which the use of 3 different polynucleotide sequences and their corresponding polypeptides isolated from perennial ryegrass is described. The described peptides belong to the group of Zink Finger proteins characterized by the presence of two conserved so called Zink Finger domains, as does the maize ID1.

The CONSTANS gene (CO) encodes a polypeptide belonging to the group of Zink Finger proteins and has been shown to represent the major regulator of the photoperiodic floral pathway in *Arabidopsis* (Putterill et al., Cell 80 (1995), 847-857). The use of CO to influence the flowering characteristics of plants has been described in WO 96/14414.

FT, The FLOWERING LOCUS T (FT) gene belongs to the family of plant PEBP genes as does TFL1, but has been shown to play a role opposite to TFL1 in mediating flower inducing signals in *Arabidopsis* (Kardailsky et al., Science 286 (1999), 1962-1965; Kobayashi et al., Science 286 (1999), 1960-1962). A method of modulating flowering time in a plant by the use of FT has been suggested in U.S. Pat. No. 6,225,530.

LEAFY (LFY) is a unique gene with little homology to other gene classes whereas APETALA1 (AP1) belongs to the MADS box family. Together they represent members of the group of 'meristem identity genes', specifying floral meristem identity (Weigel et al., Cell 69 (1992), 843-859; Mandel et al., Nature 360 (1992), 273-277). The use of LFY to control floral meristem development and enhance or delay flowering in a plant has been suggested in WO 96/19105 and U.S. Pat. No. 5,844,119. The use of AP1 to manipulate flowering time in a plant has been suggested in WO 97/46078 and U.S. Pat. No. 5,844,119. The use of MADS box proteins to manipulate flowering and plant architecture of *Lolium* or *Festuca* plant species has been suggested in WO 02/33091.

The technical problem underlying the present invention is the provision of means and methods allowing to control flowering in plants, preferably in forage grasses such as ryegrasses and fescues.

This technical problem is solved by the provision of the embodiments as characterized in the claims.

Accordingly, in a first aspect the present invention relates to polynucleotides which, when expressed in sense orientation in plants lead to a prevention of flowering, selected from the group consisting of
(a) polynucleotides comprising a nucleotide sequence encoding a polypeptide with the amino acid sequence of SEQ ID NO:2;
(b) polynucleotides comprising the coding region of the nucleotide sequence shown in SEQ ID NO:1;
(c) polynucleotides comprising a nucleotide sequence encoding a fragment of the polypeptide encoded by a polynucleotide of (a) or (b), wherein said nucleotide sequence when expressed in sense orientation in plants leads to a prevention of flowering;
(d) polynucleotides comprising a nucleotide sequence having a sequence identity of at least 50% with a polynucleotide of any one of (a) to (c) and which when expressed in sense orientation in plants leads to a prevention of flowering;
(e) polynucleotides comprising a nucleotide sequence the complementary strand of which hybridizes to the polynucleotide of any one of (a) to (c), wherein said nucleotide sequence when expressed in sense orientation in plants leads to a prevention of flowering; and
(f) polynucleotides comprising a nucleotide sequence that deviates from the nucleotide sequence defined in (e) by the degeneracy of the genetic code.

Thus, the present invention relates in a first aspect to a polynucleotide which when expressed in sense orientation in plants leads to a prevention of flowering. Preferably, such a polynucleotide comprises the coding region of the nucleotide sequence shown in SEQ ID NO:1 or encode a polypeptide comprising the amino acid sequence shown in SEQ ID NO:2.

The present invention is based on the identification of a gene from *Lolium perenne* which leads to a prevention of flowering in plants when expressed in sense orientation.

This gene, of which the cDNA sequence is shown in SEQ ID NO:1 and the derived amino acid sequence is shown in SEQ ID NO:2, will be referred to in the following as LpFT-like gene and protein, respectively. This gene was identified by PCR amplification based on a *Lolium perenne* cDNA library and by using primers based on known FT-like genes (see Example 1).

The present invention in particular relates to polynucleotides containing the nucleotide sequence indicated under SEQ ID NO:1, encoding the amino acid sequence shown under SEQ ID NO:2 or a part thereof which, when expressed in sense orientation in plants leads to a prevention of flowering.

The term "prevention of flowering" means the reduction, delay or complete inhibition of flowering. "Flowering" means the development of female and/or male floral and/or reproductive organs, such as floral meristems, inflorescences, spikelets, sepals, petals, carpels, stamens, embryos, pollen, seeds, etc. A reduction of flowering" means the lack of a complete set of the above-mentioned female and/or male floral and/or reproductive organs. The term "delay of flowering" means that flowering occurs at a later time point in comparison to wild-type, i.e. not genetically-modified, plants grown under the same conditions. A "later time point" preferably means at least 20 days later, more preferably 40 days later, even more preferably 60 days later, particularly preferred at least 100 days later, especially preferred at least 200 days later and most preferably at least 600 days later.

The term "complete inhibition of flowering" means that no organs or tissue associated with sexual reproduction are developed while the plant continues to produce vegetative tissues.

Moreover, the present invention relates to polynucleotides the complementary strand of which hybridizes with a polynucleotide mentioned in sections (a) to (c), above, and which when expressed in sense orientation in plants, lead to a prevention of flowering.

The present invention also relates to polynucleotides which encode a polypeptide, which has a homology, that is to say a sequence identity, of at least 60%, preferably of at least 70%, more preferably of at least 75%, even more preferably of at least 80% and particularly preferred of at least 85%, especially preferred of at least 90% and even more preferred of at least 95, 96, 97, 98 or 99% to the entire amino acid sequence indicated in SEQ ID NO: 2, the polypeptide leading to a prevention of flowering when expressed in a plant.

Moreover, the present invention relates to polynucleotides the nucleotide sequence of which has a homology, that is to say a sequence identity, of at least 50%, preferably of at least 60%, more preferably of at least 70%, even more preferably of more than 80%, in particular of at least 85%, especially preferred of at least 90%, in particular of at least 95% and even more preferred of at least 98% when compared to the coding region of the sequence shown in SEQ ID NO: 1, and which when expressed in sense orientation in plants, lead to a prevention of flowering.

The present invention also relates to polynucleotides the sequence of which deviates from the nucleotide sequences of the above-described polynucleotides due to the degeneracy of the genetic code.

The invention also relates to polynucleotides comprising a nucleotide sequence which is complementary to the whole or a part of one of the above-mentioned sequences.

In the context of the present invention the term "hybridization" means hybridization under conventional hybridization conditions, preferably under stringent conditions, as for instance described in Sambrook and Russell (2001), Molecular Cloning: A Laboratory Manual, CSH Press, Cold Spring Harbor, N.Y., USA. In an especially preferred embodiment, the term "hybridization" means that hybridization occurs under the following conditions:

Hybridization buffer: 2×SSC; 10×Denhardt solution (Fikoll 400+PEG+BSA; ratio 1:1:1); 0.1% SDS; 5 mM EDTA; 50 mM $Na_2HPO_4$;
  250 µg/ml of herring sperm DNA; 50 µg/ml of tRNA; or
  0.25 M of sodium phosphate buffer, pH 7.2;
  1 mM EDTA
  7% SDS
  Hybridization temperature T=60° C.
  Washing buffer: 2×SSC; 0.1% SDS
  Washing temperature T=60° C.

In another preferred embodiment, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched sequence (probe). Preferably, the Tm values of the sequences, i.e. the sequences according to the invention described above and the hybridizing sequences, are within 10° C. of each other if they are mixed together and denatured simultaneously. More preferably hybridization may be performed under stringent conditions, e.g., for a specified period of time at a temperature of between 50 and 70° C. in double strength SSC (2×NaCl 17.5 g/l and sodium citrate (SC) at 8.8 g/l) buffered saline containing 0.1% sodium dodecyl sulphate (SDS) followed by washing at the same temperature but with a buffer having a reduced SSC concentration. Depending upon the degree of stringency required, and thus the degree of similarity of the sequences, such reduced concentration buffers are typically single strength SSC containing 0.1% SDS, half strength SSC containing 0.1% SDS and one tenth strength SSC containing 0.1% SDS. In a preferred embodiment hybridization is carried out with one of the sequences being fixed to a support, e.g., a filter or Nylon membrane.

Sequences having the highest degree of similarity are those the hybridization of which is least affected by washing in buffers of reduced concentration. It is most preferred that the hybridizing sequences are so similar to the above described sequences according to the invention that the hybridization between them is substantially unaffected by washing or incubation at high stringency, for example, in one tenth strength sodium citrate buffer containing 0.1% SDS.

Polynucleotides which hybridize with the polynucleotides disclosed in connection with the invention can for instance be isolated from genomic libraries or cDNA libraries of plants, in particular from the family of Poaceae, preferably from a grass species such as from *Phleum* spp., *Dactylis* spp., *Lolium* spp., *Festulolium* spp., *Festuca* spp., *Poa* spp., *Bromus* spp., *Agrostis* spp., *Arrhenatherum* spp., *Phalaris* spp., *Brachypodium* ssp. and *Trisetum* spp., for example, *Phleum pratense, Phleum bertolonii, Dactylis glomerata, Lolium perenne, Lolium multiflorum, Lolium multiflorum westervoldicum, Festulolium braunii, Festulolium loliaceum, Festulolium holmbergii, Festulolium pabulare, Festuca pratensis, Festuca rubra, Festuca rubra rubra, Festuca rubra commutata, Festuca rubra trichophylla, Festuca duriuscula, Festuca ovina, Festuca arundinacea, Poa trivialis, Poa pratensis, Poa palustris, Bromus catharticus, Bromus sitchensis, Bromus inermis, Deschampsia caespitose, Agrostis capilaris, Agrostis stolonifera, Arrhenatherum elatius, Phalaris arundinacea, Brachypodium distachyon* and *Trisetum flavescens*. Most preferably the polynucleotide according to the invention is from *Lolium perenne*.

Such hybridizing polynucleotides may be identified and isolated by using the polynucleotides described hereinabove or parts or reverse complements thereof, for instance by hybridization according to standard methods (see for instance Sambrook and Russell (2001), Molecular Cloning: A Laboratory Manual, CSH Press, Cold Spring Harbor, N.Y., USA). Polynucleotides comprising the same or substantially the same nucleotide sequence as indicated in SEQ ID NO: 1 or parts thereof can, for instance, be used as hybridization probes. The fragments used as hybridization probes can also be synthetic fragments which are prepared by usual synthesis techniques, and the sequence of which is substantially identical with that of a polynucleotide according to the invention.

The molecules hybridizing with the polynucleotides of the invention also comprise fragments, derivatives and allelic variants of the above-described polynucleotides having the same function. Function means with respect to SEQ ID NO: 1 that it leads to a prevention of flowering when expressed in sense orientation in plants.

Herein, fragments are understood to mean parts of the polynucleotides which are long enough to show the same function. In this context, the term derivative means that the sequences of these molecules differ from the sequences of the above-described polynucleotides in one or more positions and show a high degree of homology to these sequences, preferably within sequence ranges that are essential for their function.

Preferably, the degree of homology is determined by comparing the respective sequence with the nucleotide sequence of the coding region of SEQ ID NO: 1. When the sequences which are compared do not have the same length, the degree of homology preferably refers to the percentage of nucleotide residues in the shorter sequence which are identical to nucleotide residues in the longer sequence. The degree of homology can be determined conventionally using known computer programs such as the DNASTAR program with the ClustalW analysis. This program can be obtained from DNASTAR, Inc., 1228 South Park Street, Madison, Wis. 53715 or from DNASTAR, Ltd., Abacus House, West Ealing, London W13 0AS UK (support@dnastar.com) and is accessible at the server of the EMBL outstation.

When using the Clustal analysis method to determine whether a particular sequence is, for instance, 80% identical to a reference sequence the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Alternative programs which are used for database searching and sequence alignment and comparison, for example, from the Wisconsin Package Version 10.2, such as BLAST, FASTA, PILEUP, FINDPATTERNS or the like (GCG, Madison, Wis.) or public available sequence databases such as GenBank, EMBL, Swiss-Prot and PIR or private sequence databases such as PhytoSeq (Incyte Pharmaceuticals, Palo Alto, Calif.) may be used to determine sequence identity. The Alignment for sequence comparison may be conducted by the local homology algorithm of Smith and Waterman (Adv. Appl. Math. 2 (1981), 482), by the homology alignment algorithm of Needleman and Wunsch (J. Mol. Biol. 48 (1970), 443), by the search for similarity method of Pearson and Lipman (Proc. Natl. Acad. Sci. USA. 85 (1988) 2444), by computerized implementations of these algorithms.

Preferably, the degree of homology of the hybridizing polynucleotide is calculated over the complete length of its coding sequence. It is furthermore preferred that such a hybridizing polynucleotide, and in particular the coding sequence comprised therein, has a length of at least 200 nucleotides, preferably at least 400 nucleotides, more preferably of at least 600 nucleotides, even more preferably of at least 800 nucleotides and most preferably of at least 1000 nucleotides.

Preferably, sequences hybridizing to a polynucleotide according to the invention comprise a region of homology of at least 90%, preferably of at least 93%, more preferably of at least 95%, still more preferably of at least 98% and particularly preferred of at least 99% identity to an above-described polynucleotide, wherein this region of homology has a length of at least 400 nucleotides, more preferably of at least 600 nucleotides, even more preferably of at least 800 nucleotides and most preferably of at least 1000 nucleotides.

Homology, moreover, means that there is a functional and/or structural equivalence between the corresponding polynucleotides or the polypeptides encoded thereby. Polynucleotides which are homologous to the above-described molecules and represent derivatives of these molecules are normally variations of these molecules which represent modifications having the same biological function. They may be either naturally occurring variations, preferably orthologs of a polynucleotide comprising the nucleotide sequence of SEQ ID NO:1, for instance sequences from other alleles, ecotypes, varieties, species, etc., or mutations, and said mutations may have formed naturally or may have been produced by deliberate mutagenesis. The variants, for instance allelic variants, may be naturally occurring variants or variants produced by chemical synthesis or variants produced by recombinant DNA techniques or combinations thereof. Deviations from the above-described polynucleotides may have been produced, e.g., by deletion, substitution, insertion and/or recombination.

The polypeptides encoded by the different variants of the polynucleotides of the invention possess certain characteristics they have in common with the polypeptide comprising the amino acid sequence of SEQ ID NO:2. These include for instance biological activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

The polynucleotides of the invention can be DNA molecules, in particular genomic DNA or cDNA. Moreover, the polynucleotides of the invention may be RNA molecules. The polynucleotides of the invention can be obtained for instance from natural sources or may be produced synthetically or by recombinant techniques, such as PCR.

In a further aspect, the present invention relates to recombinant nucleic acid molecules comprising a polynucleotide of the invention described above. The term "recombinant nucleic acid molecule" refers to a nucleic acid molecule which contains in addition to a polynucleotide of the invention as described above at least one further heterologous coding or non-coding nucleotide sequence. The term "heterologous" means that said nucleotide sequence originates from a different species or from the same species, however, from a different location in the genome than said polynucleotide to which it is added. The term "recombinant" implies that nucleotide sequences are combined into one nucleic acid molecule by the aid of human intervention. The recombinant nucleic acid molecule of the invention can be used alone or as part of a vector.

For instance, the recombinant nucleic acid molecule may encode the polypeptide encoded by a polynucleotide according to the invention fused to a marker sequence, such as a peptide which facilitates purification of the fused polypeptide. The marker sequence may for example be a hexa-histidine peptide, such as the tag provided in a pQE vector (Qiagen, Inc.) which provides for convenient purification of the fusion polypeptide. Another suitable marker sequence may be the HA tag which corresponds to an epitope derived from influenza hemagglutinin polypeptide (Wilson, Cell 37 (1984), 767). As a further example, the marker sequence may be glutathione-S-transferase (GST) which, apart from providing a purification tag, enhances polypeptide stability, for instance, in bacterial expression systems. If it furthermore preferred that the marker sequence contains a protease cleavage site such as the thrombin cleavage site allowing to remove the marker sequence or a part of it from the expressed polypeptide.

In a preferred embodiment, the recombinant nucleic acid molecules further comprises expression control sequences operably linked to the polynucleotide comprised by the recombinant nucleic acid molecule, more preferably these recombinant nucleic acid molecules are expression cassettes. The term "operably linked" (or "operatively linked"), as used throughout the present description, refers to a linkage between one or more expression control sequences and the coding region or parts of the polynucleotide to be expressed in such a way that expression is achieved under conditions compatible with the expression control sequence(s).

Expression comprises transcription of the heterologous DNA sequence into an RNA sequence, which may be a translatable or a non-translatable RNA sequence. Examples for non-translatable RNA molecules are antisense molecules, cosuppression molecules, ribozymes or RNAi molecules. These embodiments are described in more detail below in connection with the transgenic plant cells according to the invention. Preferably expression means transcription into a translatable mRNA. Regulatory elements ensuring expression in prokaryotic as well as in eukaryotic cells, preferably in plant cells, are well known to those skilled in the art. They encompass promoters, enhancers, termination signals, targeting signals and the like. Examples are given further below in connection with explanations concerning vectors. In the case of eukaryotic cells, expression control sequences may comprise poly-A signals ensuring termination of transcription and stabilization of the transcript, for example, those of the 35S RNA from Cauliflower Mosaic Virus (CaMV) or the nopaline synthase gene from *Agrobacterium tumefaciens*. Additional regulatory elements may include transcriptional as well as translational enhancers. A plant translational enhancer often used is the CaMV omega sequence. Similarly, the inclusion of an intron (e.g. intron-1 from the shrunken gene of maize) has been shown to increase expression levels by up to 100-fold (Mait, Transgenic Research 6 (1997), 143-156; Ni, Plant Journal 7 (1995), 661-676).

Moreover, the invention relates to vectors, in particular plasmids, cosmids, viruses, bacteriophages and other vectors commonly used in genetic engineering, which contain a polynucleotide or recombinant nucleic acid molecule of the invention as described above. In a preferred embodiment of the invention, the vectors are suitable for the transformation of bacterial cells, yeast cells, fungal cells, animal cells or, in particular, plant cells. In a particularly preferred embodiment such vectors are suitable for stable transformation of plants.

In a preferred embodiment, the vectors further comprise expression control sequences operably linked to said polynucleotides contained in the vectors. These expression control sequences may be suited to ensure transcription and synthesis of a translatable RNA in prokaryotic or eukaryotic cells.

The expression of the polynucleotides of the invention in prokaryotic or eukaryotic cells, for instance in *Escherichia coli*, is interesting because it permits a more precise characterization of the biological activities of the encoded polypeptide. In addition, it is possible to insert different mutations into the polynucleotides encoding the polypeptide by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. In this regard, it is on the one hand possible to produce deletion mutants in which polynucleotides are produced by progressive deletions from the 5' or 3' end of the coding DNA sequence, and said polynucleotides lead to the synthesis of correspondingly shortened polypeptides.

Furthermore, the introduction of point mutations is also conceivable at positions at which a modification of the amino acid sequence for instance influences the biological activity or the regulation of the polypeptide.

In the case of expression in plants, plant tissue or plant cells, the introduction of mutations into the polynucleotides of the invention allows the gene expression rate and/or the activity of the polypeptides encoded by the polynucleotides of the invention to be reduced or increased.

For genetic engineering in prokaryotic cells, the polynucleotides of the invention or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Additionally, the present invention relates to, a method for producing genetically engineered host cells comprising introducing the above-described polynucleotides, recombinant nucleic acid molecules or vectors of the invention into a host cell.

Another embodiment of the invention relates to host cells, in particular prokaryotic or eukaryotic cells, genetically engineered with the above-described polynucleotides, recombinant nucleic acid molecules or vectors of the invention or obtainable by the above-mentioned method for producing genetically engineered host cells, and to cells derived from such transformed cells and containing a polynucleotide, recombinant nucleic acid molecule or vector of the invention. In a preferred embodiment the host cell is genetically modified in such a way that it contains said polynucleotide stably integrated into the genome. The term "genetically modified" implies that the polynucleotide of the invention contained in the host cell is "heterologous" (or as used synonymously herein "foreign") with respect to the host cell. This means that said polynucleotide does not occur naturally in the host cell or that it is present in the host cell at a location in the genome different from the location of the corresponding naturally occurring polynucleotide, if present. Preferentially, the host cell of the invention is a bacterial, yeast, fungus, plant or animal (e.g. insect or vertebrate such as mammalian) cell. In a preferred embodiment, the host cell of the invention is a plant cell which may include any conceivable type of plant cell, such as cultured or non-cultured cells, protoplasts, suspension culture cells, callus cells, meristem cells, cells being part of a plant tissue, plant organ and/or plant.

More preferably the polynucleotide can be expressed so as to lead to the production of a polypeptide. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the host organism used. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

In another preferred embodiment the polynucleotide according to the invention can be expressed so as to lead to the production of a non-translatable RNA. Examples for non-translatable RNA molecules are antisense molecules, cosuppression molecules, ribozymes or RNAi molecules. These embodiments are described in more detail below in connection with the transgenic plants and plant cells according to the invention.

The transformation of the host cell with a polynucleotide, recombinant nucleic acid molecule or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc. The polypeptide according to the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Polypeptide refolding steps can be used, as necessary, in completing configuration of the polypeptide. Finally, high performance liquid chromatography (HPLC) can be employed for final purification steps.

Accordingly, the present invention also relates to a method for the production of a polypeptide encoded by a polynucleotide of the invention as described above in which the above-mentioned host cell is cultivated under conditions allowing for the expression of the polypeptide and in which the polypeptide is isolated from the cells and/or the culture medium.

Moreover, the invention relates to a polypeptide which is encoded by a polynucleotide according to the invention or obtainable by the above-mentioned method for the production of a polypeptide encoded by a polynucleotide of the invention.

The polypeptide of the present invention may, e.g., be a naturally purified product or a product of chemical synthetic procedures or produced by recombinant techniques from a prokaryotic or eukaryotic host (for example, by bacterial, yeast, higher plant, insect or mammalian cells in culture). Depending upon the host employed in a recombinant production procedure, the polypeptide of the present invention may be glycosylated or may be non-glycosylated. The polypeptide of the invention may also include an initial methionine amino acid residue. The polypeptide according to the invention may be further modified to contain additional chemical moieties normally not being part of the polypeptide. Those derivatized moieties may, e.g., improve the stability, solubility, the biological half life or absorption of the polypeptide. The moieties may also reduce or eliminate any undesirable side effects of the polypeptide and the like. An overview for these moieties can be found, e.g., in Remington's Pharmaceutical Sciences (18$^{th}$ ed., Mack Publishing Co., Easton, Pa. (1990)). Polyethylene glycol (PEG) is an example for such a chemical moiety which has been used for the preparation of therapeutic polypeptides. The attachment of PEG to polypeptides has been shown to protect them against proteolysis (Sada et al., J. Fermentation Bioengineering 71 (1991), 137-139). Various methods are available for the attachment of certain PEG moieties to polypeptides (for review see: Abuchowski et al., in "Enzymes as Drugs"; Holcerberg and Roberts, eds. (1981), 367-383). Generally, PEG molecules or other additional moieties are connected to the polypeptide via a reactive group found on the polypeptide. Amino groups, e.g. on lysines or the amino terminus of the polypeptide are convenient for this attachment among others.

Furthermore, the present invention also relates to an antibody specifically recognizing a polypeptide according to the invention. The antibody can be monoclonal or polyclonal and can be prepared according to methods well known in the art. The term "antibody" also comprises fragments of an antibody which still retain the binding specificity.

The polypeptide according to the invention, its fragments or other derivatives thereof, or cells expressing them can be used as an immunogen to produce antibodies thereto. The present invention in particular also includes chimeric, single chain, and humanized antibodies, as well as Fab fragments, or the product of an Fab expression library. Various procedures known in the art may be used for the production of such antibodies and fragments.

Antibodies directed against a polypeptide according to the present invention can be obtained, e.g., by direct injection of the polypeptide into an animal or by administering the polypeptide to an animal, preferably a non-human animal. The antibody so obtained will then bind the polypeptide itself. In this manner, even a sequence encoding only a fragment of the polypeptide can be used to generate antibodies binding the whole native polypeptide. Such antibodies can then, e.g., be used to isolate the polypeptide from tissue expressing that polypeptide or to detect it in a probe. For the preparation of monoclonal antibodies, any technique which provides antibodies produced by continuous cell line cultures can be used. Examples for such techniques include the hybridoma technique (Köhler and Milstein, Nature 256 (1975), 495-497), the trioma technique, the human B-cell hybridoma technique (Kozbor et al., Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides according to the present invention. Furthermore, transgenic mice may be used to express humanized antibodies directed against immunogenic polypeptides of the present invention.

In a further preferred embodiment, the invention relates to nucleic acid molecules specifically hybridizing with a polynucleotide of the invention or with a complementary strand of such a polynucleotide.

Such hybridizing nucleic acid molecules may be oligonucleotides having a length preferably of at least 10, in particular at least 15, and particularly preferably of at least 50 nucleotides. Advantageously, their length does not exceed a length of 1000, preferably 500, more preferably 200, still more preferably 100 and most preferably 50 nucleotides. They are characterized in that they specifically hybridize to the polynucleotides of the invention, that is to say that they only to a very minor extent and preferably not at all hybridize to polynucleotides encoding another polypeptide. The hybridizing nucleic acid molecules according to this embodiment can be used for instance as primers for amplification techniques such as PCR or as a hybridization probe for instance in order to isolate related genes. The hybridization conditions and homology values described above in connection with the polynucleotides of the invention may likewise apply in connection with the specifically hybridizing nucleic acid molecules mentioned herein.

Furthermore, the invention relates to a method for producing a transgenic plant comprising the steps of
(a) introducing at least one of the above-described polynucleotides, recombinant nucleic acid molecules or vectors of the invention into the genome of a plant cell; and
(b) regenerating the cell of (a) to a transgenic plant.

Optionally, the method may further comprise step (c) producing progeny from the plants produced in step (b).

In a further aspect, the invention relates to transgenic plants or plant tissue comprising plant cells which are genetically engineered with a polynucleotide of the invention and/or which contain the recombinant nucleic acid molecule or the vector of the invention and to transgenic plants obtainable by the method mentioned above.

Preferably, in the transgenic plant of the invention, the polynucleotide of the invention is expressed at least in one part, i.e. organ, tissue or cell type, of the plant.

The transgenic plants containing the polynucleotides according to the present invention related to SEQ ID NO: 1 or a recombinant nucleic acid molecule or vector containing such a polynucleotide show preferably an altered amount of the corresponding encoded polypeptides and, as a consequence, an altered flowering behaviour. The amount of the protein may be increased or reduced depending on whether a translatable or non-translatable RNA is expressed.

Preferably, the transgenic plants, plant tissue or plant cells are characterized by an increase of the amount of transcript corresponding to the polynucleotide of the invention by at least 20%, preferably at least 50% and more preferably at least 100% as compared to the corresponding wild-type plant, plant tissue or plant cell. Likewise, it is preferred that transgenic plants, plant tissues or plant cells are characterized by an increase of the protein amount of the polypeptide of the invention by at least 20%, preferably at least 50% and more preferably at least 100% as compared to the corresponding wild-type plant, plant tissues or plant cells.

Alternatively, the transgenic plants, plant tissues or plant cells are characterized by a reduction of the amount of transcript corresponding to the polynucleotide of the invention by at least 20%, preferably by at least 50% and more preferably by at least 80% as compared to the corresponding wild-type plant, plant tissue or plant cell. Likewise, it is preferred that transgenic plants, plant tissues or plant cells are characterized by a decrease of the protein amount of the polypeptide of the invention by at least 20%, preferably at least 50% and more preferably at least 80% as compared to the corresponding wild-type plant, plant tissues or plant cells.

According to the provisions of the invention, transgenic plants can be prepared by introducing a polynucleotide into plant cells and regenerating the transformed cells to plants by methods well known to the person skilled in the art.

Methods for the introduction of foreign genes into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, vacuum infiltration, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art. The vectors used in the method of the invention may contain further functional elements, for example "left border"- and "right border"-sequences of the T-DNA of *Agrobacterium* which allow stable integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example co-transformation (Lyznik, Plant Mol. Biol. 13 (1989), 151-161; Peng, Plant Mol. Biol. 27 (1995), 91-104) and/or by using systems which utilize enzymes capable of promoting homologous recombination in plants (see, e.g., WO97/08331; Bayley, Plant Mol. Biol. 18 (1992), 353-361); Lloyd, Mol. Gen. Genet. 242 (1994), 653-657; Maeser, Mol. Gen. Genet. 230 (1991), 170-176; Onouchi, Nucl. Acids Res. 19 (1991), 6373-6378). Methods for the preparation of appropriate vectors are described by, e.g., Sambrook and Russell (2001), Molecular Cloning: A Laboratory Manual, CSH Press, Cold Spring Harbor, N.Y., USA.

Suitable strains of *Agrobacterium tumefaciens* and vectors as well as transformation of *Agrobacteria* and appropriate growth and selection media are well known to those skilled in the art and are described in the prior art (GV3101 (pMK90RK), Koncz, Mol. Gen. Genet. 204 (1986), 383-396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467-8471; Koncz, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46; An, EMBO J. 4 (1985), 277-287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37-48; Vasil, Bio/Technology 11 (1993), 1553-1558 and Christou (1996) Trends in Plant Science 1, 423-431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc. Also, the transformation of monocotyledonous plants by means of *Agrobacterium*-based vectors has been described (Chan et al., Plant Mol. Biol. 22 (1993), 491-506; Hiei et al., Plant J. 6 (1994) 271-282; Deng et al, Science in China 33 (1990), 28-34; Wilmink et al, Plant Cell Reports 11 (1992), 76-80; May et al., Bio/Technology 13 (1995), 486-492; Conner and Dormisse, Int. J. Plant Sci. 153 (1992), 550-555; Ritchie et al. Transgenic Res. 2 (1993), 252-265). An alternative system for transforming monocotyledonous plants is the transformation by the biolistic approach (Wan and Lemaux, Plant Physiol. 104 (1994), 37-48; Vasil et al., Bio/Technology 11 (1993), 1553-1558; Ritala et al., Plant Mol. Biol. 24 (1994) 317-325; Spencer et al., Theor. Appl. Genet. 79 (1990), 625-631). The transformation of maize in particular has been repeatedly described in the literature (see for instance WO 95/06128, EP 0 513 849, EP 0 465 875, EP 29 24 35; Fromm et al, Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The successful transformation of other types of cereals has also been described for instance of barley (Wan and Lemaux, supra; Ritala et al., supra, Krens et al., Nature 296 (1982), 72-74), wheat (Nehra et al., Plant J. 5 (1994), 285-297) and rice. Methods for transforming Lolium, in particular *Lolium perenne*, and *Brachypodium*, in particular *Brachypodium distachyon*, are described in the attached Examples. Methods for transformation of plants of the Poaceae family have been published, e.g., in Altpeter et al. (Mol. Breeding 6 (2000), 519-528 for *Lolium perenne*), Altpeter and Xu (J. Plant Physiol. 157 (2000), 441-448 for *Festuca rubra*), Dalton et al. (Plant Cell Reports 18 (1999), 721-726 for *Lolium perenne, Lolium multiflorum* and *Lolium temulentum*), Dalton et al. (Plant Science 132 (1998), 31-43 for *Lolium multiflorum, Lolium perenne, Festuca arundinacea* and *Agrostis stolonifera*), Foiling et al. (Plant Science 139 (1998), 29-40 for *Lolium*), Spangenberg et al. (J. Plant Physiol. 145 (1995), 693-701 for *Festuca arundinacea* and *Festuca rubra*) and Wang et al. (J. Plant Physiol. 151 (1997), 83-90 for *Lolium perenne* and *Lolium multiflorum*).

The resulting transformed plant cell can then be used to regenerate a transformed plant in a manner known by a skilled person.

The present invention likewise refers to mutant plants showing a prevention of flowering, whereby the definition of the term "prevention of flowering" explained above with regard to the polynucleotides of the present invention accordingly applies to mutant plants. The term "mutant plant" (or "plant mutant"), refers to plants the genotype of which is modified compared to the corresponding source plants, preferably by other means than genetic engineering, i.e. the introduction of an exogenous nucleic acid molecule into plant cells. Such "mutant plants" may be provided by methods known in the art, e.g. produced under the influence of a suitable dose of ionizing radiation (e.g. x-rays, gamma or neutron radiation) or by the effect of suitable mutagens (e.g. EMS, MMS, etc.). Furthermore encompassed are mutant plants wherein the mutation occurs naturally. Mutant plants showing the desired trait, i.e. a prevention of flowering, may be screened out of a pool of mutant plants generated according to standard methods. The selection may be performed for altered flowering in samples taken from these plants. Preferably, selection may be carried out utilizing the knowledge of the nucleotide sequences as provided by the present invention. Consequently, it is possible to screen for a genetic trait being indicative for an altered flowering behaviour. Such a screening approach may involve the application of conventional nucleic acid amplification (e.g. PCR) and/or hybridization techniques.

The transgenic plants of the invention may, in principle, be plants of any plant species. They may be both monocotyledonous and dicotyledonous plants. Preferably, the plants are useful plants, i.e. commercially important plants, cultivated by man for nutrition or for technical, in particular industrial, purposes. They may be sugar storing and/or starch-storing plants, especially cereal species (rye, barley, oat, wheat, rice, maize, millet, sago etc.), pea, marrow pea, cassava, sugar cane, sugar beet and potato; tomato, rape, soybean, hemp, flax, sunflower, cow pea or arrowroot, fiber-forming plants (e.g. flax, hemp, cotton), oil-storing plants (e.g. rape, sunflower, soybean) and protein-storing plants (e.g. legumes, cereals, soybeans). The plants within the scope of the invention also include fruit trees, palms and other trees or wooden plants being of economical value such as in forestry. Moreover, the plants of the invention may be to forage plants (e.g. forage and pasture grasses, such as alfalfa, clover, ryegrass) and vegetable plants (e.g. tomato, lettuce, chicory) or ornamental plants (e.g. roses, tulips, hyacinths). Preferably, the plant belongs to the Poaceae, such as *Phleum* spp., *Dactylis* spp., *Lolium* spp., *Festulolium* spp., *Festuca* spp., *Poa* spp., *Bromus* spp., *Agrostis* spp., *Arrhenatherum* spp., *Phalaris* spp., and *Trisetum* spp., for example, *Phleum pratense, Phleum bertolonii, Dactylis glomerata, Lolium perenne, Lolium multiflorum, Lolium multiflorum westervoldicum, Festulolium braunii, Festulolium loliaceum, Festulolium holmbergii, Festulolium pabulare, Festuca pratensis, Festuca rubra, Festuca rubra rubra, Festuca rubra commutata, Festuca rubra trichophylla, Festuca duriuscula, Festuca ovina, Festuca arundinacea, Poa trivialis, Poa pratensis, Poa palustris, Bromus catharticus, Bromus sitchensis, Bromus inermis, Deschampsia caespitose, Agrostis capilaris, Agrostis stolonifera, Arrhenatherum elatius, Phalaris arundinacea,* and *Trisetum flavescens*.

In a preferred embodiment, the present invention relates to transgenic or mutant plants which show an increase in the amount of the polypeptide encoded by the polynucleotide of the invention compared to a corresponding wild-type plant.

In the transgenic plants according to this embodiment, the increased amount of the corresponding protein is caused by the presence of a suitable foreign nucleic acid molecule in the genome of said plants.

The term "presence of a suitable foreign nucleic acid molecule" as used herein refers to any foreign nucleic acid molecule that is present in cells of said transgenic plant but absent from the cells of the corresponding source plant. Thereby encompassed are nucleic acid molecules, e.g. gene sequences, which differ from a corresponding nucleic acid molecule in the source plant cell by at least one mutation (substitution, insertion, deletion, etc. of at least one nucleotide). Furthermore encompassed by the term "foreign" are nucleic acid molecules which are homologous with respect to the source plant cell but are situated in a different chromosomal location or differ, e.g., by way of a reversed orientation for instance with respect to the promoter.

In principle, the nucleic acid molecule to be introduced in accordance with the present embodiment may be of any conceivable origin. It may be from any organism which comprises such molecules. Furthermore, it may be synthetic or derived from naturally occurring molecules by, e.g., modification of its sequence, i.e. it may be a variant or derivative of a naturally occurring molecule. Such variants and derivatives include but are not limited to molecules derived from naturally occurring molecules by addition, deletion, mutation of one or more nucleotides or by recombination. It is, e.g., possible to change the sequence of a naturally occurring molecule so as to match the preferred codon usage of plants, in particular of those plants in which the nucleic acid molecule shall be expressed.

Preferably, the increase of the amount of the polypeptide in the transgenic plant is caused by the expression of a polynucleotide of the invention which is present in cells of the transgenic plant due to genetic engineering.

The polynucleotide introduced into the transgenic plant can in principle be expressed in all or substantially all cells of the plant. However, it is also possible that it is only expressed in certain parts, organs, cell types, tissues etc. Preferred parts are, e.g., leaves. Moreover, it is possible that expression of the polynucleotide only takes place upon induction or at a certain developmental stage. In a preferred embodiment, the polynucleotide is expressed in those parts of the plant that are involved in flowering, most preferably in the apical meristem.

In order to be expressed, the polynucleotide that is introduced into a plant cell is preferably operatively linked to one or more expression control sequences, e.g. a promoter, active in this plant cell.

The promoter may be homologous or heterologous with regard to its origin and/or with regard to the gene to be expressed. Suitable promoters are for instance the promoter of the 35S RNA of the Cauliflower Mosaic Virus (see for instance U.S. Pat. No. 5,352,605), the ubiquitin-promoter (see for instance U.S. Pat. No. 5,614,399) and the rice actin promoter (U.S. Pat. No. 5,641,876) which lend themselves to constitutive expression, the patatin gene promoter B33 (Rocha-Sosa et al., EMBO J. 8 (1989), 23-29) which lends itself to a tuber-specific expression in potatoes or a promoter ensuring expression in photosynthetically active tissues only, for instance the ST-LS1 promoter (Stockhaus et al., Proc. Natl. Acad. Sci. USA 84 (1987), 7943-7947; Stockhaus et al., EMBO, J. 8 (1989) 2445-2451), the Ca/b-promoter (see for instance U.S. Pat. No. 5,656,496, U.S. Pat. No. 5,639,952, Bansal et al., Proc. Natl. Acad. Sci. USA 89 (1992), 3654-3658) and the Rubisco SSU promoter (see for instance U.S. Pat. No. 5,034,322; U.S. Pat. No. 4,962,028) or the glutelin promoter from wheat which lends itself to endosperm-specific expression (HMW promoter) (Anderson, Theoretical and Applied Genetics 96, (1998), 568-576, Thomas, Plant Cell 2 (12), (1990), 1171-1180), the glutelin promoter from rice (Takaiwa, Plant Mol. Biol. 30(6) (1996), 1207-1221, Yoshihara, FEBS Lett. 383 (1996), 213-218, Yoshihara, Plant and Cell Physiology 37 (1996), 107-111), the shrunken promoter from maize (Maas, EMBO J. 8 (11) (1990), 3447-3452, Werr, Mol. Gen. Genet. 202(3) (1986), 471-475, Werr, Mol. Gen. Genet. 212(2), (1988), 342-350), the USP promoter, the phaseolin promoter (Sengupta-Gopalan, Proc. Natl. Acad. Sci. USA 82 (1985), 3320-3324, Bustos, Plant Cell 1 (9) (1989), 839-853) or promoters of zein genes from maize (Pedersen et al., Cell 29 (1982), 1015-1026; Quatroccio et al., Plant Mol. Biol. 15 (1990), 81-93). However, promoters which are only activated at a point in time determined by external influences can also be used (see for instance WO 93/07279). In this connection, promoters of heat shock proteins which permit simple induction may be of particular interest. Likewise, artificial and/or chemically inducible promoters may be used in this context. Moreover, seed-specific promoters such as the USP promoter from *Vicia faba* which ensures a seed-specific expression in *Vicia faba* and other plants may be used (Fiedler et al., Plant Mol. Biol. 22 (1993), 669-679; Baumlein et al., Mol. Gen. Genet. 225 (1991), 459-467). Moreover, fruit-specific promoters, such as described in WO 91/01373 may be used too. In one embodiment, promoters which ensure constitutive expression are preferred. However, in another preferred embodiment, the polynucleotide may be operatively linked to a promoter which is inducible. For ensuring expression specifically in the apical meristem of plants it is, e.g., possible to use the promoter of the cen gene (see, e.g., WO 97/10339). The promoters described in PCT/EP03/11038 (WO 04/35797) can be used to drive expression in apical/floral/inflorescence meristems. These promotes are derived from MADS box genes.

Moreover, the polynucleotide may be linked to a termination sequence which serves to terminate transcription correctly and to add a poly-A-tail to the transcript which is believed to have a function in the stabilization of the transcripts. Such elements are described in the literature (see for instance Gielen et al., EMBO J. 8 (1989), 23-29) and can be replaced at will. The termination sequence may be from the same gene as the promoter sequence or from a different gene. It may be homologous or heterologous with respect to the gene to be expressed. Particularly suitable terminators are polyadenylation signals, such as the CaMVpolyA signal or the termination signals from the nopaline synthase (nos), the octopine synthase (ocs) or the rbcS genes.

Furthermore, if needed, polypeptide expression can in principle be targeted to any sub-localization of plant cells (e.g. cytosol, plastids, vacuole, mitochondria) or the plant (e.g. apoplast). In order to achieve the localization in a particular compartment, the coding region to be expressed may be linked to DNA sequences encoding a signal sequence (also called "transit peptide") ensuring localization in the respective compartment. It is evident that these DNA sequences are to be arranged in the same reading frame as the coding region to be expressed. Preferably, the proteins of the present invention are localized in the nucleus or the cytosol.

In order to ensure the location in the plastids, it is conceivable to use one of the following transit peptides: of the plastidic Ferredoxin: NADP+ oxidoreductase (FNR) of spinach which is enclosed in Jansen et al. (Current Genetics 13 (1988), 517-522). In particular, the sequence ranging from nucleotides −171 to 165 of the cDNA sequence disclosed therein can be used which comprises the 5' non-translated region as well as the sequence encoding the transit peptide. Another example is the transit peptide of the waxy protein of maize including the first 34 amino acid residues of the mature waxy protein (Klösgen et al., Mol. Gen. Genet. 217 (1989), 155-161). It is also possible to use this transit peptide without the first 34 amino acids of the mature protein. Furthermore, the signal peptides of the ribulose bisphosphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malat dehydrogenase (Gallardo et al., Planta 197 (1995), 324-332), of the glutathione reductase (Creissen et al., Plant J. 8 (1995), 167-175) or of the R1 protein (Lorberth et al. Nature Biotechnology 16, (1998), 473-477) can be used. In order to ensure the location in the vacuole, it is conceivable to use one of the following transit peptides: the N-terminal sequence (146 amino acids) of the patatin protein (Sonnewald et al., Plant J. 1 (1991), 95-106) or the signal sequences described by Matsuoka and Neuhaus (Journal of Experimental Botany 50 (1999), 165-174); Chrispeels and Raikhel (Cell 68 (1992), 613-616); Matsuoka and Nakamura (Proc. Natl. Acad. Sci. USA 88 (1991), 834-838); Bednarek and Raikhel (Plant Cell 3 (1991), 1195-1206); and Nakamura and Matsuoka (Plant Phys. 101 (1993), 1-5).

In order to ensure the localization in the mitochondria, it is for example conceivable to use the transit peptide described by Braun (EMBO J. 11, (1992), 3219-3227).

In order to ensure the localization in the apoplast, it is conceivable to use one of the following transit peptides: signal sequence of the proteinase inhibitor II-gene (Keil et al., Nucleic Acid Res. 14 (1986), 5641-5650; von Schaewen et al., EMBO J. 9 (1990), 30-33), of the levansucrase gene from *Erwinia amylovora* (Geier and Geider, Phys. Mol. Plant Pathol. 42 (1993), 387-404), of a fragment of the patatin gene B33 from *Solanum tuberosum*, which encodes the first 33 amino acids (Rosahl et al., Mol Gen. Genet. 203 (1986), 214-220) or of the one described by Oshima et al. (Nucleic Acid Res. 18 (1990), 181).

In addition to expressing a polynucleotide of the invention that is present in a plant cell due to genetic engineering, an increase of the amount of the corresponding polypeptide in transgenic plants of the invention may also be achieved by other methods known to a skilled person.

For example, the endogenous gene corresponding to a polynucleotide of the invention may be modified at its natural location to cause an increase in the amount of the protein, e.g. by homologous recombination. In particular, the promoter of this gene can for instance be altered in a way that promoter activity is enhanced. In the alternative, other regulatory elements of the gene influencing for instance mRNA stability, translation or post-translational processing or the coding region of the gene can be modified so that the encoded polypeptide shows an increased activity, e.g. by specifically substituting amino acid residues in the catalytically active domain of the polypeptide. Applicable homologous recombination techniques (also known as "in vivo mutagenesis") are known to the person skilled in the art and are described in the literature. One such technique involves the use of a hybrid RNA-DNA oligonucleotide ("chimeroplast") which is introduced into cells by transformation (TIBTECH 15 (1997), 441-447; WO95/15972; Kren, Hepatology 25 (1997), 1462-1468; Cole-Strauss, Science 273 (1996), 1386-1389). Thereby, part of the DNA component of the RNA-DNA oligonucleotide is homologous with the target gene sequence, however, displays in comparison to this sequence a mutation or a heterologous region which is surrounded by the homologous regions. The term "heterologous region" refers to any sequence that can be introduced and which is different from that to be modified. By means of base pairing of the homologous regions with the target sequence followed by a homologous recombination, the mutation or the heterologous region contained in the DNA component of the RNA-DNA oligonucleotide can be transferred to the corresponding gene. By means of in vivo mutagenesis, any part of the gene encoding the polypeptide of the invention can be modified as long as it results in an increase of the biological activity of this protein. Alternatively, the expression or the amount of a protein according to the invention in a cell can also be increased by modulating the expression of genes known to influence/regulate the expression of the gene in question. Thus, if it is, e.g., known that a certain gene represses transcription of the gene in question, the reduction of expression of said gene leads to a higher expression of the gene in question.

Transgenic plants which show an increased amount of the polypeptide according to the invention encoded by a polynucleotide according to the invention show preferably a prevention of flowering as defined above in connection with the polynucleotides according to the invention.

Moreover, the present invention relates in a further preferred embodiment to transgenic or mutant plants which show a reduced amount of a polypeptide encoded by a polynucleotide of the invention compared to a corresponding wild-type plant.

The transgenic plants according to this embodiment show a reduced amount of a polypeptide of the invention due to the presence of a suitable foreign nucleic acid molecule in the genome of its cells.

The above explanations concerning techniques for producing transgenic plants and plant cells as well as suitable transformation techniques and vectors mentioned in connection with the transgenic plants having an increased amount of a polypeptide of the present invention may be likewise applied in the present embodiment.

Methods for specifically reducing the amount of a protein in plant cells by the introduction of nucleic acid molecules are exhaustively and widely described in the literature and are known to the person skilled in the art. These include but are not limited to antisense inhibition, ribozyme inhibition, co-suppression, RNA interference, expression of dominant negative mutants, antibody expression and in vitro mutagenesis approaches.

It is particularly preferred that the nucleic acid molecule introduced into a plant cell in accordance with the present embodiment has to be expressed in the transgenic plant in order to exert the reducing effect upon the amount of the protein. The term "expressed" means for such a nucleic acid molecule that it is at least transcribed, and for some embodiments also translated into a protein, in at least some of the cells of the plant. Preferred examples of such nucleic acid molecules relate to those embodiments of the transgenic plants of the invention wherein said reduced amount of the protein is achieved by an antisense, co-suppression, ribozyme or RNA interference effect or by the expression of antibodies or other suitable (poly)peptides capable of specifically reducing said activity or by the expression of a dominant-negative mutant. These methods are further explained in the following.

Accordingly, the use of nucleic acid molecules encoding an antisense RNA which is complementary to transcripts of a gene of the present invention is a preferred embodiment of the present invention. Thereby, complementarity does not signify that the encoded RNA has to be 100% complementary. A low degree of complementarity may be sufficient as long as it is high enough to inhibit the expression of such protein upon expression of said RNA in plant cells. The transcribed RNA is preferably at least 90% and most preferably at least 95% complementary to the polynucleotide of the invention. In order to cause an antisense effect during the transcription in plant cells such RNA molecules have a length of at least 15 bp, preferably a length of more than 100 bp and most preferably a length or more than 500 bp, however, usually less than 1600 bp, preferably shorter than 1200 bp. Exemplary methods for achieving an antisense effect in plants are for instance described by Müller-Röber (EMBO J. 11 (1992), 1229-1238), Landschütze (EMBO J. 14 (1995), 660-666), D'Aoust (Plant Cell 11 (1999), 2407-2418) and Keller (Plant J. 19 (1999), 131-141) and are herewith incorporated in the description of the present invention. Likewise, an antisense effect may also be achieved by applying a triple-helix approach, whereby a nucleic acid molecule complementary to a region of the gene, encoding the relevant protein, designed according to the principles for instance laid down in Lee (Nucl. Acids Res. 6 (1979), 3073); Cooney (Science 241 (1998), 456) or Dervan (Science 251 (1991), 1360) may inhibit its transcription.

A similar effect as with antisense techniques can be achieved by producing transgenic plants expressing suitable constructs in order to mediate an RNA interference (RNAi) effect. Thereby, the formation of double-stranded RNA leads to an inhibition of gene expression in a sequence-specific fashion. More specifically, in RNAi constructs, a sense portion comprising the coding region of the gene to be inactivated (or a part thereof, with or without non-translated region) is followed by a corresponding antisense sequence portion. Between both portions, an intron not necessarily originating from the same gene may be inserted. After transcription, RNAi constructs form typical hairpin structures. In accordance with the teachings of the present invention, the RNAi technique may be carried out as described by Smith (Nature 407 (2000), 319-320) or Marx (Science 288 (2000), 1370-1372).

Also DNA molecules can be employed which, during expression in plant cells, lead to the synthesis of an RNA which reduces the expression of the gene encoding the polypeptide of the invention in the plant cells due to a co-suppression effect. The principle of co-suppression as well as the production of corresponding DNA sequences is precisely described, for example, in WO 90/12084. Such DNA molecules preferably encode an RNA having a high degree of homology to transcripts of the target gene. It is, however, not absolutely necessary that the coding RNA is translatable into a protein. The principle of the co-suppression effect is known to the person skilled in the art and is, for example, described in Jorgensen, Trends Biotechnol. 8 (1990), 340-344; Niebel, Curr. Top. Microbiol. Immunol. 197 (1995), 91-103; Flavell, Curr. Top. Microbiol. Immunol. 197 (1995), 43-36; Palaqui and Vaucheret, Plant. Mol. Biol. 29 (1995), 149-159; Vaucheret, Mol. Gen. Genet. 248 (1995), 311-317; de Borne, Mol. Gen. Genet. 243 (1994), 613-621 and in other sources.

Likewise, DNA molecules encoding an RNA molecule with ribozyme activity which specifically cleaves transcripts of a gene encoding the relevant protein can be used. Ribozymes are catalytically active RNA molecules capable of cleaving RNA molecules and specific target sequences. By means of recombinant DNA techniques, it is possible to alter the specificity of ribozymes. There are various classes of ribozymes. For practical applications aiming at the specific cleavage of the transcript of a certain gene, use is preferably made of representatives of the group of ribozymes belonging to the group I intron ribozyme type or of those ribozymes exhibiting the so-called "hammerhead" motif as a characteristic feature. The specific recognition of the target RNA molecule may be modified by altering the sequences flanking this motif. By base pairing with sequences in the target molecule, these sequences determine the position at which the catalytic reaction and therefore the cleavage of the target molecule takes place. Since the sequence requirements for an efficient cleavage are low, it is in principle possible to develop specific ribozymes for practically each desired RNA molecule. In order to produce DNA molecules encoding a ribozyme which specifically cleaves transcripts of a gene encoding the relevant protein, for example a DNA sequence encoding a catalytic domain of a ribozyme is bilaterally linked with DNA sequences which are complementary to sequences encoding the target protein. Sequences encoding the catalytic domain may for example be the catalytic domain of the satellite DNA of the SCMO virus (Davies, *Virology* 177 (1990), 216-224 and Steinecke, EMBO J. 11 (1992), 1525-1530) or that of the satellite DNA of the TobR virus (Haseloff and Gerlach, Nature 334 (1988), 585-591). The expression of ribozymes in order to decrease the activity of certain proteins in cells is known to the person skilled in the art and is, for example, described in EP-B1 0 321 201. The expression of ribozymes in plant cells is for example described in Feyter (Mol. Gen. Genet. 250 (1996), 329-338).

Furthermore, nucleic acid molecules encoding antibodies specifically recognizing the relevant protein in a plant, i.e. specific fragments or epitopes of such a protein, can be used for inhibiting the activity of this protein. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein (Nature 256 (1975), 495) and Galfré (Meth. Enzymol. 73 (1981) 3), which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. Expression of antibodies or antibody-like molecules in plants can be achieved by methods well known in the art, for example, full-size antibodies (Düring, Plant. Mol. Biol. 15 (1990), 281-293; Hiatt, Nature 342 (1989), 469-470; Voss, Mol. Breeding 1 (1995), 39-50), Fab-fragments (De Neve, Transgenic Res. 2 (1993), 227-237), scFvs (Owen, Bio/Technology 10 (1992), 790-794; Zimmermann, Mol. Breeding 4 (1998), 369-379; Tavladoraki, Nature 366 (1993), 469-472; Artsaenko, Plant J. 8 (1995), 745-750) and variable heavy chain domains (Benvenuto, Plant Mol. Biol. 17 (1991), 865-874) have been successfully expressed in tobacco, potato (Schouten, FEBS Lett. 415 (1997), 235-241) or *Arabidopsis*, reaching expression levels as high as 6.8% of the total protein (Fiedler, Immunotechnology 3 (1997), 205-216).

In addition, nucleic acid molecules encoding a mutant form of the relevant protein can be used to interfere with the activity of the wild-type protein. Such a mutant form preferably has lost its biological activity and may be derived from the corresponding wild-type protein by way of amino acid deletion(s), substitution(s), and/or additions in the amino acid sequence of the protein. These mutant forms may be naturally occurring or, as preferred, genetically engineered mutants.

In another preferred embodiment, the nucleic acid molecule, the presence of which in the genome of a plant cell leads to a reduction of the amount of the protein, does not require its expression to exert its effect. Correspondingly, preferred examples relate to methods wherein said reduced amount is achieved by in vivo mutagenesis or by the insertion of a heterologous DNA sequence in the corresponding gene.

The term "in vivo mutagenesis", relates to methods where the sequence of the gene encoding the relevant protein is modified at its natural chromosomal location such as for instance by techniques applying homologous recombination. This may be achieved by using a hybrid RNA-DNA oligonucleotide ("chimeroplast") as it is already described supra. For the purpose of reducing the amount of a certain endogenous protein, in vivo mutagenesis can in particular be directed to the promoter, e.g. the RNA polymerase binding site, as well as the coding region, in particular those parts relevant for the activity or a signal sequence directing the protein to the appropriate cellular compartment.

Reduction of the amount of protein may furthermore be achieved by knocking out the corresponding endogenous gene by way of inserting a heterologous DNA sequence into said gene. The term "heterologous DNA sequence" refers to any DNA sequences which can be inserted into the target gene via appropriate techniques other than those described above in connection with in vivo mutagenesis. The insertion of such a heterologous DNA sequence may be accompanied by other mutations in the target gene such as the deletion, inversion or rearrangement of the sequences flanking the insertion site. This embodiment of the invention includes that the introduction of a nucleic acid molecule leads to the generation of a pool, i.e. a plurality, of transgenic plants in the genome of which the nucleic acid molecule, i.e. the heterologous DNA sequence, is randomly spread over various chromosomal locations, and that this generation of transgenic plants is followed by selecting those transgenic plants out of the pool which show the desired genotype, i.e. an inactivating insertion in the relevant gene and/or the desired phenotype, i.e. a reduced amount of the protein and/or other phenotypic traits correlating with a reduced amount, i.e. alterations in flowering behaviour.

Suitable heterologous DNA sequences that can be taken for such an approach are described in the literature and include, for instance, vector sequences capable of self-integration into the host genome or mobile genetic elements. Particularly preferred in this regard are T-DNA or transposons which are well-known to the person skilled in the art from so-called tagging experiments used for randomly knocking out genes in plants. The production of such pools of transgenic plants can for example be carried out as described in Jeon (Plant J. 22 (2000), 561-570) or Parinov (Curr. Op. Biotechnol. 11 (2000), 157-161).

Another example of insertional mutations that may result in gene silencing includes the duplication of promoter sequences which may lead to a methylation and thereby an inactivation of the promoter (Morel, Current Biology 10 (2000), 1591-1594).

Furthermore, it is immediately evident to the person skilled in the art that the above-described approaches, such as antisense, ribozyme, co-suppression, in-vivo mutagenesis, RNAi, expression of antibodies, other suitable peptides or polypeptides or dominant-negative mutants and the insertion of heterologous DNA sequences, can also be used for the reduction of the expression of genes that encode a regulatory protein such as a transcription factor, that controls the expression of the relevant protein or, e.g., proteins that are necessary for the protein to become active. It is also evident from the disclosure of the present invention that any combination of the above-identified approaches can be used for the generation of transgenic plants, which, due to the presence of one or more of the above-described nucleic acid molecules in their cells, display a reduced amount of the relevant protein compared to corresponding source plants. Such combinations can be made, e.g., by (co-) transformation of corresponding nucleic acid molecules into the plant cell, plant tissue or plant or by crossing transgenic or mutant plants that have been generated according to different techniques. Likewise, the transgenic plants of the present invention showing a reduced amount of the relevant protein can be crossed with plants, e.g. transgenic plants, having other desired traits.

The invention also relates to propagation material of the transgenic plants of the invention comprising plant cells according to the invention. The term "propagation material" comprises those components or parts of the plant which are suitable to produce offspring vegetatively or generatively. Suitable means for vegetative propagation are for instance cuttings, callus cultures, rhizomes or tubers. Other propagation material includes for instance fruits, seeds, seedlings, protoplasts, cell cultures etc. The preferred propagation materials are tubers and seeds.

The invention also relates to harvestable parts of the plants of the invention such as, for instance, fruits, seeds, tubers, rootstocks, leaves or flowers.

Corresponding to the above explanations, the invention furthermore relates to a method for preventing flowering in a plant comprising the step of providing a transgenic or mutant plant in which the amount, preferably the expression of a polypeptide encoded by the above-described polynucleotide of the invention is increased compared to a corresponding wild-type plant.

In another aspect the present invention relates to a method of controlling flowering in a plant by providing an inducible restoration of flowering in plants in which flowering is prevented characterized in that (a) the prevention of flowering of the plant is the result of the genetic modification of the plant which leads
    (i) either to the increase of one or more floral inhibitors; or
    (ii) to the reduction of one or more floral enhancers
and
(b) the inducible restoration of the flowering is achieved by
    (iii) either reducing the expression of the floral inhibitor(s) mentioned in (i), above, by induced expression of a corresponding nucleic acid molecule; or
    (iv) increasing the expression of the floral enhancer(s) mentioned in (ii), above, by induced expression of a corresponding nucleic acid molecule, or
    (v) induced expression of one or more floral enhancers different from the floral enhancer(s) mentioned in (ii), above, which is capable of overcoming the floral inhibition caused by the expression of the floral inhibitor of (a)(i) or the reduced expression of the floral enhancer of (a)(ii).

It was found that it is possible to establish a system for controlling flowering in plants in which plants are first genetically modified so as to show a prevention of flowering and flowering is then inducibly restored by inducing expression of nucleic acid molecules which act against the effect of the genetic modification leading to the prevention of flowering.

The term "prevention of flowering" has the same meaning as set forth above in connection with the polynucleotides according to the invention.

The genetic modification which leads to the prevention of flowering is a modification which either leads to an increase of a floral inhibitor in comparison to wild-type plants or to the reduction of a floral enhancer in comparison to wild-type plants.

A "floral inhibitor" is a polynucleotide or polypeptide which reduces, delays or inhibits the formation of sexual reproductive tissues/organs such as floral meristems, inflorescences, spikelets, sepals, petals, carpels, stamens, embryos, pollen, seeds etc. With respect to the meaning of the terms "reduction", "delay" and "inhibition" the same applies as has been set forth above in connection with the nucleic acid molecules according to the invention.

An example of a floral inhibitor is the above-described polypeptide according to the present invention and the corresponding above-described polynucleotide. Thus, in a preferred embodiment of the method according to the invention the amount of a protein according to the invention is increased in comparison to wild-type plants and the plants consequently show a prevention of flowering.

Another example for a floral inhibitor is the TERMINAL FLOWER1 (TFL1) gene known, e.g., from *Arabidopsis thaliana* (WO 97/10339) and from *Lolium perenne* (Jensen et al., Plant Physiol. 125 (2001), 1517-1528; GeneBank accession number AF316419).

Functionally active fragments, derivatives and homologues of LpTFL1 are described in, e.g., P11792US-2003 0226. The use of TFL1 polynucleotides/polypeptides for preventing flowering in plants has already been described in WO 97/10339 and in Jensen et al. (2001; loc. cit.). In principle, any TFL1 polynucleotide/polypeptide from any plant species can be used in the method according to the invention as well as any homolog of TFL1 which may have a different name in other plant species, for example, the cen gene from Antirrhinum disclosed in WO 97/10339. "Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of TFL1. Preferably this function is the property to prevent flowering when overexpressed in plants.

Furthermore, also sequences hybridizing to known TFL1 sequences can be used as long as they effect the prevention of flowering. With respect to "hybridizing" or "hybridisation"

the same applies which has been set forth above in connection with the polynucleotides according to the invention.

Moreover, any part of a TFL1 polynucleotide/polypeptide, of a homolog or of a hybridizing sequence can be used in the method according to the invention as long as the part is long enough to effect the prevention of flowering.

A further example for a floral inhibitor is the FLC/FLF protein (the terms FLC/FLF are synonyms for the type of protein). FCL has already been described in *Arabidopsis thaliana* (WO 00/50615); Michaels and Amasino. Plant Cell 11 (1999), 949-956; Sheldon et al., Plant Cell 11 (1999), 445-458; GeneBank accession numbers AF537203 or AF116527). WO 00/50615 describes three FLC genes from *Arabidopsis thaliana* and two FLC genes from *Brassica rapa*. Moreover, this document describes the characteristics of FLC genes and the encoded proteins and methods for identifying FLC genes from other plant species. This document also describes the use of FLC for preventing flowering in plants. FLF from *A. thaliana* has also been described in WO 00/32780 as well as its use for preventing flowering in plants and its use to isolate homologous sequences from other plant species such as *Brassica napus*. In principle, any FLC/FLF polynucleotide/polypeptide from any plant species can be used in the method according to the invention as well as any homolog of FLC/FLF which may have a different name in other plant species. FLC/FLF proteins have, e.g. also been described for *Brassica oleracea* (GenBank accession number AY 273161) and *Raphanus sativurn* (GenBank accession number AY 273160), *Brassica napus* (GenBank accession numbers AY 036888=BnFLC1, AY 036889=BnFLC2; AY 036890=BnFLC3; AY 036891=BnFLC4 and AY 036892=BnFLC5). "Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of FLC/FLF. Preferably this function is the property to prevent flowering when overexpressed in plants. FLC/FLF proteins are characterized as being MADS box proteins. They are classified as FLF/FLC proteins by sequence homology to the *Arabidopsis thaliana* FLC/FLF locus. Preferably, they are functionally classified as FLC/FLF proteins by their ability to complement the *Arabidopsis* FLC/FLF mutant (Sheldon et al., Plant Cell 11 (1999), 445-458).

Furthermore, also sequences hybridizing to known FLC/FLF sequences can be used as long as they effect the prevention of flowering. With respect to "hybridizing" or "hybridisation" the same applies which has been set forth above in connection with the polynucleotides according to the invention.

Moreover, any part of a FLC/FLF polynucleotide/polypeptide, of a homolog or of a hybridizing sequence can be used in the method according to the invention as long as the part is long enough to effect the prevention of flowering.

A further example for a floral inhibitor is the SVP (short vegetative period) protein. This protein belongs to the MADS box family and was identified in *Arabidopsis* as an early flowering mutation. The SVP protein defines a separate class of MADS box proteins and functions as an inhibitor of flowering (Hartmann et al., Plant J. 21 (2000), 351-360). In principle, any SVP protein from any plant species can be used in the method according to the invention as well as any homolog of SVP which may have a different name in other plant species. In a preferred embodiment SVP from *A. thaliana* is used. In the context of the present invention the term SVP protein also includes SVP-like proteins like the LpMADS 10, LpMADS 14 and LpMADS 16 proteins. The cloning of the nucleotide sequences encoding these proteins is described in the Examples. The nucleotide sequences are shown in SEQ ID NOs:3, 5 and 7, respectively. The corresponding amino acid sequences are shown in SEQ ID NOs: 4, 6 and 8, respectively. Thus, in another preferred embodiment the SVP protein is a protein comprising the amino acid sequence as shown in any one of SEQ ID NOs:4, 6 or 8 or a homolog thereof. "Homolog" means that the corresponding polynucleotide/polypeptide has a certain degree of homology, that is to say sequence identity (preferably at least 40%, more preferably 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore, means that the function is equivalent to the function of the SVP. Preferably this function is the property to prevent flowering when overexpressed in plants.

The increase of the floral inhibitor in the plants can be achieved by methods well known to the person skilled in the art. In this respect, the same possibilities exist as have been described in detail above in connection with the plants according to the invention which show an increased amount of a protein according to the invention. In a preferred embodiment, the increase of the floral inhibitor is achieved by expressing a corresponding nucleic acid molecule in the plant. In this respect, the same possibilities exist as described above in connection with the expression of the polynucleotides of the present invention in plant cells. Preferably, the expression of the corresponding nucleic acid molecule may be under the control of a promoter which ensures constitutive, tissue specific or developmental specific expression.

A "floral enhancer" is a polynucleotide or polypeptide which accelerates or increases the formation of tissues/organs for sexual reproduction such as floral meristems, inflorescences, spikelets, sepals, petals, carpels, stamens, embryos, pollen, seeds etc.

The term "accelerates" means that when the amount of the floral enhancer is increased flowering occurs at an earlier time point when compared to wild-type plants grown under the same conditions. An "earlier time point" preferably means at least 7 days earlier, even more preferably at least 30 days earlier, particularly preferred at least 60 days earlier and most preferably at least 120 days earlier. The term "increases flowering" means that more organs/tissues for sexual reproduction are formed.

An example for a floral enhancer is the INDETERMINATE1 (ID1) gene. It has, e.g., been described for maize (see, e.g., WO 96/34088). This document also discloses the use of ID1 polynucleotides/polypeptides for preventing flowering. The ID1 cDNA from *Lolium perenne*, LpID1, is disclosed in the present application (see polynucleotides relating to SEQ ID NO:9 and the corresponding amino acid sequence SEQ ID NO:10). In principle, any ID1 polynucleotide/polypeptide from any plant species can be used in the method according to the invention as well as any homolog of ID1 which may have a different name in other plant species. In a preferred embodiment the ID1 protein is from *Zea mays* (GenBank accession number AF058757). "Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of ID1. Preferably this function is the property to enhance flowering when overexpressed in plants. ID1 proteins are characterized as belonging to the $C_2H_2$ type family of the zinc finger proteins. It is a transcriptional regulator of the floral transition.

Furthermore, also sequences hybridizing to known ID1 sequences can be used as long as they effect the enhancement of flowering. With respect to "hybridizing" or "hybridisation" the same applies which has been set forth above in connection with the polynucleotides according to the invention.

Moreover, any part of a ID1 polynucleotide/polypeptide, of a homolog or of a hybridizing sequence can be used in the method according to the invention as long as the part is long enough to effect the enhancement of flowering.

The reduction of the expression of the floral inhibitor according to step (b)(iii) of the method according to the invention can be achieved by means and methods known to the person skilled in the art. Suitable means and methods which can be used to reduce expression of a given sequence are known to the skilled person and have been listed above in connection with the plant cells according to the invention in which the expression/amount of a protein according to the invention is reduced. This comprises, e.g., induced expression of corresponding nucleic acid molecules coding for antisense molecules, cosuppression molecules, RNAi or ribozymes, molecules coding for dominant negative mutants, molecules coding for antibodies etc.

The increase of the floral enhancer according to step (b)(iv) of the method according to the invention can be achieved by methods well-known to the person skilled in the art. As mentioned above, the increase is achieved by the induced expression of a corresponding nucleic acid molecule encoding the floral enhancer. In this respect the same applies which had been said above in connection with the possibilities of increasing the expression/amount of a polypeptide according to the invention in a plant cell.

The term "induced expression" refers to a situation where gene expression is obtained or increased by a physical treatment, treatment with a chemical compound, exposure to environmental stimuli, etc.

The floral enhancer mentioned in step (b)(v) of the method according to the invention may be any floral enhancer which is capable of overcoming the floral inhibition resulting from steps (a)(i) or (a)(ii) of the method according to the invention.

One example for such a floral enhancer is the ID1 gene/protein mentioned above.

Another example is the CONSTANS gene (CO) which encodes a polypeptide belonging to the group of zinc finger proteins. The sequences of the CONSTANS genes from *Arabidopsis thaliana* and from *Brassica napus* are, e.g., disclosed in WO 96/14414. The sequence of the CO gene from Lolium perenne is shown in SEQ ID NO:11. The corresponding amino acid sequence is shown in SEQ ID NO:12. A multitude of sequences coding for CO proteins from other plant species are accessible in data bases. In principle, any CO polynucleotide/polypeptide from any plant species can be used in the method according to the invention as well as any homolog of CO which may have a different name in other plant species. One preferred embodiment are CO proteins from *Arabidopsis thaliana* (GenBank accession numbers X94937 and S77098. "Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of CO. Preferably the function of the CO protein is the property to enhance flowering in plants. A characteristic property of CO is that it is a transcription factor with one zinc finger region being composed of two 3-box domains and a C-terminal CCT domain. In *Arabidopsis* and rice the CO protein has been shown to mediate floral stimuli from the photoperiodic pathway.

Furthermore, also sequences hybridizing to known CO sequences can be used as long as they effect the enhancement of flowering. With respect to "hybridizing" or "hybridisation" the same applies which has been set forth above in connection with the polynucleotides according to the invention.

Moreover, any part of a CO polynucleotide/polypeptide, of a homolog or of a hybridizing sequence can be used in the method according to the invention as long as the part is long enough to effect the enhancement of flowering.

A further example for a floral enhancer to be used in step (b)(v) of the method is the LEAFY gene (LFY).

The sequence of the LEAFY gene from *Lolium perenne* is shown in SEQ ID NO:13. The corresponding amino acid sequence is shown in SEQ ID NO:14. The use of LEAFY sequences for enhancing flowering has been disclosed in WO 96/19105. In principle, any LEAFY polynucleotide/polypeptide from any plant species can be used in the method according to the invention as well as any homolog of LEAFY which may have a different name in other plant species. The LEAFY gene has, for example, also been described for *Arabidopsis* (Weigel et al., Cell 69 (1992), 843-859), in tobacco (Kelly et al., Plant Cell 7, (1995), 225-234, *Sinapis alba* (Bonhomme et al., Plant Mol. Biol. 34 (1997), 573-582, where it is called SaMADS D), *Petunia* (Souer et al., Development 125 (1998), 733-742), *Eucalyptus* (Southerton et al., Plant Mol. Biol. 37 (1998), 897-910), *Pinus radiata* (Mouradov et al., Proc. Natl. Acad. Sci. USA 95 (1998), 6537-6542), Impatiens (Pouteau et al., Plant J. 14 (1998), 235-246) and maize (Bomblies et al., Development 130 (2003), 2385-2395). In a preferred embodiment the LEAFY sequence used in the method according to the invention is the sequence from *Arabidopsis thaliana* as shown in GenBank Accession number M91208.

"Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of LEAFY Preferably this function is the property to enhance flowering in plants. LEAFY proteins belong to the group of so-called "meristem identity genes" which specify vegetative or floral identity of the shoot apical meristem.

Furthermore, also sequences hybridizing to known LEAFY sequences can be used as long as they effect the enhancement of flowering. With respect to "hybridizing" or "hybridisation" the same applies which has been set forth above in connection with the polynucleotides according to the invention.

Moreover, any part of a LEAFY polynucleotide/polypeptide, of a homolog or of a hybridizing sequence can be used in the method according to the invention as long as the part is long enough to effect the enhancement of flowering.

Further examples of floral enhancers to be used in step (b)(v) of the method according to the invention are APETALA-1 (AP-1) proteins. These are MADS box proteins and also belong to the group of "meristem identity genes". AP-1 was first isolated from *A. thaliana* (Mandel et al., Nature 360 (1992), 273-277). Preferably, the AP-1 protein is a MADS1, MADS2 or MADS3 protein. These are AP-1 homologs isolated from *Lolium perenne*. LpMADS1 is the closest homolog to the major vernalization locus in wheat, VRN1 (Yan et al., Proc. Natl. Acad. Sci. USA 100 (2003), 6263-6268). VNR1 (TmAP1) is a close AP-1 homolog and specifies vernalization requirement in wheat. Spring varieties which do not require vernalization show a basal expression of TmAP1 whereas winter types which require vernalization in order to flower only show TmAP1 expression in response to vernalization. Similarly, it has been shown that LpMADS1, -2, -3 are up regulated by vernalization in *L. perenne* (Petersen et al., J. Plant Physiol. 161 (2004), 439-447).

The sequences of MADS1, 2 and 3 of *Lolium perenne* are shown in SEQ ID NOs:15, 17 and 19, respectively. Homologs to MADS 1, 2 and 3 of *L. perenne* are known, e.g., from *Lolium temulentum* and other cereals, such as wheat. The use of AP-1 to manipulate flowering time in plant has been suggested in WO 97/46078 and U.S. Pat. No. 5,844,119. The use of MADS box proteins to manipulate flowering in *Lolium* and *Festuca* plant species has been suggested in WO 02/33091.

In principle, any AP-1 and in particular any MADS1, 2 or 3 polynucleotide/polypeptide from any plant species can be used in the method according to the invention as well as any homolog of AP-1 or MADS1, 2, 3 which may have different names in other plant species. In a preferred embodiment the AP-1 protein is from *Arabidopsis thaliana* (see GenBank accession number Z16421). "Homolog" means that the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homolog" furthermore means that the function is equivalent to the function of MADS1, 2, 3 or AP-1. Preferably this function is the property to enhance flowering in plants.

Furthermore, also sequences hybridizing to known AP-1, MADS1, 2 or 3 sequences can be used as long as they effect the enhancement of flowering. With respect to "hybridizing" or "hybridisation" the same applies which has been set forth above in connection with the polynucleotides according to the invention.

Moreover, any part of an AP-1 or of a MADS1, 2 or 3 polynucleotide/polypeptide, of a homolog or of a hybridizing sequence can be used in the method according to the invention as long as the part is long enough to effect the enhancement of flowering.

A further example for a floral enhancer is the SOC-1 (suppressor of overexpression of CO-1) protein (also known as AGL20). Mutations of SOC-1 partially suppress the effect of 35 S::CO and SOC-1 integrates signals from the photoperiod, vernalization and gibberelin floral promotive pathways (Borner et al., Plant J. 24 (2000), 591-599; Lee et al., Genes Dev. 14 (2000), 2366-2376; Samach et al., Science 288 (2000), 1613-1616). SOC-1 expression gradually increases during development and is up-regulated by vernalization and GA application (Borner et al., loc. cit.). The photoperiodic pathway gene CO and the vernalization pathway gene FLC regulate SOC-1 expression thereby modulating flowering time. CO does this largely by increasing activity of SOC-1, whereas FLC delays flowering, at least in part, by repressing the expression of SOC-1 (Samach et al., loc. cit.). SOC-1 homologs have been isolated from different plant species, e.g., *Arabiodopsis* (NM 130128), rice (AB003328) and maize (AF112150). In principle, any SOC-1 protein from any plant species can be used in the method according to the invention as well as any homolog of SOC-1 which may have a different name in other plant species. In a preferred embodiment SOC-1 from *A. thaliana* is used. "Homolog" means that the corresponding polynucleotide/polypeptide has a certain degree of homology, that is to say sequence identity (preferably at least 40%, more preferably 60%, even more preferably 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homology" furthermore means that the function is equivalent to the function of SOC-1. Preferably this function is the property to enhance flowering in plants.

A further example for a floral enhancer is the FT protein. This protein belongs to the family of PEBP proteins and has been shown to play a role opposite to TFL1 in mediating flower inducing signals in *Arabidopsis* (Kardailsky et al., Science 286 (1999), 1962-1965). In principle, any FT protein from any plant species can be used in the method according to the invention as well as any homolog of FT which may have a different name in other plant species. In a preferred embodiment FT from *A. thaliana* is used. "Homolog" means that the corresponding polynucleotide/polypeptide has a certain degree of homology, that is to say sequence identity (preferably at least 40%, more preferably 60%, even more preferably 65%, particularly preferred at least 66%, 68%, 70%, 75%, 80%, 86%, 88%, 90%, 92%, 95%, 97% or 99%). With respect to the terms "homology" and "sequence identity" the same applies which had been set forth above in connection with the polynucleotides of the present invention. "Homology" furthermore means that the function is equivalent to the function of FT. Preferably this function is the property to enhance flowering in plants.

A variety of inducible systems, well known to those skilled in the art, may be employed for controlled restoration of flowering, e.g. the tetracycline repressor (TetR)-based tetracycline inducible system, the glucocorticoid receptor-based, steroid-inducible system, the estrogen receptor-based, steroid-inducible system, the ecdysone receptor-based, insecticide-inducble system, the ACEI-based, copper-inducible system, or other promoters that are responsive to growth regulators, metabolic signals, nutrients, elicitors, wound signals, herbicide safeners and chemicals that induce genes for systemic acquired resistance, e.g. the In2-2 (Inducible gene s-s) promoter or the benzothiadiazole (BTH)-inducible PR-1a promoter.

Figure 13:
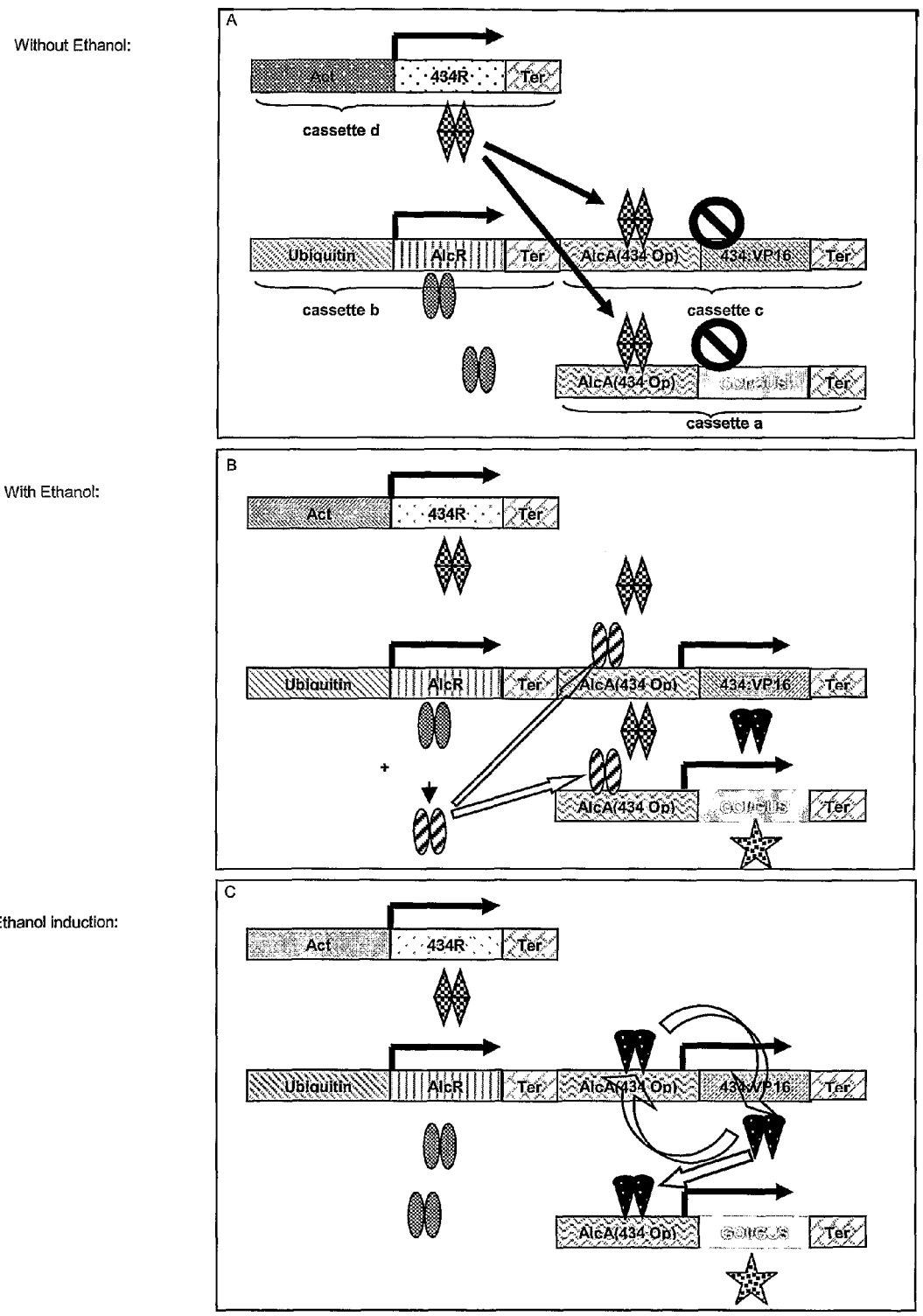

In a preferred embodiment of the method according to the present invention the induced restoration of flowering is achieved by ethanol inducible expression, most preferably by the use of the ethanol-inducible promoter (AlcA) in combination with the ethanol-regulated transcription factor AlcR from *Aspergillus nidulans*. This system is described in detail in the appended Examples and its use in model and crop plant species has already been shown in Sweetman et al. (Plant Physiol. 129 (2002), 943-948). A preferred variant of the ethanol inducible system includes an inducible self-maintaining loop based on one construct containing an artificial fusion of the alcA-minimal35S promoter to –434 operator sequences controlling the expression of the 434/VP16 activator protein together with a constitutive promoter controlling the expression of the AlcR transcription factor. An ethanol pulse will lead to the transient expression of the 434/VP16 activator protein that in turn will activate its own stable expression via the 434 operator sequences introduced into the alcA-minimal35S promoter. This stable expression of the 434/VP16 activator protein is then used to stably express the floral restorer polypeptide on a separate gene cassette, controlled by the alcA-minimal35S promoter with ~434 operator elements. To assure that the self-maintaining loop is not initiated caused by a certain leakiness of the artificial alcA-minimal35S promoter with 434 operator elements yet another construct containing a constitutive promoter controlling the expression of the 434-repressor protein is introduced repressing any leaky expression of the 434/VP16 activator protein. The combination of the different gene cassettes as illustrated in FIG. 13 ensures a repressed state of the loop without ethanol (via repression of transcription by the 434-repressor), an inducible expression by ethanol induction and a stably maintained expression by the 343/VP16 activator protein.

The method according to the present invention can in principle be applied to any plant which shows flowering.

Preferably, the plant is a dicotyledonous (dicot) or monocotyledonous (monocot) perennial or biennial plant. More preferably, the plant belongs to the monocots, such as Poaceae, such as *Phleum* spp., *Dactylis* spp., *Lolium* spp., *Festulolium* spp., *Festuca* spp., *Poa* spp., *Bromus* spp., *Agrostis* spp., *Arrhenatherum* spp., *Phalaris* spp., and *Trisetum* spp., for example, *Phleum pratense, Phleum bertolonii, Dactylis glomerata, Lolium perenne, Lolium multiflorum, Lolium multiflorum westervoldicum, Festulolium braunii, Festulolium loliaceum, Festulolium holmbergii, Festulolium pabulare, Festuca pratensis, Festuca rubra, Festuca rubra rubra, Festuca rubra commutata, Festuca rubra trichophylla, Festuca duriuscula, Festuca ovina, Festuca arundinacea, Poa trivialis, Poa pratensis, Poa palustris, Bromus catharticus, Bromus sitchensis, Bromus inermis, Deschampsia caespitosa, Agrostis capilaris, Agrostis stolonifera, Arrhenatherum elatius, Phalaris arundinacea*, and *Trisetum flavescens*.

In a further aspect the present invention relates to a system for controlling expression of a gene of interest in plant cells comprising the following elements:
(a) an expression cassette in which the gene of interest is placed under the control of the Alc A promoter which comprises a 434 operator sequence;
(b) an expression cassette in which the coding sequence encoding the Alc Regulator (AlcR) is placed under the control of a promoter active in plant cells; and
(c) an expression cassette in which a coding sequence encoding an artificial 434/VP16 transcription factor is placed under the control of the AlcA promoter containing a 434 operator sequence.

In a preferred embodiment the system according to the invention furthermore comprises:
(d) an expression cassette in which a coding region encoding a 434-repressor protein is placed under the control of a promoter active in plant cells.

The system for controlling expression of a gene of interest in plant cells according to the invention is an "ethanol inducible self-maintaining loop system". The AlcA promoter upon administration of ethanol is activated by the AlcR protein. In the system, according to the invention the ethanol induction is not only used directly to control expression of a gene of interest, instead it is also used to induce an artificial transcription factor (434/VP16). This transcription factor activates in a second step the expression of the gene of interest from an artificial promoter (alcA-plant promoter with 434 operator sequences). In order to establish the self-maintaining loop a further gene cassette (cassette (c)) is introduced expressing the 434/VP16 transcription factor itself from an artificial promoter (alcA-plant promoter with 434 operator sequences). One ethanol pulse will produce the first 434/VP16 transcription factor molecules, which in turn will produce itself in a self-maintaining loop from gene cassette (c) and in turn further activate the expression of the gene of interest. The self-maintaining loop will reset during meiosis and seed production so that in the next generation the loop is inactivated and the gene of interest is not expressed. In order to exclude leakiness of the self-maintaining loop in the un-induced state gene cassette (d) may be introduced constitutively expressing the 434-repressor protein. The 434-repressor secures the tightness of the artificial promoter (alcA-plant promoter with 434 operator sequences) driving the expression of the artificial activator (434/VP16) and the gene of interest. Only an ethanol-induced over-expression of the 434/VP16 activator will overcome the repression of the alcA-plant promoter with 434 operator sequences by the 434-repressor. For a better understanding the system is schematically drawn in FIG. 12.

The gene of interest expression of which is controlled in the system according to the invention can be any gene intended to be expressed in plant cells. It may, e.g. encode a polypeptide or an RNA intended to repress expression of a gene, e.g. an antisense RNA, an RNAi, a ribozyme, a cosupression RNA etc.

The AlcA promoter is the strong ethanol inducible alcohol dehydrogenase promoter from the ethanol utilization regulon from *Aspergillus nidulans* (Lockingon et al., Gene 33 (1985), 137-149). The AlcA promoter and expression systems using it have already been described in, e.g., Felenbok (J. Biotechnol. 17 (1991), 11-17) and the use of it in plants has already been described, e.g., by Caddick et al. (Nature Biotechnol. 16 (1998), 177-180), Salter et al. (Plant J. 16 (1998), 127-132), Roslan et al. (Plant J. 28 (2001), 225-235) and Sweetman et al. (Plant Physiol. 129 (2002), 943-948). The AlcA promoter used in the system according to the present invention is preferably a promoter as described in one of the systems of the references cited above or as described in Kulmburg et al. (J. Biol. Chem. 267 (1992), 21146-21153). The AlcA promoter in expression cassettes (a) and (c) of the system according to the invention comprises a 434 operator sequence, i.e. the sequence of the right operator $O_R2$ of bacteriophage 434 (see, e.g., Bushman (J. Mol. Biol. 230 (1993), 28-40)). The corresponding sequence is shown in FIG. 15.

The AlcR encoded by expression cassette (b) is the transactive regulatory protein in the ethanol utilization regulon of *Aspergillus nidulans* as described in Felenbok (loc. cit.). Its use for controlling expression of genes in plants has already been described in e.g. Caddick et al. (loc. cit.), Salter et al. (loc. cit.), Roslan et al. (loc. cit.), Sweetman et al. (loc. cit.), and Devenaux et al. (Plant J. 36 (2003), 918-930). Preferably, the AlcR is the protein encoded by the sequence disclosed in Felenbok et al. (Gene 73 (1988), 385-396) or in Kulmburg et al. (J. Biol. Chem. 267 (1992), 21146-21153).

The AlcR in cassette (b) is placed under the control of a promoter active in plant cells. This can be any promoter active in plant cells. Examples have been listed in connection with the polynucleotides according to the invention. Preferably, the plant promoter is a tissue specific promoter. Most preferably, the plant promoter ensures constitutive expression. Examples for promoters ensuring constitutive expression in plant cells are the ubiqutin promoter, the CaMV 35S promoter or the rice actin promoter.

The artificial transcription factor 434/VP16 in expression cassette (c) is a fusion of the 434 and VP16 activator proteins (see Wilde et al., Plant Mol. Biol. 24 (1994), 381-388). Such an artificial transcription factor has, e.g., also already been disclosed in Storgaard et al. (Transgenic Research 11 (2002), 151-159).

The expression of the artificial 434/VP16 transcription factor is placed under the control of the AlcA promoter which contains a 434 operator sequence (Kulmburg et al., J. Biol. Chem. 267 (1992), 21146-21153).

The promoter driving expression of the gene of interest and of the 434/VP16 transcription factor, apart from the AlcA promoter, preferably also comprises part of a plant promoter required for a minimal transcriptional activity. An example is the minimal CaMV 35S promoter (Gallie et al., Nucl. Acids Res. 15 (1987), 3257-3273).

The expression cassette (d) contains a coding sequence encoding a 434-repressor protein. The term "434 repressor" refers to repressor of temperate phages, such as 434 and lambda, which control transcription by binding a set of DNA operator sites. The different affinity of the repressors for each of these sites ensures efficient regulation. The repressor recognizes its operators by its complementary to a particular DNA conformation as well as by a direct interaction with base pairs in the major groove (Andersen et al., Nature 326 (1987), 846-852; Koudelka, Nucl. Acids Res. 26 (1998), 669-675). The use of the operator site in combination with the receptor protein in other systems confers transcriptional repression (Webster and Bramma, Microbiology-UK 141 (1995), 2191-2200; Part 9). Expression of the 434-repressor protein is driven by a promoter active in plant cells. In this respect, the same applies as has been set forth supra in connection with the promoter controlling expression of AlcR.

The system according to the invention has the advantage that multiple treatments with ethanol can be avoided due to the self-maintaining loop.

The present invention also relates to plant cells or plants comprising a system according to the invention. These can, in principle, be plants of any type, e.g. monocotyledonous or dicotyledonous plants, preferably perennial or biennial plants. More preferably, the plant belongs to the monocots, such as Poaceae, such as *Phleum* spp., *Dactylis* spp., *Lolium* spp., *Festulolium* spp., *Festuca* spp., *Poa* spp., *Bromus* spp., *Agrostis* spp., *Arrhenatherum* spp., *Phalaris* spp., and *Trisetum* spp., for example, *Phleum pratense, Phleum bertolonii, Dactylis glomerata, Lolium perenne, Lolium multiflorum, Lolium multiflorum westervoldicum, Festulolium braunii, Festulolium loliaceum, Festulolium holmbergii, Festulolium pabulare, Festuca pretensis, Festuca rubra, Festuca rubra rubra, Festuca rubra commutata, Festuca rubra trichophylla, Festuca duriuscula, Festuca ovina, Festuca arundinacea, Poa trivialis, Poa pratensis, Poa palustris, Bromus catharticus, Bromus sitchensis, Bromus inermis, Deschampsia caespitosa, Agrostis capilaris, Agrostis stolonifera, Arrhenatherum elatius, Phalaris arundinacea*, and *Trisetum flavescens*.

The present invention also relates to a method for controlling expression of a gene of interest in a plant cell or plant which method comprises the use of a system according to the present invention. In a particularly preferred embodiment the gene of interest is a nucleic acid molecule the induced expression of which leads to a restoration of flowering in plants in which flowering is prevented. Most preferably such a nucleic acid molecule is a molecule as defined in anyone of step (b)(iii) to (v) of the method of controlling flowering in a plant according to the invention described above.

These and other embodiments are disclosed and encompassed by the description and examples of the present invention. The disclosure of all literature cited herein is incorporated into the description of the present invention by reference. Further literature concerning any one of the methods, uses and compounds to be employed in accordance with the present invention may be retrieved from public libraries, using for example electronic devices. For example the public database "Medline" may be utilized which is available on the Internet, for example under www.ncbi.nlm.nih.gov/PubMed/medline.html. Further databases and addresses, such as www:ncbi.nlm.nih.gov/, www.infobiogen.fr/, www.fmi.ch/biology/research_tools.html, www.tigr.org/, are known to the person skilled in the art and can also be obtained using, e.g., www.google.de. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

The present invention will now be more fully described with reference to the accompanying examples and drawings. It should be understood, however, that the following description is illustrative only and should not be taken in any way as a restriction on the generality of the invention described above.

FIG. 1: illustrates the expression profile in perennial ryegrass of LpMADS1, LpMADS2 and LpMADS3 during the floral transition.

Transcript levels of LpMADS genes were tested using real-time PCR and data is calculated with the Q-Gene software tool (Muller et al., Biotechniques 32 (2002), 1372). Samples were tested in triplicate and normalized to LpGAPDH and LpACTIN1 (light grey or dark grey bars, respectively), and the mean±SE is shown. Two scales are provided on the y-axis, responding to relative expression level to LpGAPDH (left) and LpACTIN1 (right). The transcript levels were tested on RNA extracted from shoot apex harvest at 3 stages, non-induced (veg), 6 (vern1) and 12 (vern2) weeks vernalized at short day and 4° C., from inflorescence at 6 stages at long day and 20° C. (LD1-LD6), from leaf at non-induced (veg), 12 weeks vernalized (vern2) and long day stage 5 (LD5), from stem, node and root.

Figure 2:
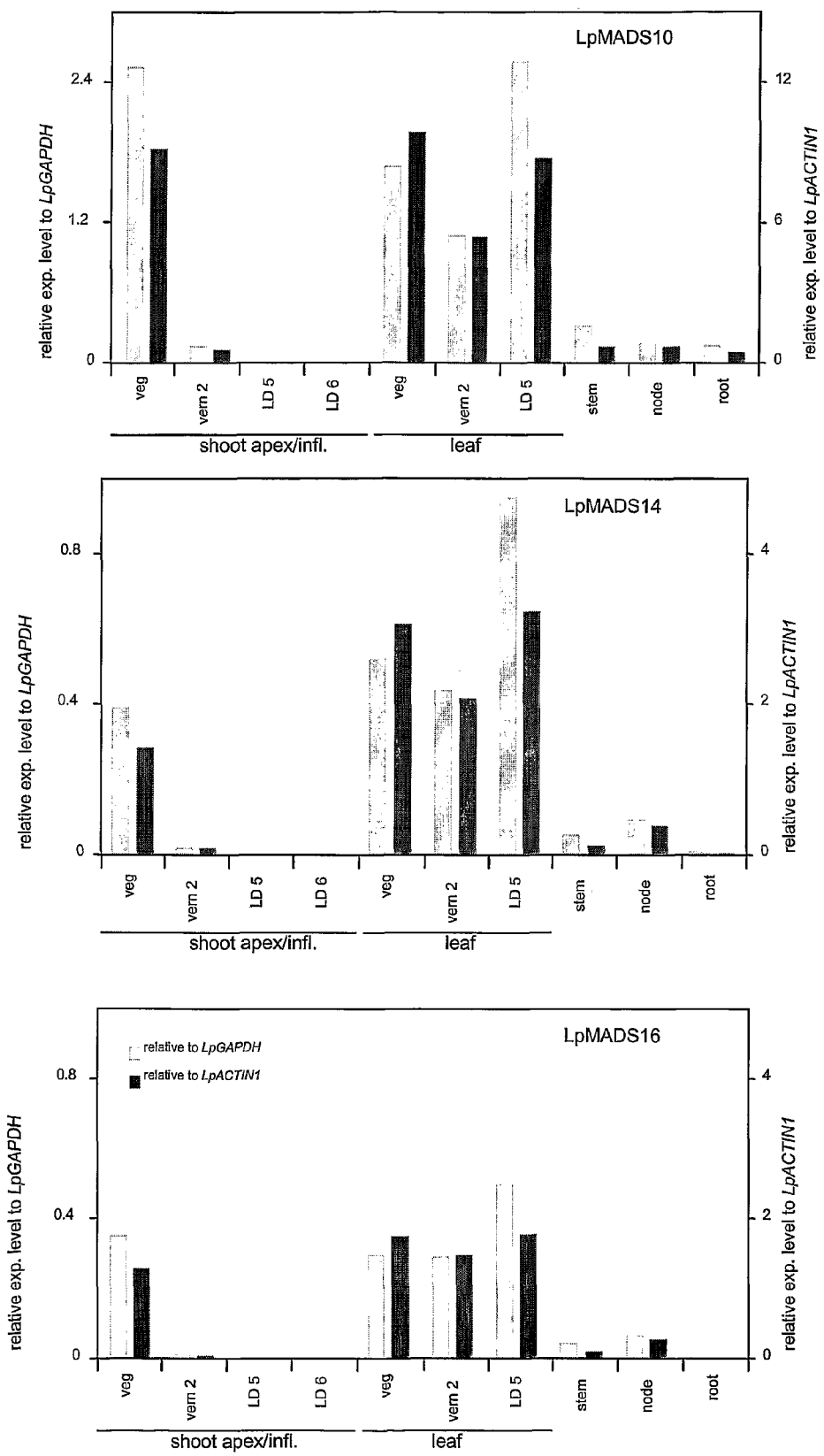

FIG. 2: illustrates the expression profile in perennial ryegrass of LpMADS10, LpMADS14 and LpMADS16 during the floral transition.

Transcript levels of LpMADS genes were tested using real-time PCR and data is calculated with the Q-Gene software tool (Muller et al., loc. cit.). Samples were tested in triplicate and normalized to LpGAPDH and LpACTIN1 (light grey or dark grey bars, respectively). Two scales are provided on the y-axis, responding to relative expression level to LpGAPDH (left) and LpACTIN1 (right). The transcript levels were tested on RNA extracted from shoot apex harvest at 3 stages, non-induced (veg), 6 (vern1) and 12 (vern2) weeks vernalized at short day and 4° C., from inflorescence at 6 stages at long day and 20° C. (LD1-LD6), from leaf at non-induced (veg), 12 weeks vernalized (vern2) and long day stage 5 (LD5), from stem, node and root.

Figure 3:
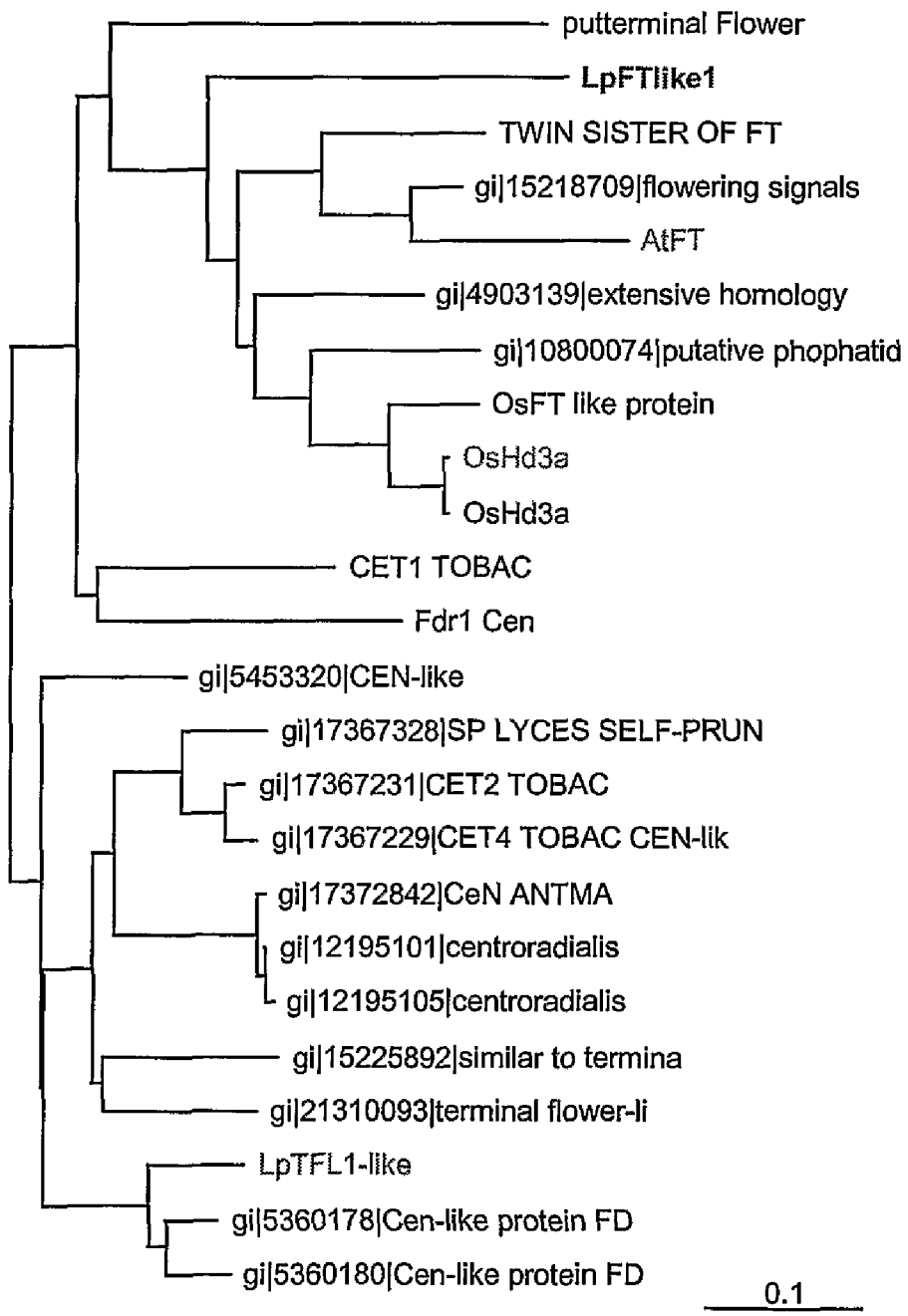

FIG. 3: illustrates the phylogenetic relationship of LpFT-like and other Phosphatidyl Ethanolamine Binding Proteins (PEBS) including the LpTFL1 polypeptide.

FIG. 4: illustrates the late flowering phenotype of *Arabidopsis thaliana* plants (T2-generation) expressing the LpFT-like cDNA under the control of the 35S promoter. Pictures and drawing shows leaf-like structures produced in place of normal floral structures. Drawing illustrates the determinate highly branched growth pattern of the LpFT-like expressing lines very similar to the growth pattern observed by expression of the LpTFL1 transgene. Plants were verified for the presence of the intact transgene by PCR and for expression of transgene by northern blot analysis. The highest expressing lines were extremely late flowering and in some cases completely non-flowering.

Figure 5:
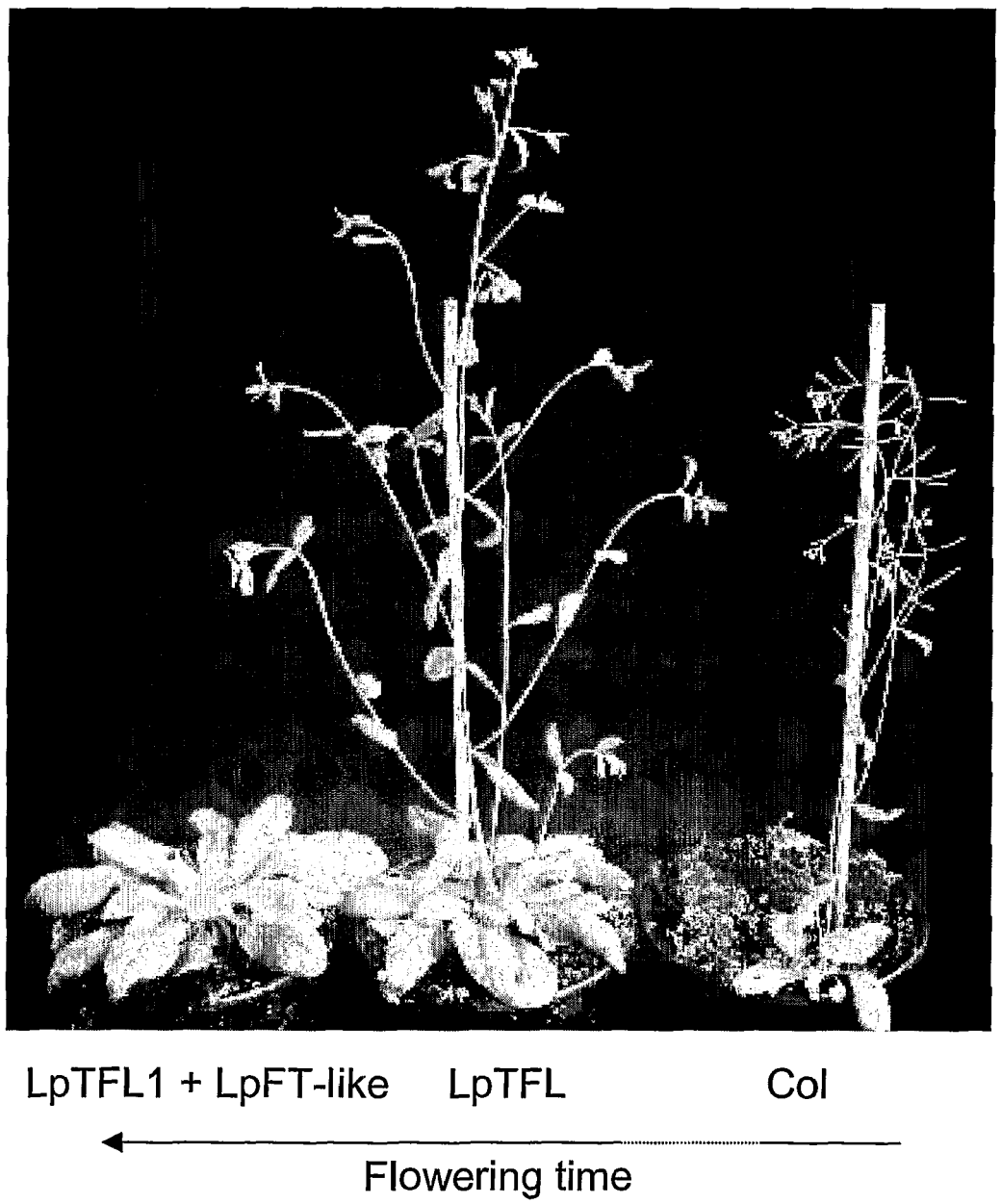

FIG. 5: illustrates the additive late flowering effect of LpTFL1 and LpFT-like. Late flowering *Arabidopsis* plants homozygous for either the LpTFL1 or the LpFT-like ORF under the control of the constitutive 35S promoter were crossed and the offspring scored for flowering phenotype. The offspring carrying both the 35S::LpTFL1 and the 35S::LpFT-like constructs showed an additive lateness in flowering time compared to wild-type plants and plants carrying any of the LpTFL1 or the LpFT-like transgenes alone.

Figure 6:
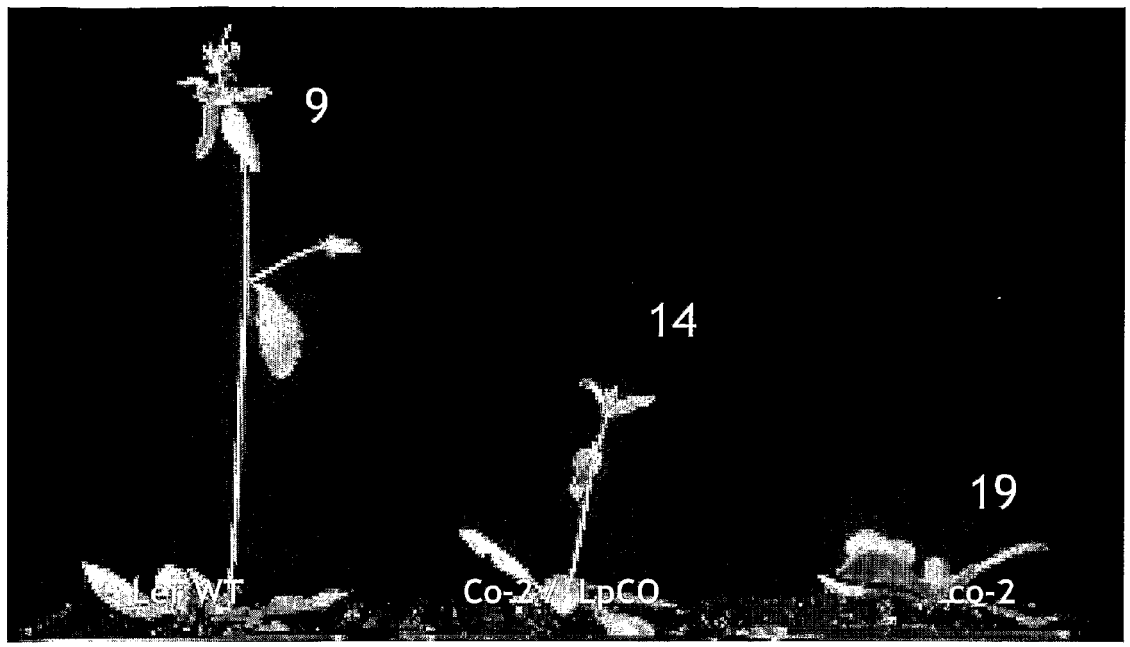

FIG. 6: illustrates the conserved functionality of the LpCO polypeptide, as displayed by functional complementation of the *Arabidopsis thaliana* co-2 mutant. *Arabidopsis* co-2 mutant plants were transformed by the "floral dip" method with the LpCO cDNA under the control of the constitutive 35S promoter. Plants were verified for the presence of the intact transgene by PCR and for expression of the LpCO transgene by northern blot analysis. Plants were phenotypic scored at the T2-generation.

Figure 7:
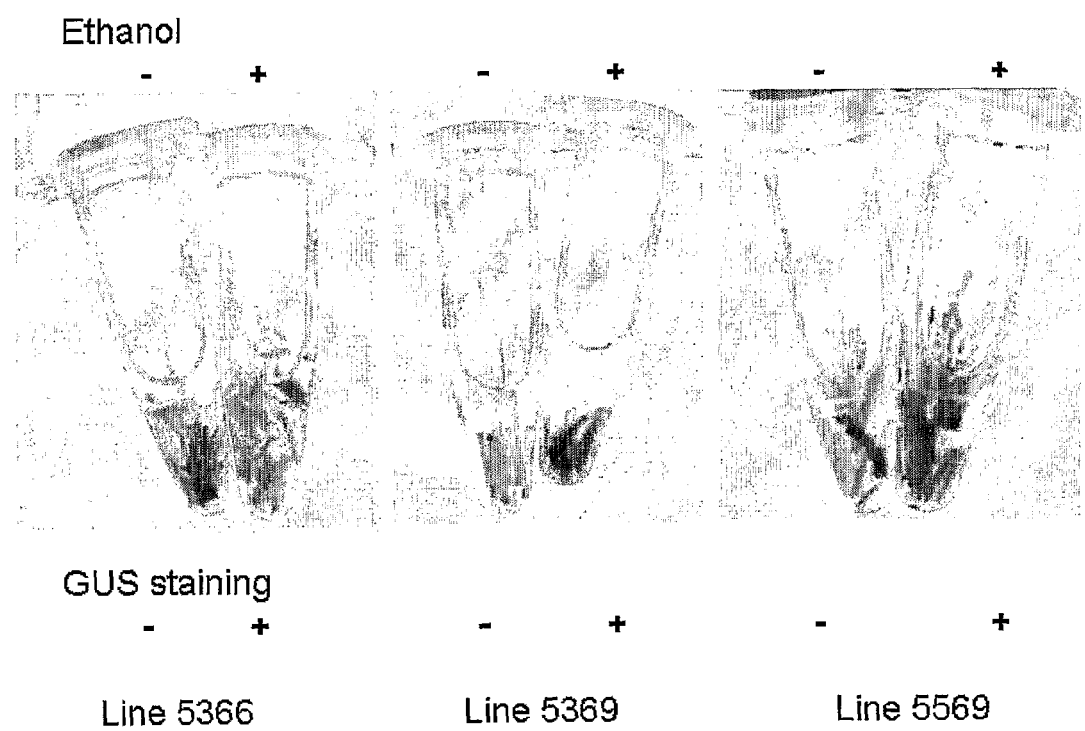

FIG. 7: illustrates ethanol inducible GUS expression in *Festuca rubra* plants transformed with a construct including the maize ubiquitin promoter controlling the AlcR regulator protein and a chimeric AlcA-35S-minimal promoter controlling GUS expression. 3 independent transgenic lines are shown before (−) and after (+) ethanol induction followed by GUS-staining. The principle in the ethanol inducible AlcA/R system: Without ethanol induction AlcR will not bind to the AlcA box. Upon induction with ethanol (or other compounds) AlcR will bind to the AlcA box in the chimeric AlcA/35S-minimal promoter and induce expression of the GUS reporter gene. Transgenic plants verified by PCR and real time PCR were induced with ethanol as follows: Two tillers were cut in pieces and placed in tubes with water. The water volume was doubled with a 4% ETOH solution to give 2% ETOH in the tubes. A beaker with tissue cloth and 4% ETOH was placed in a plastic bag and sealed followed by incubation in LD chamber for 2 days. The induced tillers were cut into X-Gluc reaction buffer and incubated at 37 degree Celsius over the weekend. Then bleached in 96% ETOH over night.

Figure 8:
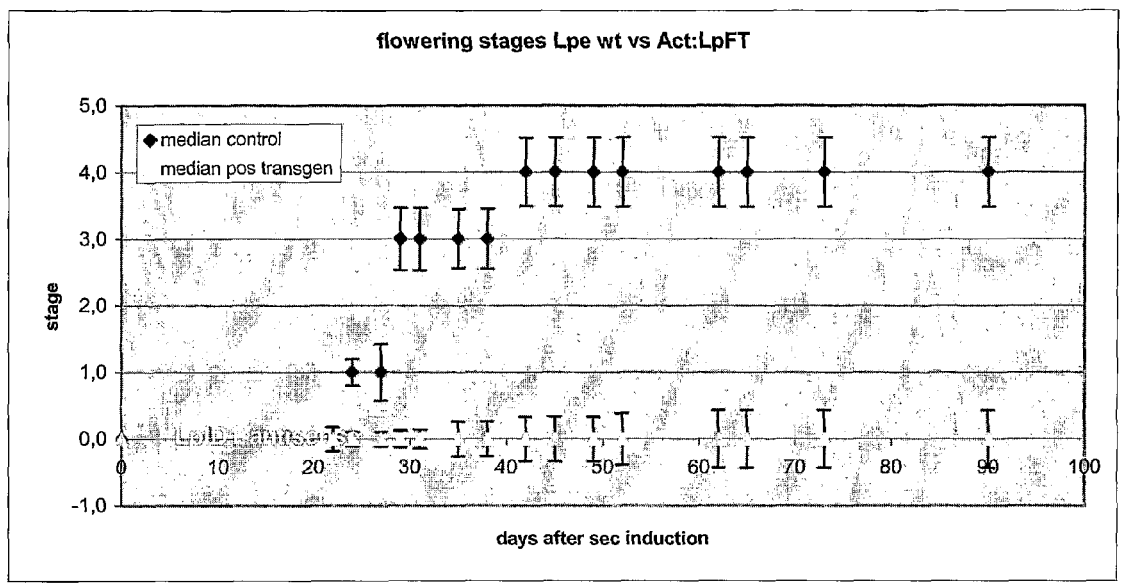

FIG. 8: illustrates progression through flowering stages for control plants and transgenic plants of *L. perenne* constitutively expressing LpFT1 Transgenic *L. perenne* plants expressing LpFT1 under control of the rice actin1 promoter were produced and characterised for transgene expression by RT-PCR. Control plants (wt or Act1::GUS transgene) and transgenic plants (with detectable transgene expression, yet unrespective of expression level) were vernalized and stage progression through flowering (0=non flowering, 1=elongating stem, 2=leaf sheath, 3=flower emerged, 4=anthesis) was monitored upon shift to LD conditions.

Figure 9:
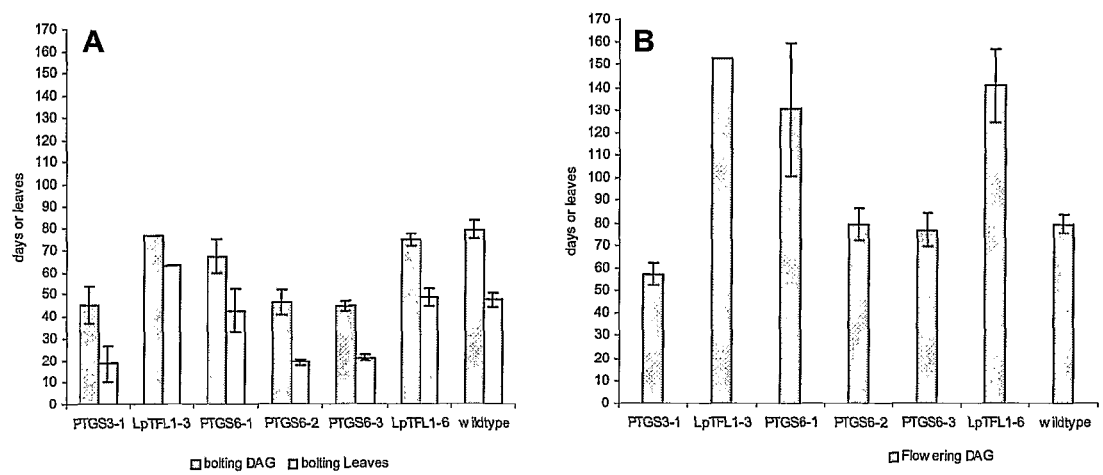

FIG. 9: illustrates the number of days after germination (DAG) (or leaves produced) to bolting (A) and flowering (B) of the PTGS lines, the LpTFL1 background lines and the wildtype under SD conditions.

Figure 10:
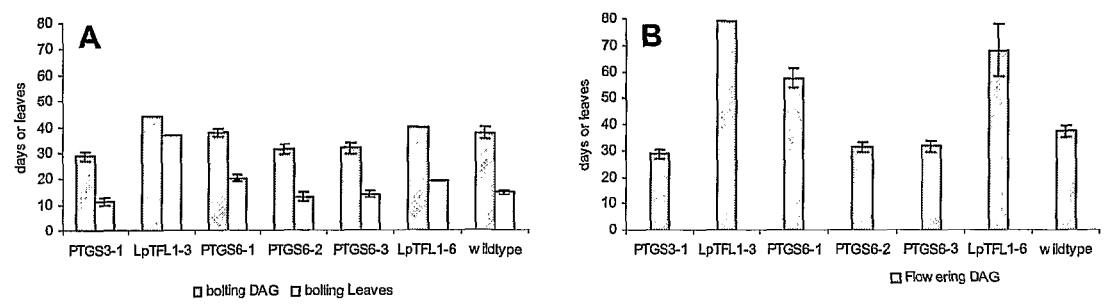

FIG. 10: illustrates the number of days after germination (DAG) (or leaves produced) to bolting (A) and flowering (B) of the PTGS lines, the LpTFL1 background lines and the wildtype under LD conditions.

Figure 11:
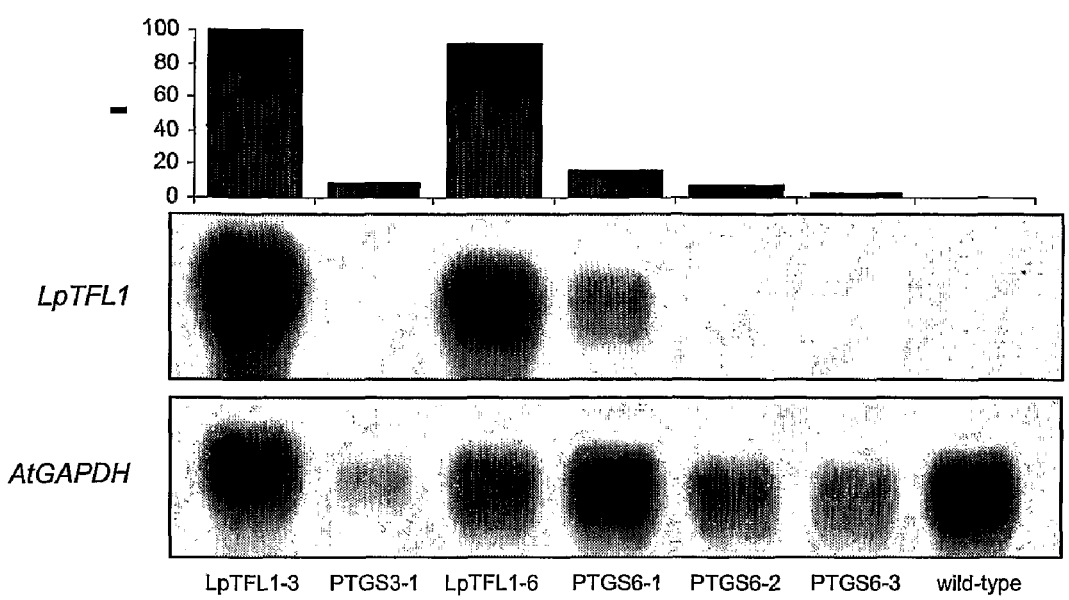

FIG. 11: illustrates an RNA gel blot analysis of the PTGS lines, the LpTFL1 background lines and the wild-type. 2.5 µg of poly-A+ mRNA each line were blotted and probed with a 250 bp LpTFL1 or a 330 bp AtGAPDH cDNA probe. The top graph illustrates the levels of LpTFL1 mRNA relative to the level of AtGAPDH, and the highest detected value was set to 100 (line LpTFL1-3).

Figure 12:
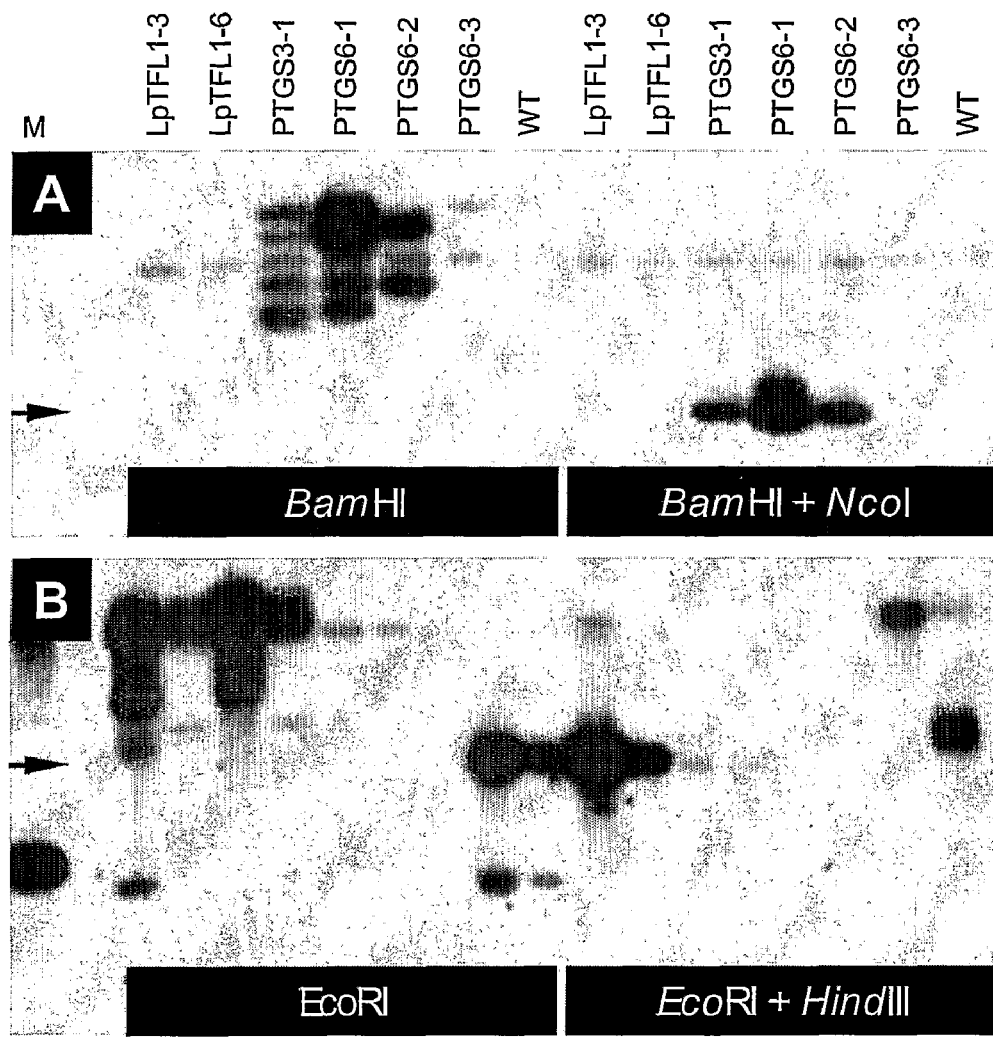

FIG. 12: illustrates a DNA gel blot hybridization analysis of genomic DNA isolated from the PTGS lines, the LpTFL1 background lines and the wildtype. DNA samples of 5 µg were restricted with BamHI and BamHI in combination with NcoI, (A), or with EcoRI and EcoRI in combination with HinDIII (B). Blot A was probed with a 950 bp fragment containing the RNAi intron, LpTFL1-PTGS, and part of the 35S terminator. Blot B was probed with a 0.4-kb fragment containing the 3'-end of the ubiquitin intron and the 5'-end of the LpTFL1 coding region. BamHI together with NcoI releases a 2.4-kb fragment containing the entire 35S::LpTFL1-PTGS cassette (arrow). BamHI has a single restriction site within the T-DNA borders of the 35S::LpTFL1-PTGS cassette. EcoRI together with HinDIII release a 2.8-kb fragment containing the entire LpTFL1 cassette (arrow). EcoRI has a single restriction site within the T-DNA borders of the UBI::LpTFL1 cassette.

FIG. 13: illustrates the ethanol inducible self-maintaining loop.

Schematic drawing of the different elements of the ethanol inducible self-maintaining loop. A: The loop is inactive, because the artificial alcA-minimal35S promoter with 434 operator sequences is repressed by the constitutive expression of the 434-repressor protein. The AlcR regulator protein is inactive without ethanol. B: An ethanol pulse activates the *AlcR transcription factor, which binds to the alcA promoter and overcomes repression by the* 434-repressor resulting in the production of 434/VP16 activator protein and the production of the gene of interest. C: The produced 434/VP16 activator protein in part B under ethanol induction binds to the 434 operator sequences in the alcA-minimal35S promoter with 434 operator sequences and activates its own expression in a self-maintaining loop. Part of the activator will activate the cassette with the gene of interest. The self-maintaining loop will be stopped during meiosis and in the gametophytes the loop is still shut down. The loop gets activated again by a second round of ethanol induction.

Figure 14:

FIG. 14: illustrates *Brachypodium distacyon* transformed with plasmid G10 and G12. Shown is leaf material from two independent transgenic *Brachypodium* lines expressing the plasmid G10 (minimal 35S promoter with one 434 operator element fused to GUS) or two independent lines transformed with G12 (like G10 plus a gene cassette expressing the 434/VP16 activator under the control of the rice actin promoter).

No blue GUS staining is visible in the G10 transformed lines, because the 434/VP16 activator is missing and the minimal promoter with 434 operator elements is not leaky.

However, if 434/VP16 activator protein is present like in transgenic lines transformed with G12, GUS expression is visualized by blue staining.

FIG. 15: shows the alcA promoter sequence with the two 434 $O_R2$ operator sequences (bold and underlined).

Figure 16:
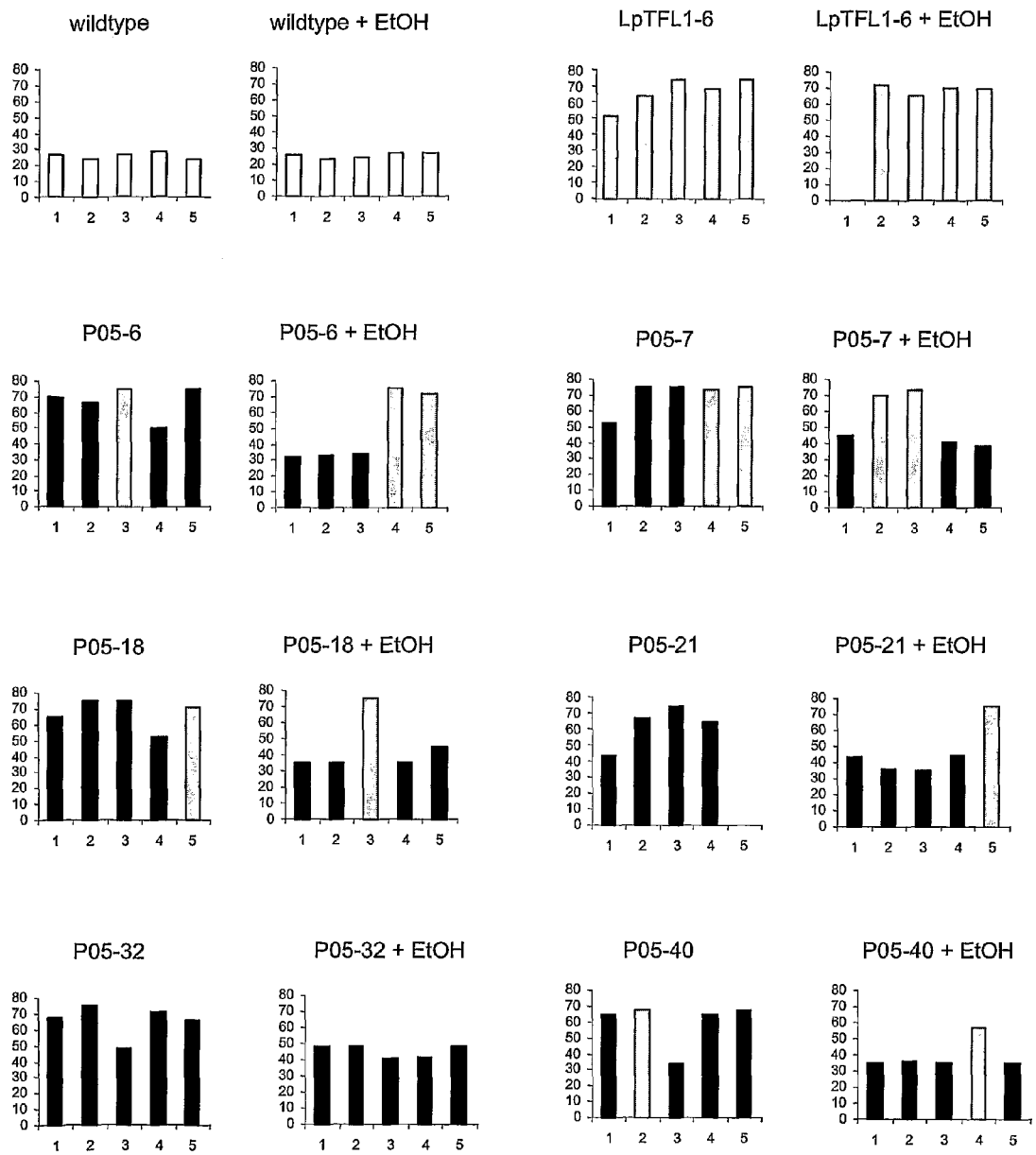

FIG. 16: illustrates the number of days to flowering of the P05 lines, the LpTFL1-6 background lines and the wild-type (white bars) in response to ethanol vapour induction. Gray bars indicate plants, which were PCR-positive only for the UBI::LpTFL1 cassette and black bars indicate plants, which were PCR-positive for both the UBI::LpTFL1 cassette and the P05 construct.

FIG. 17: illustrates the phenotypes of P05 line 18 (A), the LpTFL1-6 background line (B), and the wild-type (C) in response to ethanol vapour induction.

Figure 18:
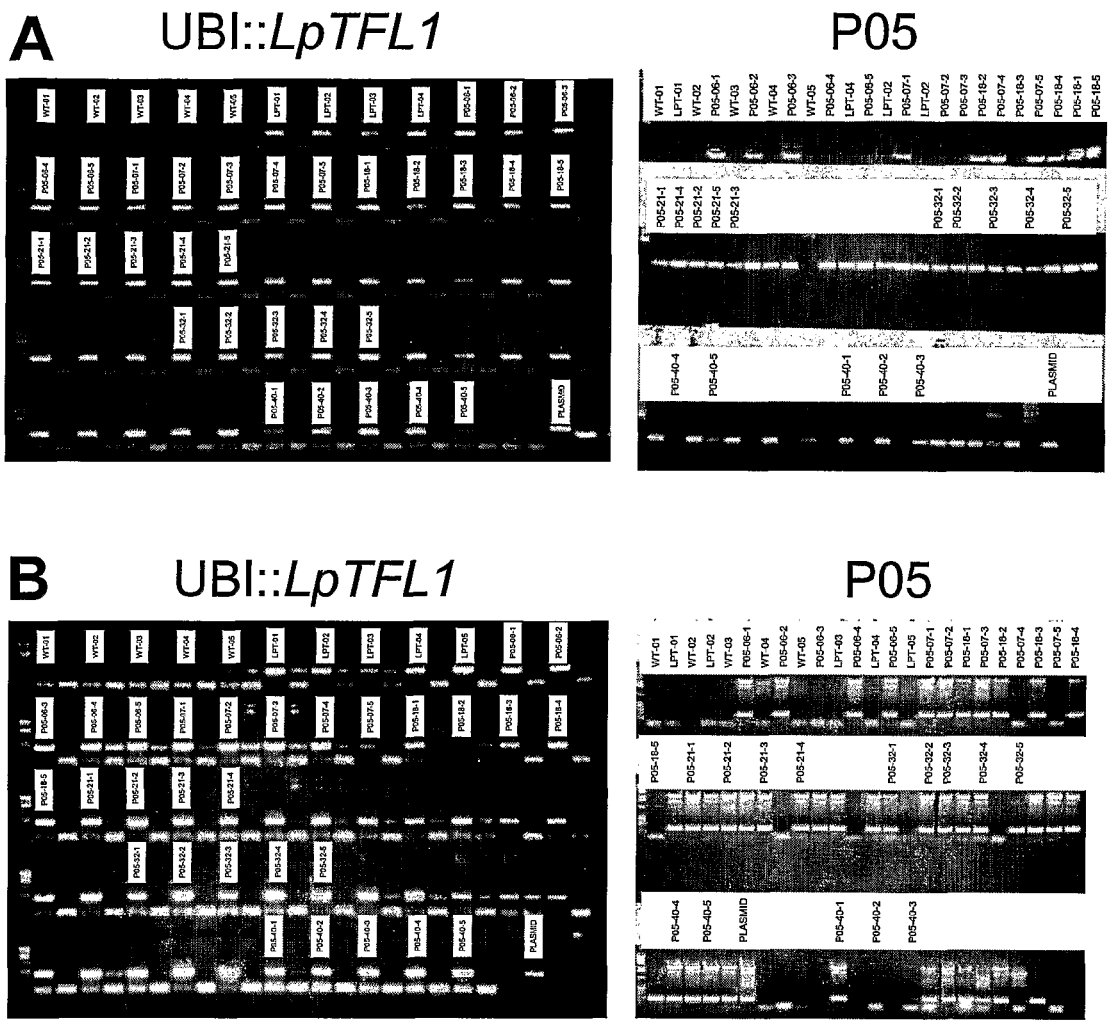

FIG. 18: illustrates the results of the PCR test for presence of the UBI::LpTFL1 cassette and the P05 construct in the ethanol induced (A) and un-induced plants (B).

Figure 19:
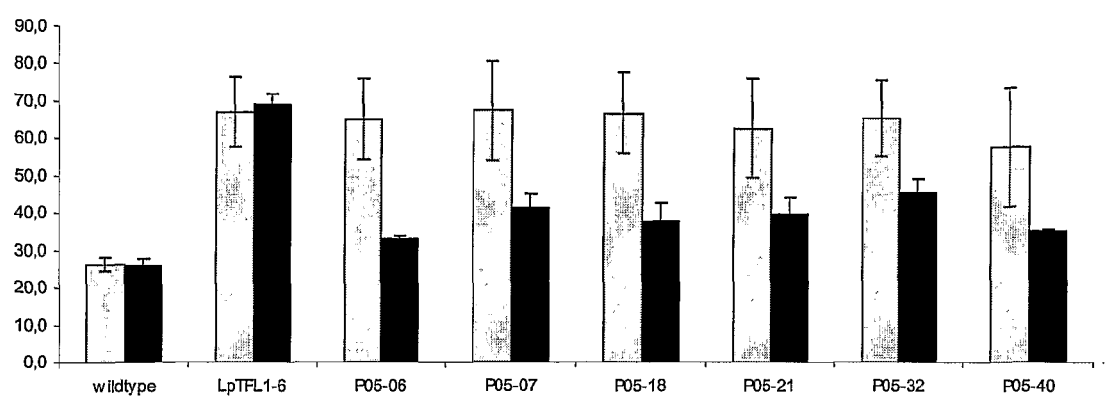

FIG. 19: illustrates the average number of days to flowering of the P05 lines, the LpTFL1-6 background lines and the wild-type in response to ethanol vapour induction. Gray bars indicate un-induced plants and black bars indicate ethanol-induced plants.

Figure 20:
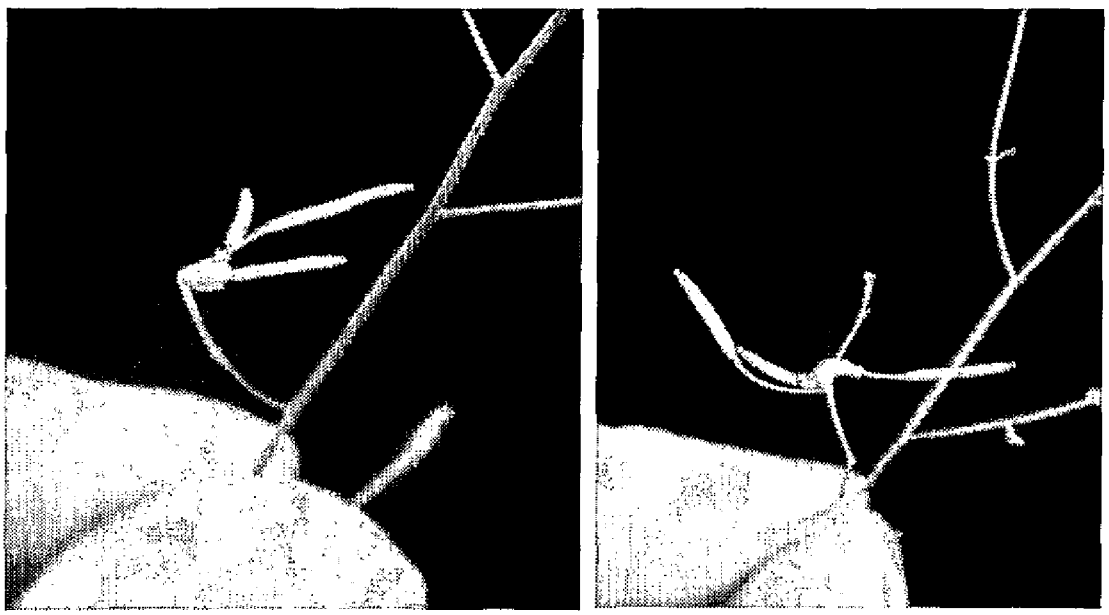

FIG. 20: illustrates two examples of floral revertance in ethanol-induced P05 plants.

Figure 21:
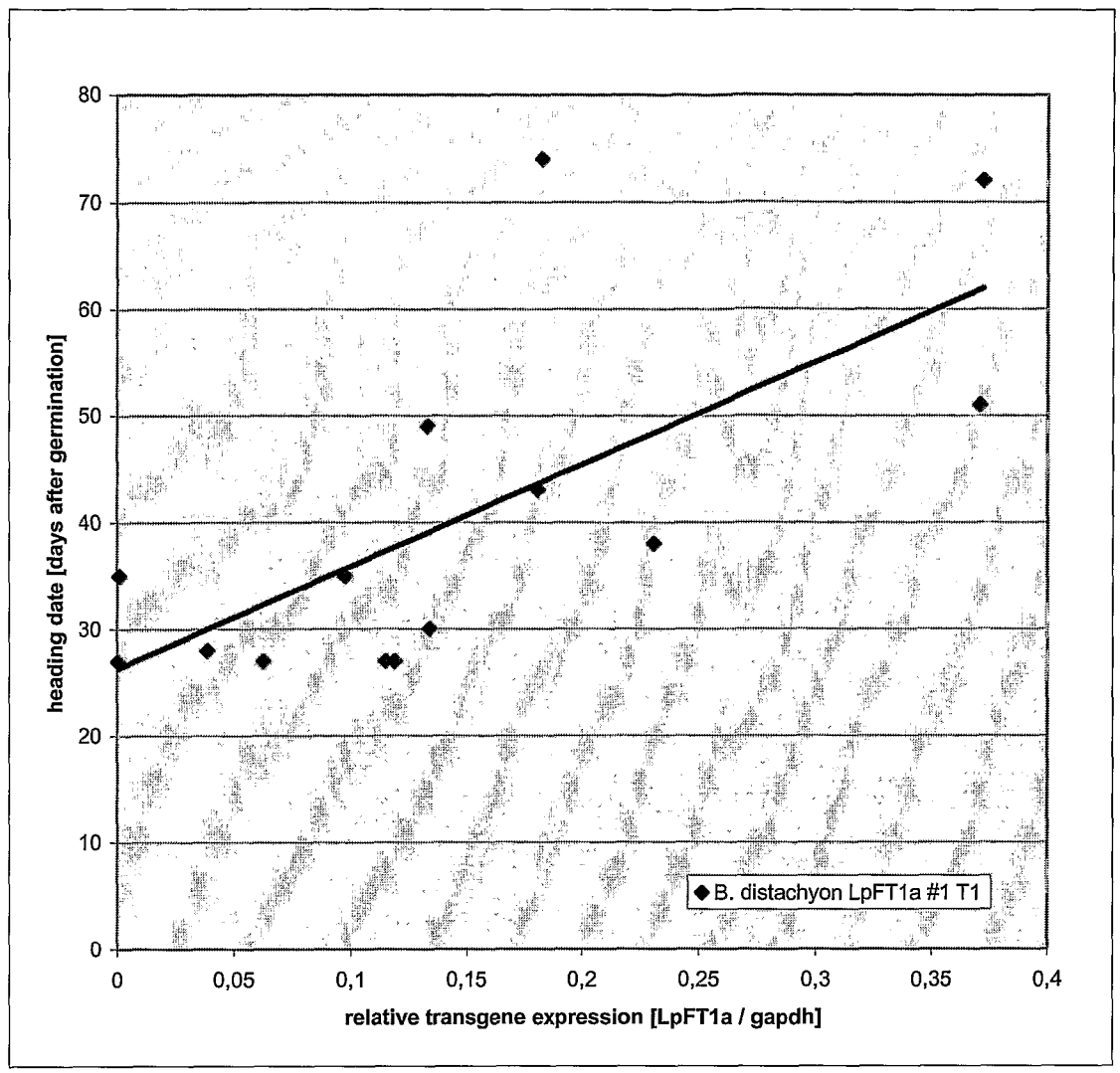

FIG. 21: illustrates the correlation between LpFT1 transgene expression and heading date in transgenic T1 offspring of B. distachyon. The figure shows the comparison between heading date and LpFT1-transgene expression in 14 transgenic offspring plants of one of the lines with highest LpFT1 transgene expression. Strong transgene expression resulted in substantial delay in heading date FIG. 21: illustrates the correlation between LpFT1 transgene expression and heading date in transgenic T1 offspring of B. distachyon. The figure shows the comparison between heading date and LpFT1-transgene expression in 14 transgenic offspring plants of one of the lines with highest LpFT1 transgene expression. Strong transgene expression resulted in substantial delay in heading date FIG. 22: illustrates the phenotypic difference between wt control plants of B. distachyon and transgenic plants constitutively expressing LpFT. Transgenic plants display a substantial delay in heading date and extensive branching.

MATERIALS AND METHODS

The following materials and methods were used in the Examples:

1. RNA Extraction and mRNA Purification

Lolium perenne L. (Tetramax variety) were grown as described earlier (Jensen et. al., Plant Physiol. 125 (2001), 1517-1528). Plants were vernalization at short day (8 hours of light) below 5° C. for at least 12 weeks. Following vernalization, plants were grown under 16 hours of light at 22° C. and 18° C., day and night temperature, respectively, for secondary induction. RNA was extracted from various tissues using the FastRNA Green Kit supplied by BIO101, Inc. (Vista, Calif., USA) according to the manufactorer's recommendation. Total RNA samples were treated with RNase-free DNaseI to remove residual DNA, and mRNA was purified from total RNA using Dynabeads Oligo (dT)$_{25}$ from DynaI (N-0212 Oslo, Norway).

2. Sequencing

Isolated cDNA clones were sequenced using the Big Dye Terminator Cycle Sequencing Ready Reaction Kit (Perkin-Elmner Applied Biosystems, Foster City, Calif., USA) and an ABI PRISM 377 DNA sequencer (Perkin-Elmner Applied Biosystems). Upon sequencing, the isolated by comparison with nucleotide sequences in the National Center for Biotechnology Information (www.ncbi.nim.nih.gov) database with the BLASTN search program were used as probes to screen a shoot apex cDNA library in order to obtain full-length clones.

3. Quantitative RT-PCR Analysis

Single-strand cDNA was transcribed from mRNA isolated from 5 μg total DNA-free RNA using Superscript II reverse transcriptase (Gibco-BRL) according to the manufacturer's instructions. An aliquot of 1/50 of the RT reactions was applied for PCR amplifications performed in a quantitative Rotorgene 2000 system (Corbett Research, Sydney, Australia).

SYBR Green I was used as a fluorogenic intercalating dye to quantify the PCR amplification according to the manufacturer's protocol. Each 20 μl reaction contain 3.5 mM $MgCl_2$, 1×PCR buffer, 0.5 μM of each primer, 10 μM dNTPs, 0.5× SYBR Green I, 0.2 U Taq polymerase (Life Technology) and 1/50 of template cDNA. No template controls (NTC) were run to determine contamination and level of primer dimer formation. PCR parameters were: an initial denaturing step at 94° C. for 60 sec, followed by 40 cycles of 94° C. for 15 sec, 55° C. for 20 sec, and 72° C. for 30 sec. The following primers were used:

```
LpMADS1-fwd:
5'-CAGCTCGCACGGTGCTTC-3'      (SEQ ID NO: 24)

LpMADS1-rev:
5'-GAAACTGAGCAGAACAGA-3'      (SEQ ID NO: 25)

LpMADS2-fwd:
5'-CTTCATGATGAGGGATCA-3'      (SEQ ID NO: 26)

LpMADS2-rev:
5'-AGGTACGTACACCAGCAT-3'      (SEQ ID NO: 27)

LpMADS3-fwd:
5'-GAGCAGACGAATGGAGCA-3'      (SEQ ID NO: 28)

LpMADS3-rev:
5'-ACTGATGGTGCGGAGCAT-3'      (SEQ ID NO: 29)

LpMADS10fwd:
5'-ATTACCCTGCAGTGCGT-3'       (SEQ ID NO: 30)

LpMADS10rev:
5'-AGTACCATAGGTACATGGA-3'     (SEQ ID NO: 31)

LpMADS14fwd:
5'-ATGGCGGGGAAGAGGGAGA-3'     (SEQ ID NO: 32)

LpMADS14rev:
5'-TCACTTTGAGTTGAAAAGTG-3'    (SEQ ID NO: 33)

LpMADS16fwd:
5'-CAATGACGACGGTTCTGA-3'      (SEQ ID NO: 34)

LpMADS16rev:
5'-GCAGACTTAACGATGACA-3'      (SEQ ID NO: 35)

LpGAPDH-fwd:
5'-CAGGACTGGAGAGGTGG-3'       (SEQ ID NO: 36)

LpGAPDH-rev:
5'-TTCACTCGTTGTCGTACC-3'      (SEQ ID NO: 37)

LpACTIN1-fwd:
5'-GAGAAGATGACCCARATC-3'      (SEQ ID NO: 38)

LpACTIN1-rev:
5'-CACTTCATGATGGAGTTGT-3'     (SEQ ID NO: 39)

LpFT1fwd1:
5'-AGCATCAACAGATGATAGCT-3'    (SEQ ID NO: 75)

LpFT1rev:
5'-TGATACAGCACCAGCACGA-3'     (SEQ ID NO: 76)
```

```
-continued
LpFT1fwd2:
5'-TCGTGCTGGTGCTGTATCA-3'    (SEQ ID NO: 77)

rbs rev:
5'-AAGGTGGGAGACATCATCGA-3'   (SEQ ID NO: 78)
```

For each set of primers the reading temperature was determined by melting analyses and fluorescence data were acquired at 87° C. Standard curves were generated for each primer set with plasmid DNA harbouring the corresponding cDNA template. Four 100-fold serial dilutions covering a range from 1 ng to 1 fg of the plasmids were used to determine the standard curves. PCR reactions were performed in triplicate and normalized relative to the initial template amount in each sample estimated by the expression levels of the housekeeping genes LpGAPDH or LpACTIN1, and the level of the MADS-box fragments are presented relative to the level of the LpGAPDH or LpACTIN1 fragments.

4. Test of ETOH-Inducible GUS Expression

Callus cultures of *Festuca rubra* were co-bombarded with pUIRN-AGS (kindly provided by P. Thomsen, Syngenta, Jealott's Hill, Maidenhead, UK) and pAHC20, a selection construct with maize ubiquitin promoter fused to the BAR gene for selection with Bialaphos (kindly provided by P. Quail, Dept. of Biology, George Mason University, Fairfax, Va. 22030, USA). Plants were selected in vitro with 4 mg/l Bialaphos and transferred to soil. Plants were screend by PCR for having the GUS gene using primers 1782-56-5' 5'-GAC TGG CAT GM CTT CGG T (SEQ ID NO: 40) and t35Srev 5'-TAT CTG GGA ACT ACT CAC ACA (SEQ ID NO: 73) and for the AlcR gene AlcR-2377-5' 5'-CM TTT CTG GGC AGG MG TC (SEQ ID NO: 41) and tNOS-63-60-3' 3'-CAT CGC MG ACC GGC MC (SEQ ID NO: 42). Plants that were negative for one or both primer sets were discharged, plants that were positive for both were selected for GUS staining and for RT-PCR test.

For two plants of each of 22 independent transformants and two non transgenic control plants the following induction experiment was made: Non-induced: From each plant, two tillers were cut directly into a standard X-GLUC buffer supplemented with 300 mg/l cyclohexamide, vacuum infiltrated in a speed-vac for 5 min and incubated at 37° C. for 2 nights. Cleared for chlorophyll with 2 times wash in 96% ethanol. Ethanol induction: Tillers were cut and placed in ~2 ml dH$_2$O. For each tube, the volume was doubled with a 4% ethanol solution giving a ~2% ethanol solution in the tubes. All tubes were placed in a plastic bag and a beaker with a tissue cloth soaked in 4% ethanol. The bag was sealed and placed in a growth chamber with a 16 hours light period for 2 nights. Tillers were then GUS stained as described for un-induced.

5. Plant Transformation

*Lolium perenne*—Biolistic Transformation

Plasmids containing transgenes of intererst (pGOI) were introduced into *Lolium perenne* together with pAHC20 (Christensen and Quail, Transgene Research 5 (1996), 213-218) harboring the Bar gene, which confers resistance to the herbicide BASTA®. For particle bombardment highly embryogenic callus induced from meristems or mature embryos was used. Isolated embryos and meristems were cultured on a MS-based ((Murashige and Skoog, Physiol. Plant. 15 (1962), 473-497) callus induction medium (CM) containing 3% sucrose, 4 mg/l 2,4-dichlorophenoxyacetic acid (2,4-D), 100 mg/l casein hydrolysate and 0.3% (w/v) gelrite (Kelco) for 12-26 weeks in the dark at 23° C. Calli were maintained by subculturing every third week on fresh CM-medium. Prior to bombardment, an osmotic pre-treatment for 4 hours were given by transferring small calli (2-4 mm) to a solid MS-based medium supplemented with 3% sucrose, 3 mg/l 2,4-D, 0.25 M sorbitol, 0.25 M mannitol and 0.3% w/v Gelrite. Bombardment was performed with a particle inflow gun (Finer et al., Plant Cell Rep. 11 (1992), 323-328) according to the optimized protocol described by Spangenberg et al. (J. Plant Physiol. 145 (1995), 693-701) with a few modifications: bombardment pressure was 8 bar and 300 :g gold particles 0.6 :m (Biorad) was coated with 0.6 :g plasmid DNA (pGOI and pAHC20 at a molar ratio of 2:1) according to Vain et al. (Plant Cell Tissue and Organ Culture 33 (1993), 237-246). The following day, calli were transferred to CM-medium supplemented with 4 mg/l bialaphos (Meiji Seika Kaisha, LTD, Tokyo) and grown at 23° C. under 16 hrs light. Selection at three weeks interval was performed until vigorously growing callus was obtained. Putative transgenic plants were regenerated by transferring calli to hormon free medium RM (MS-medium containing 3% sucrose and 4 mg/l bialaphos). Rooted plantlets were transferred to screening for stable transformation, putative transgenic plants were sprayed twice (two successive days) with a 0.5% solution of BASTA (Hoechst Schering AgrEvo A/S, Germany) supplemented with 0.1% Tween 20. The number of herbicide tolerant plants was scored after one week. Leaf material from BASTA-resistant plants was subsequently screened for the presence of pGOI by PCR. soil and grown to maturity under greenhouse conditions.

*Brachypodium Distachyon*—Agrobacterium Mediated Transformation

The embryos are placed on callus inducing media to initiate cell proliferation prior to transformation. After one day they were transformed with AGL1 harbouring the respective constructs and co-cultivated with *Agrobacteria* on callus medium for 5 days in the light. Embryos were washed in water supplemented with 250 mg/l Augmentin and drained on sterile filter paper. Selection was carried out on callus medium containing 5 mg/l bialaphos and 250 mg/l augmentin for two periods of ~3 weeks followed by one or two periods of ~2-3 weeks on selective regeneration medium inducing shoots. Green shoots were transferred to rooting medium for ~3 weeks and plants were potted and grown to maturity. Leaves were stained for GUS-expression as described elsewhere.

Callus medium: 4.4 g/l LS salts, 30 g/l maltose, 2.5 mg/l 2,4-D, 8 mg/l agar, pH 5.9, regeneration medium: 4.4 g/l LS salts, 30 g/l maltose, 0.2 mg/l BAP, 8 g/l agar, pH 5.9, rooting medium: 2.2 g/l LS salts, 30 g/l maltose, 8 g/l agar, pH 5.9.

6. LpTFL1 PTGS-Mediated Restoration of Flowering in Late-Flowering UBI::LpTFL1 *Arabidopsis*

Plant Transformation

A 143 bp fragment of LpTFL1 (sequence XX) was amplified from a plasmid pLPTFL1 (Jensen et al., Mol. Breeding 13 (2004), 37-48) containing the LpTFL1 coding region by PCR using recombinant pfu DNA polymerase in combination with the primers LpTF1rnai5' (5'-CACCGTGGAGCCTCT-TATTGTTGGT-3' (SEQ ID NO: 43)) and LpTFL1rnai3' (5'-TAGATACMCTGCTGATGGGTA-3' (SEQ ID NO: 44)). The fragment was cloned into pENTR™/SD/D-TOPO® (Invitrogen, Carlsbad, Calif., USA) to give pENTR-LpTFL1-PTGS, which was subsequently used in a LR-recombination (Invitrogen, Carlsbad, Calif., USA) to recombine the LpTFL1-PTGS fragment into the destination vector pK7GWIWG2(I) (Karimi et al., Trends in Plant Science 7 (2002), 193-195). The resulting plasmid, pK7-LpTFL1-PTGS possesses a streptomycin and/or spectinomycin resistance gene for plasmid selection and harbors the nptII gene for plant Kan$^r$ selection. Transgenic *Arabidopsis* plants expressing LpTFL1 from the ubiquitin promoter (line 3 and 6, T2 generation, Jensen et al., Plant Physiol. 125 (2001), 1517-1528) were transformed with the *Agrobacterium tumefaciens*, strain PGV3101 (Koncz and Schell, Mol. Gen. Genet. 204 (1986), 386-396) harboring the pK7-LpTFL1-PTGS using the floral dip method described by Clough and Bent (Plant J. 16 (1998), 735-743).

7. Growth Conditions

T1 transformants were selected on MS-pates (Murashige and Skoog, 1962, loc. cit.) supplemented with 50 mg/l Kan$^r$ (pK7-LpTFL1-PTGS) and 2 mg/l Bialaphos (Shinyo Sangyo Ltd, Japan) and grown in long day (LD conditions, 16 hrs. light) at 22° C. Early flowering lines were selected and selfed for T2 flowering time analysis. Kan$^r$, Bialaphos resistant T2 plants were stratified at 4° C. for four days and then grown in soil in short day (SD; 8 hrs light) conditions at 22° C. After three weeks half of the plants were moved to LD conditions. All lines were grown alongside the UBI::LpTFL1 line 3 and 6 and the wildtype (Col. 0) for control. Flowering time was measured as the number of days or leaves to bolting and to the opening of the first flower.

8. DNA Gel Blot Analysis

Genomic DNA for the gel blot analysis was isolated from the T2 LpTFL1-PTGS plants (hereafter referred to as PTGS-lines) and the UBI::LpTFL1 line 3 and 6 (hereafter referred to as LpTFL1-3 and LpTFL1-6, respectively) and the wild-type by the Phytopure® Genomic DNA isolation system (Nucleon). DNA (5 µg) were digested overnight with restriction endonucleases EcoRI, EcoRI in combination with HindIII (plasmid pLpTFL1) and BamHI, BamHI in combination with NcoI (plasmid pK7-LpTFL1-PTGS). It was fractionated on a 0.8% agarose gel and blotted onto Amersham Hybond N membrane in 20% SSC according to the manufacturer's recommendations. A 950 bp fragment containing the RNAi intron, LpTFL1-PTGS, and part of the 35S terminator was amplified by PCR using the primers INT#185 (5'-TAGGGGTTTAGATGCMCTGT-3' (SEQ ID NO: 45)) in combination with T35Srev (5'-TATCTGGGAACTACTCACACA-3' (SEQ ID NO: 46)) on plasmid DNA and used as probe for the detection of transgenes corresponding to pK7-LpTFL1-PTGS. A probe for the detection of transgenes corresponding to pLpTFL1 was generated in a similar way using the primers ACT#56 (5'-TATTTATTTGCTTGGTACTG-3' (SEQ ID NO: 47)) together with LpTFL1ins3' (CTCCCCCCCAAATGMGC-3' (SEQ ID NO: 48)). Both probes were radiolabeled with β-$^{32}$P-labeled dCTP (3,000 Ci/mmol) through the random primer method (Megaprime, Amersham) and hybridized to the blots containing the respective DNA digestions.

9. RNA Gel Blot Analysis

Seventy five micrograms of total RNA were isolated from the T2 PTGS plants and the LpTFL1 lines and the wild-type using the Trizol® reagent (Invitrogen, Carlsbad, Calif., USA) according to the manufactors instructions. Purified poly-A+ mRNA (Dynabeads, DYNAL, Norway) from one individual of each line was fractionated under denaturing conditions and transferred onto Hybond N membranes in 20% SSC. The membranes were hybridized to a 250 bp LpTFL1 cDNA fragment, Which was amplified by PCR using the primer LpTFL1ins5' (5'-GACCTTATTCACATTGGTTATG-3' (SEQ ID NO: 49)) in combination with LpTFL1ins3' (outside the PTGS sequence), and a 330 bp AtGAPDH cDNA fragment for standardization. Relative LpTFL1 expression levels in the transgenic lines were estimated on the basis of the results from a density scan (Quantity One software, Biorad) of the autoradiograph and the highest detected value was set to 100.

EXAMPLE 1

Screening of cDNA Clones

An apex cDNA library of *Lolium perenne* L. (variety Green Gold) was constructed from extracted mRNA isolated from shoot apices at different growth stages after floral induction, using the ZAP-cDNA/Gigapackill Gold Cloning Kit (Stratagen, La Jolla, Calif., USA). The cDNA library containing approximately 700,000 independent clones was screened with corresponding $^{32}$P-labeled C-terminal gene probes. The LpMADS1 probe of 149 bp was made by a RT-PCR reaction using mRNA from secondary induced meristems as template and using the degenerate primers:

```
                                        (SEQ ID NO: 50)
Fwd primer = 5'-SARHTGAAGMGGATAGAGAACAAGAT-3', (SEQ ID NO: 51)
Rew primer = 5'-CTCGTAGAGCTTGCCCTTGG-3'.
```

The probe used to isolate LpMADS2 and LpMADS3 was made by a RT-PCR reaction using mRNA from secondary induced meristems as template and using the primers:

```
                                     (SEQ ID NO: 52)
    Fwd primer = 5'-TCGAGAACAAGATCAACCGCC-3', (SEQ ID NO: 53)
    Rew primer = 5'-TGGTGGAGAAGTTGATGAGCC-3'.
```

Isolation of LpMADS10, LpMADS14 and LpMADS16 by 5'- and 3'-RACE.

Purified mRNA derived from 5 µg of DNase-free RNA was used for first-strand cDNA synthesis as described by the manufacturer (Clontech Laboratories Inc.). 5'-RACE was performed with 5'-cDNA from non-induced leaves using a primer designed to be specific for MADS box genes (5'-TTGGAGMGGT(G/C)AC(G/C/T)CGGCT-3' (SEQ ID NO: 54)) and with a nested primer (5'-GTTCTC(A/G/T)AT(C/T)CGCTT(G/C)A-3' (SEQ ID NO: 55)). 3'-RACE was performed with 3'-cDNA with 3'-RACE primer (5'-GCCG(A/G/C)CA(AG)GT(G/C)ACCTTCTTCC-AA-3' (SEQ ID NO: 56)) and nested primer (5'-GC(G/C/T)CT(C/T)(A/C)TCGTC(G/T)TCTC-3' (SEQ ID NO: 57)). To isolate full-length MADS-box genes from the 5'-RACE, primers were designed in the UTR of the fragments generated in the 5'-RACE (group1-5' primer: 5'-ACCGCAGCCACCATCTCAC-CTCA-3' (SEQ ID NO: 58); group2-5' primer: 5'-CCTCTCGCCACCACCACCAGA-3' (SEQ ID NO: 59); group3-5' primer: 5'-TGCTCCTGAT-TGGTCCACAGTTC-3' (SEQ ID NO: 60)) and the 3'-RACE primer was used as the nested primer. Primers were also designed from the 3'-RACE fragments (group1-3' primer: 5'-GAGTTGTCGT-MCCAGCAGCATCACT-3' (SEQ ID NO: 61); group2-3' primer: 5'-AACATCACGTCATGCAGCCACMGGAT-3' (SEQ ID NO: 62); group3-3' primer: 5'-ATGGGACCATTC-CAGTCAGTCTAGCT-3' (SEQ ID NO: 63)) and the 5'-RACE primer was used as the nested primer. PCR parameters were an initial denaturing at 94° C. for 60 sec, followed by 30 cycles of 94° C. for 30 sec, 68° C. for 30 sec and 72° C. for 3 min.

Isolation of LpMADS10 by Yeast Two-Hybrid Screen:

A fusion library in a GAL4-activation domain vector (Matchmaker system from Clonetech, pACT2) of cDNA isolated from Lolium perenne flowers was generated and 3.6× 10$^6$ colonies were screened in a Two-Hybrid assay with a fusion of the LpMADS1 K-domain to the GAL4-DNA binding domain. The K-domain of LpMADS1 (corresponding to amino acids 91 to 162) was amplified with the following primers by PCR (primer A (SEQ ID NO: 79): gcggatccggtgtcatgaatatag; primer B (SEQ ID NO: 80): gcgtcgaccagtgacctctccttc), gel purified and BamHI/SalI cloned into the pAS1 vector (Durfee et al., Genes Dev. 7 (1993), 555-569). Analysis of this Two-Hybrid screen in yeast identified a specific interaction of MADS1 and a novel MADS-box gene (Sequence ID NOS: 3-4). The cloned LpMADS10 gene was full-length.

Isolation of the LpID1-Like cDNA Clone

LpID1 was identified essentially by a PCR-based strategy. An initial strategy using the maize full-length ID1 to screen cDNA libraries for Lolium homologs led to a high number of candidates, which by sequencing showed poor homology to the maize ID1 outside the zink finger regions and thus were unlikely to represent ID1 homologs.

An alternative strategy based on the maize ID1 polypeptide was developed, in which two consensus primers (identical regions in all obtained *Lolium* clones) in the two zink finger regions were designed and degenerated primers based on the very C-terminal part of the maize ID1 protein. By running the lower primer—TCCTGGAGCCACMCTTCTAG (SEQ ID NO: 21)—(last 7 aa of the maize ID1) on $1^{st}$ strand cDNA made from young leaves in a first reaction using upper primer—TTCCAGCGGGACCAGMCC (SEQ ID NO: 22)—in Zink finger region 1 and nesting in a second reaction with upper primer in zink finger region 2—GGATCMGMGCACTTCT (SEQ ID NO: 23)—a 700 bp fragment representing a likely partial ID1 homolog was obtained. 5'-RACE was used to extent the fragment from zink finger region 2 to the upstream zink finger region 1 and finally isolation and sequencing of a genomic clone provided the missing 5'-part. Finally, knowing the full-length sequence a full-length ID1 open reading frame (ORF) was produced by PCR and confirmed by sequencing.

In contrast to the LpID1 gene described herein, the homologoues of maize ID1 isolated from perennial ryegrass disclosed in WO 02/38768 are only distantly related to the maize ID1 outside the Zink Finger regions. Blast search results against public sequence databases including Genbank reveal that the LpID1 of the present invention represents the closest relative to the maize ID1 in comparison to any publicly available nucleotide or polypeptide sequence.

Isolation of the LpFT-Like cDNA Clone

Purified mRNA derived from 5 µg of DNase-free RNA was used for first-strand cDNA synthesis as described by the manufacturer (Clontech Laboratories Inc.).

5'-RACE and 3'-RACE was performed using the primers:

```
UPM long:
                                                    (SEQ ID NO: 64)
5'-CTA ATA CGA CTC ACT ATA GGGCAA GCA GTG GTA TCA
ACG CAG AGT-3'

3lpFT-1
                                                    (SEQ ID NO: 65)
5'-CTA CGA GAG CCC AAR GCC AAM CAT-3'

3lpFT-2
                                                    (SEQ ID NO: 66)
5'-AGC AAC ACA TCC TTG TGA AGG CCC A

3lpFT-3
                                                    (SEQ ID NO: 67)
5'-AGC TAA GTA CCG TGT GAT GCG GCT
```

```
3lpFT-4
                                                    (SEQ ID NO: 68)
5'-TGG CGG CGA CGG GCT TTC CGA
```

In particular, a cDNA library was made from a pool of *L. perenne* leaves harvested throughout 24 h in long day conditions. Messenger RNA was isolated from total tissues using Dynabeads Oligo $(dT)_{25}$ (Dynal). A single-strand cDNA synthesis was performed with the PowerScript™ Reverse Transcriptase according to the SMAR™ RACE cDNA Amplification kit (Clontech Laboratories Inc). A 3'-RACE PCR with primer 3lpFT-1 was performed on a cDNA library following manufacturer's instructions. A 560 bp sequence was isolated which showed high homology to the rice OsHD3a sequence. To obtain the full-length cDNA of the LPFT-like 1 gene, a 5'-Race PCR was done with primer 3lpFT-2 designed on the 3'end. In total a full-length 842 bp sequence was isolated and identified as a likely LpFT-like homolog.

Isolation of the LpCO cDNA Clone

To isolate CO-like genes from *Lolium perenne*, a set of degenerated primers were designed based on nucleotide sequence comparison between AtCO and OsHd1. A cDNA library (Stratagene) made from *L. perenne* leaves, which had been induced for flowering was used as template. PCR was performed with primers LpCO-fwd1: GGGAGCGAGTGTGTGGTAC (SEQ ID NO: 69) and LpCO-rev1:: ACCCTGGCCTCCCTGTC (SEQ ID NO: 70) with 0.5 µg of template with 2 mM $MgCl_2$, 1×PCR buffer, 0.4 µM of each primer, 0.25 mM dNTPs and 0.25 U of Taq polymerase (Life Technology) in 50 µl reaction. PCR parameters were: initial denaturation 95° C. 10 min, 35 cycles of 95° C. for 30 sec, 60° C. for 30 sec and 72° C. for 60 sec and 72° C. for 60 sec. A 300 bp PCR fragment was labelled by random labelling (Megaprime DNA labelling system, Amersham Biosciences) and used as a probe to screen 2.0 $10^7$ clones from a ZAP-cDNA phage library (Stratagene) from *L. perenne* (F6) leaves. 5 clones were isolated at low stringency and a unique full-length cDNA clone was isolated representing a CO homologue named LpCO.

A full-length genomic clone of LpCO was obtained by PCR using genomic ryegrass DNA (Fast DNA kit, Q-Biogene) in combination with two primers LpCO-fwd2:: ATGGTCTGTGTGGTGCMGCCA (SEQ ID NO: 71)/LpCO-rev2:: ACCGATCTACCTGAACTGCTTG (SEQ ID NO: 72) which match the sequence the in 5' and 3'UTR respectively. PCR reaction was performed on 0.5 µg gDNA template with 2 mM $MgCl_2$, 1×PCR buffer, 0.4 µM of each primer, 0.25 mM dNTPs and 0.25 U of Taq polymerase (Life Technology) in 50 µl reaction. PCR parameters were: 95° C. 4 min, 30 cycles of 95° C. for 20 sec, 68° C. for 15 sec and 72° C. for 90 sec and 10 cycles of 95° C. for 30 sec, 52° C. for 15 sec and 72° C. for 90 sec.

EXAMPLE 2

Restoration of WT Flowering Phenotype in an *Arabidopsis thaliana* Plant Otherwise Substantially Prevented in Flowering Through the Floral Suppressive Action of the Polypeptide of LpTFL1

In order to restore wild-type flowering time in late-flowering UBI::LpTFL1 *Arabidopsis* plants a construct was made in which a transgene encoding two 143 bp LpTFL1 inverted repeats separated by a spliceable *Arabidopsis* intron was placed under the control of the viral 35S CaMV promoter. The 35S::LpTFL1-PTGS construct was introduced into two different late-flowering transgenic UBI::LpTFL1 *Arabidopsis* lines (line 3 and 6, flowering after 77 and 66 days in LD, respectively). Several Kan', BASTA® resistant T1 plants were regenerated of which one line from background LpTFL1-3 and three from background LpTFL1-6 flowered simultaneously with the wild-type. These four lines (PTGS3-1, PTGS6-1, PTGS6-2, and PTGS6-3) were self-pollinated and the T2 seeds were used for a detailed flowering time phenotype analysis.

The flowering time response of the PTGS lines was determined both under SD and LD conditions and compared with that of the wild-type and the late-flowering LpTFL1-3 and LpTFL1-6 background lines. All the PTGS plants were germinated and selected on MS medium containing kanamycin (50 mg/l) for selection of the 35S::LpTFL1-PTGS construct and bialaphos (2 mg/l) for selection of the UBI::LpTFL1 construct. The LpTFL1 background lines were germinated and selected on MS medium containing bialaphos (2 mg/l) and the wild-type was germinated on MS medium without selection. Flowering time was scored both as the number of days and the number of leaves produced from germination till the opening of the first flower. In the wild-type the first flower opens immediately after bolting but in the late-flowering LpTFL1-3 and LpTFL1-6 lines flowers are first formed several weeks after bolting. Time to bolting was also scored as the number of days and the number of rosette leaves produced.

In LD conditions the wild-type started bolting (and flowering) after about 37 days (FIG. 10A). At this time several of the PTGS plants had already started to flower.

The LpTFL1-3/6 background lines bolted a week later, but remained without flowers for another month (FIG. 10B). Introduction of the LpTFL1-PTGS into the LpTFL1-3 line reduced the time to flowering with 40 days from 79 to 28.8±1.8. A similar pattern was observed for the plants growing under SD conditions although flowering for all plants was considerably delayed compared with the LD grown plants (FIG. 9). The wild-type flowered after about 79 days (FIG. 9B). At this time the PTGS3-1 line had already been flowering for almost fourteen days. The LpTFL1-3 background line however, did not flower before day 150. Thus under SD conditions the presence of the LpTFL1-PTGS construct was associated with a 96 day decrease in the time to flowering in line LpTFL1-3. Two other PTGS lines (6-2 and 6-3) flowered simultaneously with the wild-type and significantly earlier than the LpTFL1-6 background line (64 days). One PTGS line (6-1) did not flower significantly earlier as the LpTFL1-6 background neither in SD nor in LD in the T2 generation.

The LpTFL1RNAi Sequence is Sufficient for Downregulation of LpTFL1 Expression and Floral Eestoration.

RNA gel blot analysis was performed to verify a PTGS-mediated downregulation of LpTFL1transcription in the early-flowering PTGS lines. The RNA blots were probed with a LpTFL1 fragment laying outside the LpTFL1-PTGS sequence in order to avoid any cross-contamination. For standardization the blot was also probed with an AtGAPDH fragment. A significant decrease in LpTFL1 mRNA was detected in the three early-flowering PTGS lines (FIG. 11). The most prominent reduction was observed in line PTGS3-1 and PTGS6-3, where the level of LpTFL1 mRNA was reduced with 91.6% and 90.4% respectively, compared to the background lines.

The presence of the two transgenes (UBI::LpTFL1 and 35S::LpTFL1-PTGS) was tested by DNA gel blot analysis in which genomic DNA from the transgenic lines, the background lines and the wild-type were digested with restriction enzymes that cuts at both T-DNA borders thereby releasing the entire cassettes or only one time in-between the borders to reveal the presence of concatamers and allow a rough prediction of transgene copy number. Digestion of the 35S::LpTFL1-PTGS cassette with BamHI and NcoI releases a fragment of 2.4 kb, which could be detected in all the PTGS lines but not in the LpTFL1 background lines or in the wild-type (FIG. 12A). Digestion of the UBI::LpTFL1 cassette with EcoRI and HindIII releases a fragment of 2.8 kb, which could be detected in all the PTGS lines and in the LpTFL1 lines but not in the wildtype (FIG. 12B). However, the intensity of the bands were markedly reduced in line PTGS6-2 and PTGS6-3. Analysis of the blot containing DNA digested with EcoRI only, revealed that the original integration pattern of UBI::LpTFL1 in the background line LpTFL1-6 had been changed in the PTGS-lines and that line PTGS6-2 and PTGS6-3 only contained a single copy of the UBI::LpTFL1 cassette (FIG. 12B). It is not possible to determine at what stage the excision of the UBI::LpTFL1 cassette has occurred and also not if it can be related to the presence of the LpTFL1-PTGS construct. The integration patterns of UBI::LpTFL1 in PTGS3-1 and PTGS6-1 were identical to their respective background lines. Thus, the reduction in flowering time observed in line PTGS6-1 and the restoration of wild-type flowering observed in line PTGS3-1 is directly linked to a LpTFL1-PTGS mediated post-transcriptional silencing of LpTFL1. This result also shows that the LpTFL1-PTGS sequence is capable of overcoming the effect of multiple UBI::LpTFL1 transgene copies.

In conclusion, it was shown that expression of the LpTFL1-PTGS construct initiates a post-transcriptional silencing of LpTFL1, which eventually will abolish the LpTFL1 repression of flowering in *Arabidopsis*. This result is to the inventors' knowledge the first evidence of PTGS-mediated release of transgene-induced flowering repression. This method will have wide applications for floral restoration and will not be limited to LpTFL1 but also to other floral repressors, such as the LpFT-like gene, the *Lolium perenne* MADS box genes LpMADS10, the LpMADS14, the LpMADS16 or the *Arabidopsis thaliana* Flowering Locus C/-F (FLC/FLF) gene (accession AF537203/AF116527), which may confer floral repression activity.

EXAMPLE 3

Substantial Prevention of Flowering in *Arabidopsis thaliana* Through the Floral Suppressive Action of Expressing the LpFT-Like Polypeptide Blast results of LpFT-like against the NCBI sequence database revealed a close similarity to the FT subfamily of Phosphatidyl Ethanolamine Binding Proteins (PEBS). This is illustrated in FIG. 3 showing the phylogenetic relationship of LpFT-like and other Phosphatidyl Ethanolamine Binding Proteins (PEBS) including the LpTFL1 polypeptide. The LpFT-like polypeptide groups together with the FT-subfamily, being clearly distinctive from the TFL subfamily, thus indicating a floral enhancer activity of the LpFT-like polypeptide. Unexpectedly, the opposite was found to be the case. As illustrated in FIG. 4, expression of the LpFT-like polypeptide in *Arabidopsis thaliana* confers a strong suppression of flowering. *Arabidopsis* Ler and Col ecotypes constitutively expressing the LpFT-like polypeptide (under the control of the 35S promoter) showed indeterminate growth pattern and flowered in average 2-2.5 months after sowing compared to about 3 weeks after sowing for wild type plants. Some of the LpFT-like expressing plants never flowered and died without setting any seeds. These findings are very similar to the phenotype of LpTFL1 expressing plants and thus represent the first demonstration of TFL1-like functionality of a FT-like polypeptide.

The floral suppressor activity of the LpFT-like polypeptide was further demonstrated by crossing of late-flowering LpFT-like expressing *Arabidopsis* plants with late-flowering LpTFL1 expressing plants, as illustrated in FIG. 5. The offspring of these crossings showed an unexpected additive late-flowering effect of the LTFL1 and the LpFT-like polypeptides, the LpTFL1/LpFT-like expressing plants being significant more late flowering than any of the late-flowering LpTFL1 or LpFT-like expressing lines.

EXAMPLE 4

Constitutive Overexpression of LpFT1 Prevents Flowering in Transgenic Plants of *Lolium Perenne*

Transgenic *L. perenne* plants expressing LpFT1 under control of the rice actin1 promoter were produced and characterised for transgene expression by RT-PCR. Control plants (wt or Act1::GUS transgene) and transgenic plants (with detectable transgene expression, yet unrespective of expression level) were vernalized and stage progression through flowering (0=non flowering, 1=elongating stem, 2=leaf sheath, 3=flower emerged, 4=anthesis) was monitored upon shift to LD conditions. Results are shown in FIG. 8. The majority of control plants had progressed through phase 1 within 24 days in LD and had reached phase 4 no later than 42 days after shift to LD. 52 days after shift to LD, 87% of all control plants had progressed through anthesis. In contrast, the gross of plants expressing the transgene never reached phase 1. In fact, 93% of all plants expressing the transgene remained non-flowering during the whole experiment.

This result clearly demonstrates the strong potential of the LpFT1 polypeptide to prevent flowering in the homologous system.

EXAMPLE 5

Constitutive Ectopic Expression of LpFT1 in the Grass Model Species *Brachypodium Distachyon*

In order to demonstrate the potential of LpFT1 to repress the process of flowering in monocots, we used *B. distachyon* as a model system regarded as representative for the Pooidae subfamily. The Pooidea subfamily comprises the tribes Ampelodesmeae, Aveneae, Brachyelytreae, Brachypodieae, Bromeae, Diarrheneae, Lygeeae, Meliceae, Nardeae, Poeae, Stipeae and Triticeae, and thereby the large majority of agronomically important temperate grasses and cereals. Transgenic *B. distachyon* plants expressing LpFT1 from the rice actin1 promoter were produced by *Agrobacterium*-mediated transformation. In the T1 generation, at least 15 seeds were sown for each line and heading dates were monitored as days from germination to ear emergence. Lines were characterised for presence of transgene to distinguish between null segregants and transgenic offspring. Transgene expression was determined in transgenic $T_1$ generation plants using real-time PCR. The results depicted in FIG. 21 show the comparison between heading date and LpFT1-transgene expression in 14 transgenic offspring plants of one of the lines with highest LpFT1 transgene expression. Strong transgene expression resulted in substantial delay in heading date.

Figure 22:
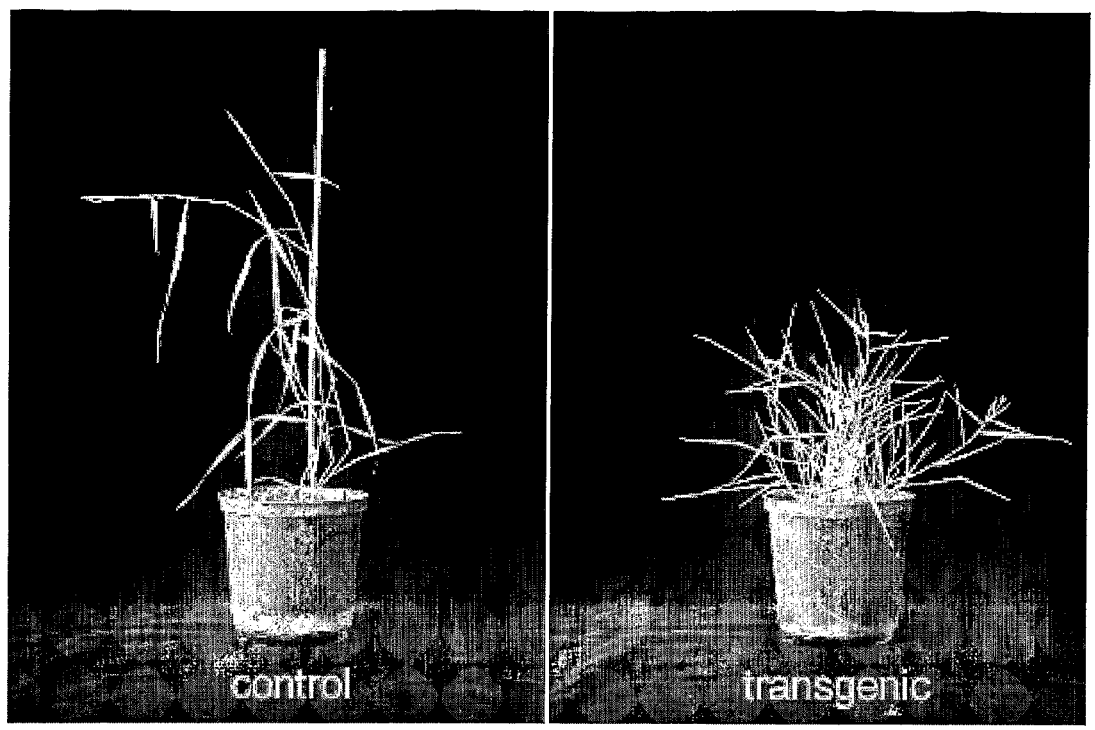

In comparison to control plants, T1 individuals showing high transgene expression exhibited a pronounced branching phenotype as depicted in FIG. 22.

EXAMPLE 6

Gene Expression Profile of LpMADS1, LpMADS2, LpMADS3 in Ryegrass During the Floral Transition The LpMADS1, LpMADS2 and LpMADS3 genes in ryegrass show an expression pattern as predicted for an AP1-like function as enhancer of floral transition. Blast results of LpMADS1, LpMADS2 and LpMADS3 against the NCBI sequence database revealed a close similarity to the AP1 subfamily of MADS box proteins. Homology to AP1-subgroup MADS box proteins/genes from other plant species based on sequence information alone, does not allow determining possible functional conservation. Considering the high degree of redundancy in function found within the MADS box proteins from, e.g., *Arabidopsis* additional information on e.g. expression pattern is required. For an AP1-like floral enhancer function, the expression of LpMADS1, LpMADS2 and LpMADS3 should expectedly increase early in response to floral transitional stimuli.

To determine the expression pattern of LpMADS1, LpMADS2, LpMADS3 message in ryegrass mRNA levels were examined in different tissues by real time quantitative PCR. For all three MADS genes, expression was shown to increase rapidly in the shoot apex upon exposure to 6 weeks of vernalization (see FIG. 1). The expression of LpMADS1 was more strongly induced than were LpMADS2 and LpMADS3. During secondary induction, the expression of all three genes was found to gradually decline to a level higher than found in non-induced (vegetative) plants. In all three cases, the findings together with the sequence similarity support the premise that the three MADS genes represent functional AP1-like floral enhancers with the potential of antagonistically overcoming the suppression of flowering caused by any of the polypeptides LpMADS10, LpMADS14, LpMADS16, LpTFL1 or FLC or a functional fragment, derivative, or homologue thereof.

EXAMPLE 7

Gene Expression Profile of LpMADS10, LpMADS14 and LpMADS16 in Ryegrass During the Floral Transition The LpMADS10, LpMADS14 and LpMADS16 genes in ryegrass show an expression pattern as predicted for an inhibitor of floral transition.

To determine the expression pattern of LpMADS10, LpMADS14 and LpMADS16 message in ryegrass mRNA levels were examined in different tissues by real time quantitative PCR. For all three MADS genes, expression was shown to decrease dramatically in the shoot apex (the tissue which subsequently develops into reproductive structures e.g. the inflorescence, stem and flowers) upon exposure to a period of 12 weeks floral inductive vernalization, whereas expression in all three cases remained unchanged or increased in leaves during the floral transition, thus supporting the premise that the three MADS box genes represent possible inhibitors of the floral transition in ryegrass (see FIG. 2).

EXAMPLE 8

Ethanol Inducible Gene Expression in Grass

An ethanol inducible expression system has been described in the fungus *Aspergillus nidulans* (Felenbok et al., Gene 73 (1988), 385-396). It consist of the AlcA promoter with the specific AlcA box or recognition site and Alc Regulator (AlcR) that, after exposure to ethanol, binds to the AlcA box and initiates transcription of the gene fused to the AlcA promoter. The AlcA/R system has previously been tested in the dicot model plants tobacco (Caddick et al., Nature Biotechnology 16 (1988), 177-180) and *Arabidopsis* (Roslan et al., Plant J. 28 (2001), 225-235) and can be induced by other compounds than ethanol (WO 00/09704). The AlcA promoter has been fused to a 35S minimal promoter and in a test construct fused to the UidA reporter gene. The construct has the AlcR under control of the maize ubiquitin promoter. Here it is described that the system is applicable to grasses, exemplified by studies in *Festuca rubra*. Of the 22 independent transformants, 3 (14%) tested positive in the induced treatment and negative in the non-induced treatment, thus confirming the functionality of the ethanol-inducible gene expression system in grasses. The results are shown in FIG. 7.

EXAMPLE 9

Ethanol Inducible Self-Maintaining Loop

In order to avoid the potential need of multiple treatments with ethanol to induce flowering the ethanol induction system may be combined with a self-maintaining loop system.

Ideally flowering is repressed via over-expression of a repressor of flowering. In the "ethanol inducible self-maintaining loop system", the ethanol induction is not used directly to overcome repression by expression of a "floral restoration construct", instead it is used to induce an artificial transcription factor (434/VP16). This transcription factor activates in a second step the "floral restoration construct" from an artificial promoter (alcA-minimal 35S promoter with 434 operator sequences). In order to establish the self-maintaining loop a second gene cassette (cassette 2) is introduced expressing the 434/VP16 transcription factor itself from the artificial promoter (alcA-minimal 35S with 434 operator sequences). One ethanol pulse will produce the first 434/VP16 transcription factor molecules, which in turn will produce itself in a self-maintaining loop from gene cassette 2 and in turn further activate the expression of the "floral restoration construct". The self-maintaining loop will reset during meiosis and seed production so that in the next generation the loop is inactivated and flowering is repressed. In order to exclude leakiness of the self-maintaining loop in the un-induced state a third gene cassette may be introduced constitutively expressing the 434-repressor protein. The 434-repressor secures the tightness of the artificial promoter (alcA-minimal 35S with 434 operator sequences) driving the expression of the artificial activator (434/VP16) and the repressor RNAi construct. Only an ethanol-induced over-expression of the 434/VP16 activator will overcome the repression of the alcA-minimal 35S promoter with 434 operator sequences by the 434-repressor. For a better understanding the system is schematically drawn in FIG. 13.

Essential components of the ethanol inducible self-maintaining loop were confirmed in planta. There is a constitutive expression of the 434-repressor protein throughout the whole life span of the plant, which ensures non-leakiness of the artificial alcA-minimal 35S promoters with 434 operator elements. Storgaard et al. (Transgenic Research 11 (2002), 151-159) have shown a minimal promoter with 434 operator elements repressed by constitutive expression of the 434-repressor to be inducible by over-expression of the 434V16 activator in *Arabidopsis thaliana*.

Expression of a construct (G10) with the minimal 35S promoter and one 434 operator element driving GUS expression in *Brachypodium distachyon* showed no GUS staining in transgenic *Brachypodium distachyon* (inactivity of the promoter alone without presence of the 434/VP16 activator) whereas transgenic plants transformed with G12 (constitutive expression of the 434/VP16 activator) showed strong GUS expression (see FIG. 14).

EXAMPLE 10

Induced Restoration of WT Flowering Phenotype in an *Arabidopsis thaliana* Plant Otherwise Substantially Prevented in Flowering Through the Floral Suppressive Action of the Polypeptide of LpTFL1

In order to restore wild-type flowering time in late-flowering UBI::LpTFL1 *Arabidopsis* plants a construct was made in which a transgene encoding two 143 bp LpTFL1 inverted repeats separated by a spliceable intron (LpTFL1-RNAi) was placed under the control of a modified version of the ethanol inducible fungal promoter alcA (Caddick et al., Nat. Biotechnol. 16 (1998), 177-180). The alcR gene, which encodes a transcriptional regulator, was also incorporated into the construct under control of the maize Ubiquitin promoter (Christensen and Quail, Trans. Res. 5 (1996), 213-218). The AlcA::LpTFL1-PTGS-UBI::AlcR construct (hereafter named P05) was introduced into a late-flowering transgenic UBI::LpTFL1 *Arabidopsis* line 6, which flowers after approximately 66 days in LD. Several Kan$^r$, BASTA® resistant T1 plants were regenerated which were selfed for testing at the T2 generation.

The flowering time response of the P05 lines was determined under LD conditions and compared with that of the wild-type and the late-flowering LpTFL1-6 background line. Ten to fifteen seeds from each P05 T2 line were sown in soil together with the wild-type and the LpTFL1-6 background line. The seeds were stratified at 4° C. for three days and then moved to LD conditions at 24° C. All the P05 plants and the LpTFL1-6 background plants were sprayed with BASTA® (for presence of the UBI::LpTFL1 cassette) and the surviving plants and the wild-type plants were divided in two pots per line (4-6 plants per pot), one for the ethanol induction and the other as control.

For ethanol induction of the alcA promoter, 18 days old plants were placed in trays with two 2.0 ml eppendorf tubes containing 100% ethanol and covered by a transparent plastic bag. After 8 hrs of induction the plastic bag and the ethanol was removed. Ethanol inductions of 8 hrs duration were given five days a week for three weeks. As a control to the ethanol induction, the other half of the plants were placed in similar trays but without alcohol. Flowering time was scored as the number of days from germination till the opening of the first flower. In the wild-type the first flower opens immediately after bolting but in the late-flowering LpTFL1-6 line flowers are first formed several weeks after bolting.

In LD conditions the wildtype started bolting and flowering after about 26 days whereas the LpTFL1-6 plants did not start to flower until day 50 (FIG. 16). Some of the LpTFL1-6 plants (and the un-induced P05 plants) did not flower at the termination of experiment (after 75 days) and therefore these plants were simply scored as flowering after 75 days. Six out of 22 tested P05 lines showed ethanol-induced promotion of flowering (FIG. 17) and in these plants the number of days to flowering were reduced with 31% (line P05-32) up to 49% (line P05-06) (FIG. 1). Although the un-induced P05 plants started to bolt almost simultaneously with the ethanol induced plants, they did not produce flowers before the induced plants had produced mature siliques (FIG. 17).

Since the T1 plants were heterozygous for both the UBI::LpTFL1 and the P05 transgenes, it was expected that the transgenes would segregate at the T2 generation. It was therefore expected to see plants, which were either homozygous or heterozygous for both transgenes or homozygous or heterozygous for only one of the transgenes. The plants, which only carried the P05 construct but not the UBI::LpTFL1 cassette were eliminated by spraying with BASTA®. However, the plants were not selected for kanamycin resistance (P05), plants which only contained the UBI::LpTFL1 cassette but not the P05 construct were not removed from the experiment. In order not to include such plants in which P05 had been segregated out into our flowering time data, all plants in the experiment were tested by PCR for the presence of both UBI::LpTFL1 and P05 (FIG. 18). The result showed that the few late-flowering plants present among the ethanol induced plants all lacked the P05 construct and therefore were incapable of responding to the ethanol treatment (FIG. 16). Based on these findings the average number of days to flowering were calculated on the plants which by PCR had been shown to contain both P05 and the UBI::LpTFL1 cassette. In all lines the time to flowering was significantly reduced upon ethanol induction, whereas the time to flowering in the ethanol induced *LpTFL*1-6 background plants remained unchanged from the non-induced plants (FIG. 19). Thus by introducing the P05 construct into the late-flowering LpTFL1-6 plants and by inducing expression of the LpTFL1-RNAi it is possible to reduce the time to flowering on average with 40% (~26 days) and in some instances even up to 50% (line P05-06).

In some P05 plants we observed floral revertance in mature flowers (FIG. 20). We assume this aberrant floral development to be directly linked to a reduction in the alcA promoter activity during the two days every week, where no ethanol was applied to the plants. It has previously been shown that continuous high activity of the alcA promoter system requires continued application of ethanol and two days after the end of ethanol application, the activity of the alcA promoter is reduced by 70% (Rosland et al., Plant J. 28 (2001), 225-235). Thus decreasing the promoter activity to about 30% may result in a LpTFL1-RNAi level, which is insufficient to overcome the floral repression mediated by UBI::LpTFL1 and therefore the cells in the flowers or siliques reverted to a meristem identity. Upon new ethanol application the alcA promoter activity increased again consequently reducing the levels of LpTFL1 and new flowers could be made in place of a developing silique. Such discontinuous induction of the LpTFL1-RNAi may increase the overall seed yield since most of the floral revertance resulted in the replacement of one silique with 3-4 new similar-sized siliques.

Line P05-06 flowered after 33 days upon ethanol induction. This is only one week later than the wild-type, and by giving the ethanol induction even earlier than in this experiment (18 days post germination) it is assumed that it is possible to reduce the time to flowering even further down to wild-type levels. Similar effects may also be obtained by adding 0.5%, 1%, 2%, 4% or 5% ethanol solution, directly to the soil.

In conclusion, it has been shown that ethanol induced expression of the LpTFL1-PTGS construct initiates a posttranscriptional silencing of LpTFL1, which eventually will abolish the LpTFL1 repression of flowering in *Arabidopsis*. This result is to the inventor's knowledge the first evidence of a chemically induced PTGS-mediated release of transgene-induced flowering repression. This method will have wide applications for floral restoration and will not be limited to LpTFL1 but also to other floral repressors, such as the LpFT-like gene, the *Lolium perenne* MADS box genes LpMADS10, the LpMADS14, the LpMADS16 or the *Arabidopsis thaliana* Flowering Locus C/-F (FLC/FLF) gene (accession AF537203/AF116527), which may confer floral repression activity.

---

The invention claimed is:

1. An isolated polynucleotide which, when expressed in sense orientation in plants leads to a prevention of flowering, selected from the group consisting of
   (a) polynucleotides comprising a nucleotide sequence encoding a polypeptide with the amino acid sequence of SEQ ID NO:2;
   (b) polynucleotides comprising the coding region of the nucleotide sequence shown in SEQ ID NO:1; and
   (c) polynucleotides comprising a nucleotide sequence having a sequence identity of at least 95% to the coding region of SEQ ID NO: 1 and polynucleotides comprising a nucleotide sequence encoding a polypeptide having a sequence identity of at least 95% to the entire amino acid sequence of SEQ ID NO: 2, wherein said nucleotide sequence when expressed in sense orientation in plants leads to the production of the encoded polypeptide and to a prevention of flowering in comparison to wild-type plants.

2. The isolated polynucleotide of claim 1 which is DNA or RNA.

3. A recombinant nucleic acid molecule comprising the polynucleotide of claim 1.

4. The recombinant nucleic acid molecule of claim 3 further comprising expression control sequences operably linked to said polynucleotide.

5. A vector comprising the polynucleotide of claim 1 or the recombinant nucleic acid molecule of claim 4.

6. The vector of claim 5 further comprising expression control sequences operably linked to said polynucleotide.

7. A method for producing genetically engineered host cells comprising introducing the isolated polynucleotide of claim 1, or the recombinant nucleic acid molecule of claim 4 into isolated host cells.

8. An isolated host cell which is genetically engineered with the polynucleotide of claim 1.

9. The host cell of claim 8 which is a bacterial, yeast, fungus, plant or animal cell.

10. A method for producing a transgenic plant comprising the steps of
    (a) introducing the polynucleotide of claim 1 into the genome of a plant cell; and
    (b) regenerating the cell of (a) to a transgenic plant.

11. A transgenic plant, or plant tissue comprising the plant cell of claim 9 or obtainable by the method of claim 10.

12. The transgenic plant of claim 11 which, upon an increased amount of the protein encoded by said polynucleotide as compared to a corresponding wild-type plant, shows a prevention of flowering.

13. Propagation material or harvestable parts of the transgenic plant of claim 11 comprising said plant cell.

14. The propagation material of claim 13 which is a seed.

15. The isolated polynucleotide of claim 1, which is selected from the group consisting of polynucleotides comprising a nucleotide sequence having a sequence identity of at least 97% to the coding region of SEQ ID NO: 1 and polynucleotides comprising a nucleotide sequence encoding a polypeptide having a sequence identity of at least 97% to the entire amino acid sequence of SEQ ID NO: 2, wherein said nucleotide sequence when expressed in sense orientation in plants leads to the production of the encoded polypeptide and to a prevention of flowering in comparison to wild-type plants.

16. The isolated polynucleotide of claim 1, which is selected from the group consisting of polynucleotides comprising a nucleotide sequence having a sequence identity of at least 99% to the coding region of SEQ ID NO: 1 and polynucleotides comprising a nucleotide sequence encoding a polypeptide having a sequence identity of at least 99% to the entire amino acid sequence of SEQ ID NO: 2, wherein said nucleotide sequence when expressed in sense orientation in plants leads to the production of the encoded polypeptide and to a prevention of flowering in comparison to wild-type plants.

* * * * *

SEQUENCE LISTING

```
<160> NUMBER OF SEQ ID NOS: 80

<210> SEQ ID NO 1
<211> LENGTH: 831
<212> TYPE: DNA
<213> ORGANISM: Lolium perenne
<220> FEATURE:
<221> NAME/KEY: CDS
<222> LOCATION: (30)..(551)

<400> SEQUENCE: 1
gtacacttgc tctgagactc acatatact atg tct aat gac tcc ttg aca agg       53
                                Met Ser Asn Asp Ser Leu Thr Arg
                                 1               5 gcg cat ata gtt gga gat gtt cta gac cca ttt gct agc tca gtg cct     101
Ala His Ile Val Gly Asp Val Leu Asp Pro Phe Ala Ser Ser Val Pro
     10              15                  20 cta act gtg atg tat gat ggg agg cct gtg ttt aac ggg atg gag ttt     149
Leu Thr Val Met Tyr Asp Gly Arg Pro Val Phe Asn Gly Met Glu Phe
 25              30                  35                  40 cgc tca ccg gcg gtc act ctg aaa ccg aga gtt gag atc ggg ggt gac     197
Arg Ser Pro Ala Val Thr Leu Lys Pro Arg Val Glu Ile Gly Gly Asp
                 45                  50                  55 gat ttt cga gtg gcc tat acc cta gtt atg ata gat cct gat gcg cct     245
```

```
Asp Phe Arg Val Ala Tyr Thr Leu Val Met Ile Asp Pro Asp Ala Pro
            60                  65                  70 aat ccc agc aac cca acg ttg agg gag tac ctg cat tgg atg gtg act    293
Asn Pro Ser Asn Pro Thr Leu Arg Glu Tyr Leu His Trp Met Val Thr
         75                  80                  85 gat gtc cca gca tca aca gat gat agc ttt gga cga gag atc gtg cca    341
Asp Val Pro Ala Ser Thr Asp Asp Ser Phe Gly Arg Glu Ile Val Pro
     90                  95                 100 tac gag agc cca agc ccc acc atg ggt atc cac cgc atc gtg ctg gtg    389
Tyr Glu Ser Pro Ser Pro Thr Met Gly Ile His Arg Ile Val Leu Val
105                 110                 115                 120 ctg tat cag cag ctg ggg cgt gga aca gtg ctt gcg ccg caa gtg cgc    437
Leu Tyr Gln Gln Leu Gly Arg Gly Thr Val Leu Ala Pro Gln Val Arg
                125                 130                 135 cag aac ttc aac tcg cgc agc ttc gct cgc cgc ttc aac ctc gga aag    485
Gln Asn Phe Asn Ser Arg Ser Phe Ala Arg Arg Phe Asn Leu Gly Lys
            140                 145                 150 ccc gtc gcc gcc atg tac ttc aac tgc cag cgc ccg acg ggc acc ggt    533
Pro Val Ala Ala Met Tyr Phe Asn Cys Gln Arg Pro Thr Gly Thr Gly
        155                 160                 165 ggg aga agg ttc acc tga tctgtctcac tatagtatac tcgtatgtgc           581
Gly Arg Arg Phe Thr
    170 tgcatcgcac ggacctatac ctagctagct agaataaatg tattggattc atgtctggtc    641 tatcaaactg atgggtcagc catgttcagc tcgaaaggca attaagctcg agcttaccag    701 tactcagcat gcgtgcttaa ggatgcacgt tagccgcatc acacggtact tagctagaaa    761 gtttgaataa tgtacctgta ttgtacttgt aggctcctta agtaatgggc cttcacaagg    821 atgtgttgct                                                           831

<210> SEQ ID NO 2
<211> LENGTH: 173
<212> TYPE: PRT
<213> ORGANISM: Lolium perenne

<400> SEQUENCE: 2

Met Ser Asn Asp Ser Leu Thr Arg Ala His Ile Val Gly Asp Val Leu
1               5                   10                  15

Asp Pro Phe Ala Ser Ser Val Pro Leu Thr Val Met Tyr Asp Gly Arg
            20                  25                  30

Pro Val Phe Asn Gly Met Glu Phe Arg Ser Pro Ala Val Thr Leu Lys
        35                  40                  45

Pro Arg Val Glu Ile Gly Gly Asp Phe Arg Val Ala Tyr Thr Leu
    50                  55                  60

Val Met Ile Asp Pro Asp Ala Pro Asn Pro Ser Asn Pro Thr Leu Arg
65                  70                  75                  80

Glu Tyr Leu His Trp Met Val Thr Asp Val Pro Ala Ser Thr Asp Asp
                85                  90                  95

Ser Phe Gly Arg Glu Ile Val Pro Tyr Glu Ser Pro Ser Pro Thr Met
            100                 105                 110

Gly Ile His Arg Ile Val Leu Val Leu Tyr Gln Gln Leu Gly Arg Gly
        115                 120                 125

Thr Val Leu Ala Pro Gln Val Arg Gln Asn Phe Asn Ser Arg Ser Phe
    130                 135                 140

Ala Arg Arg Phe Asn Leu Gly Lys Pro Val Ala Ala Met Tyr Phe Asn
145                 150                 155                 160

Cys Gln Arg Pro Thr Gly Thr Gly Gly Arg Arg Phe Thr
                165                 170
```

165                 170

<210> SEQ ID NO 3
<211> LENGTH: 1142
<212> TYPE: DNA
<213> ORGANISM: Lolium perenne
<220> FEATURE:
<221> NAME/KEY: CDS
<222> LOCATION: (103)..(783)

<400> SEQUENCE: 3

| caaagaggaa aaaagaaaag ctcgtcgtcc cccgtccgcc cgcagatcta ctgctacacc | 60 |

| ttttgcgttg gtggtggtgc gggggagaag aaggagagg gg atg gcg ggg aag | 114 |
|  | Met Ala Gly Lys |
|  | 1 |

| agg gag agg ata tcg ata cgg aag atc gaa aac ctg gct gcg agg cag | 162 |
| Arg Glu Arg Ile Ser Ile Arg Lys Ile Glu Asn Leu Ala Ala Arg Gln |  |
| 5           10              15              20 |  |

| gtg acc ttc tcc aag cgc cgg agg ggc ctc ttc aag aag gct gag gag | 210 |
| Val Thr Phe Ser Lys Arg Arg Arg Gly Leu Phe Lys Lys Ala Glu Glu |  |
|     25              30              35 |  |

| ctc tcc atc ctc tgc gac gcg gag gtc ggc ctc gcc gtc ttc tcc gcc | 258 |
| Leu Ser Ile Leu Cys Asp Ala Glu Val Gly Leu Ala Val Phe Ser Ala |  |
|         40              45              50 |  |

| acc ggc aag ctc ttc aac ttc gct agc tcc agc atg aac cag att att | 306 |
| Thr Gly Lys Leu Phe Asn Phe Ala Ser Ser Ser Met Asn Gln Ile Ile |  |
|             55              60              65 |  |

| gat cgc tat aac tcc cat tcc aag aca ctt cag aga tca gat gag cca | 354 |
| Asp Arg Tyr Asn Ser His Ser Lys Thr Leu Gln Arg Ser Asp Glu Pro |  |
|         70              75              80 |  |

| tct cag ttg gac ttg cgt gag gac ggc aat tgt aca gaa cta agg gag | 402 |
| Ser Gln Leu Asp Leu Arg Glu Asp Gly Asn Cys Thr Glu Leu Arg Glu |  |
| 85              90              95              100 |  |

| gaa ctt gca gaa gca agt ctt tgg ctc cgg cag atg aga gga gag gag | 450 |
| Glu Leu Ala Glu Ala Ser Leu Trp Leu Arg Gln Met Arg Gly Glu Glu |  |
|         105             110             115 |  |

| ctg cag agc ctg aac gtc cag cag ctt cag gct ctc gag aag agc ctc | 498 |
| Leu Gln Ser Leu Asn Val Gln Gln Leu Gln Ala Leu Glu Lys Ser Leu |  |
|         120             125             130 |  |

| gag tct ggg ctc ggt tca gtg ctg aaa acc aag agc aaa aaa atc atg | 546 |
| Glu Ser Gly Leu Gly Ser Val Leu Lys Thr Lys Ser Lys Lys Ile Met |  |
|         135             140             145 |  |

| gac gag atc agc gag cta gag aga aag aga gtg caa ctg ata gag gaa | 594 |
| Asp Glu Ile Ser Glu Leu Glu Arg Lys Arg Val Gln Leu Ile Glu Glu |  |
| 150             155             160 |  |

| aat tca agg cta aag gag caa gcg tcc aag atg gag atg caa gtc gct | 642 |
| Asn Ser Arg Leu Lys Glu Gln Ala Ser Lys Met Glu Met Gln Val Ala |  |
| 165             170             175             180 |  |

| gct gat tcg cca gtg gtg tat gag gaa ggg cag tcg tct gaa tct gtc | 690 |
| Ala Asp Ser Pro Val Val Tyr Glu Glu Gly Gln Ser Ser Glu Ser Val |  |
|         185             190             195 |  |

| acc aac act tcg tat cca cgc cct ccc ctc gac acc gag gac agc tct | 738 |
| Thr Asn Thr Ser Tyr Pro Arg Pro Pro Leu Asp Thr Glu Asp Ser Ser |  |
|         200             205             210 |  |

| gac aca tct ctc agg ctc gga tta cca ctt ttc aac tca aag tga | 783 |
| Asp Thr Ser Leu Arg Leu Gly Leu Pro Leu Phe Asn Ser Lys |  |
|         215             220             225 |  |

| ttgtctggaa attatctcaa gcaaagtgat gctgctggtt acgacaactc ctgaacagat | 843 |

| cagtgatcag cgcgccgcat cgaataaacc gtttaagcat gcttggatga tgtgtgtaat | 903 |

| ctaaaagatt actggctttc gttacatgta gtatagtgca gcataataag agaacaggtt | 963 |

```
ctttgatgt tacctgctac tttttttttt catccttgtc ctgttttctg ccataaggtt    1023
ttagtagccc cctggtgatc tatcagaatt caagagttgt ttcagccaca tgaattattg   1083
atttcaacat aaaaagggtc tgttaggatg ttcaaaaaaa aaaaaaaaaa aaaaaaaa     1142

<210> SEQ ID NO 4
<211> LENGTH: 226
<212> TYPE: PRT
<213> ORGANISM: Lolium perenne

<400> SEQUENCE: 4

Met Ala Gly Lys Arg Glu Arg Ile Ser Ile Arg Lys Ile Glu Asn Leu
1               5                   10                  15

Ala Ala Arg Gln Val Thr Phe Ser Lys Arg Arg Arg Gly Leu Phe Lys
            20                  25                  30

Lys Ala Glu Glu Leu Ser Ile Leu Cys Asp Ala Glu Val Gly Leu Ala
        35                  40                  45

Val Phe Ser Ala Thr Gly Lys Leu Phe Asn Phe Ala Ser Ser Ser Met
    50                  55                  60

Asn Gln Ile Ile Asp Arg Tyr Asn Ser His Ser Lys Thr Leu Gln Arg
65                  70                  75                  80

Ser Asp Glu Pro Ser Gln Leu Asp Leu Arg Glu Asp Gly Asn Cys Thr
                85                  90                  95

Glu Leu Arg Glu Glu Leu Ala Glu Ala Ser Leu Trp Leu Arg Gln Met
            100                 105                 110

Arg Gly Glu Glu Leu Gln Ser Leu Asn Val Gln Leu Gln Ala Leu
        115                 120                 125

Glu Lys Ser Leu Glu Ser Gly Leu Gly Ser Val Leu Lys Thr Lys Ser
    130                 135                 140

Lys Lys Ile Met Asp Glu Ile Ser Glu Leu Glu Arg Lys Arg Val Gln
145                 150                 155                 160

Leu Ile Glu Glu Asn Ser Arg Leu Lys Glu Gln Ala Ser Lys Met Glu
                165                 170                 175

Met Gln Val Ala Ala Asp Ser Pro Val Val Tyr Glu Glu Gly Gln Ser
            180                 185                 190

Ser Glu Ser Val Thr Asn Thr Ser Tyr Pro Arg Pro Leu Asp Thr
        195                 200                 205

Glu Asp Ser Ser Asp Thr Ser Leu Arg Leu Gly Leu Pro Leu Phe Asn
    210                 215                 220

Ser Lys
225

<210> SEQ ID NO 5
<211> LENGTH: 1154
<212> TYPE: DNA
<213> ORGANISM: Lolium perenne
<220> FEATURE:
<221> NAME/KEY: CDS
<222> LOCATION: (143)..(829)

<400> SEQUENCE: 5
gctctcccct cctctgcttt cgcatcccca accgcaccac tgtgcctctc cgaccccggc    60
cggccgacgc gcgctacgcc tctcggcgtg cggactgggg agggaggagg agatcgatcg   120
atcagttggt cgggaggcgg cg atg gcg cgg gag agg cgc gag atc aag cgg   172
                         Met Ala Arg Glu Arg Arg Glu Ile Lys Arg
                         1               5                   10 ata gag agc gcg gcg gcg cgc cag gtc acc ttc tcc aag cgc cgc agg   220
```

```
Ile Glu Ser Ala Ala Ala Arg Gln Val Thr Phe Ser Lys Arg Arg
            15                  20                  25 ggc ctc ttc aag aag gcc gag gag ctc tcc gtc cta tgc gac gcc gac        268
Gly Leu Phe Lys Lys Ala Glu Glu Leu Ser Val Leu Cys Asp Ala Asp
            30                  35                  40 gtc gcg ctc atc gtc ttc tcc tcc aca ggg aag ctc tcc cag ttc gcc        316
Val Ala Leu Ile Val Phe Ser Ser Thr Gly Lys Leu Ser Gln Phe Ala
         45                  50                  55 agc tcc agt atg aat gag atc atc gac aag tac agc acc cat tct aag        364
Ser Ser Ser Met Asn Glu Ile Ile Asp Lys Tyr Ser Thr His Ser Lys
         60                  65                  70 aac ctg ggg aaa gca gac cag cct tct ctt gac ttg aat tta gaa cat        412
Asn Leu Gly Lys Ala Asp Gln Pro Ser Leu Asp Leu Asn Leu Glu His
75                  80                  85                  90 agt aag tat gca aat ctg aac gat cag ctt gcg gaa gct agt ctc cga        460
Ser Lys Tyr Ala Asn Leu Asn Asp Gln Leu Ala Glu Ala Ser Leu Arg
             95                  100                 105 ctt aga cag atg aga ggc gag ggg ctt gag ggg ttg act gtt gat gaa        508
Leu Arg Gln Met Arg Gly Glu Gly Leu Glu Gly Leu Thr Val Asp Glu
             110                 115                 120 ctc cag cag ttg gag aag aac ctt gaa act ggt ctg cac agg gtg ctt        556
Leu Gln Gln Leu Glu Lys Asn Leu Glu Thr Gly Leu His Arg Val Leu
             125                 130                 135 cag acg aaa gat caa caa ttc ttg gag cag atc aat gaa ttg caa cga        604
Gln Thr Lys Asp Gln Gln Phe Leu Glu Gln Ile Asn Glu Leu Gln Arg
         140                 145                 150 aag agc tca cag ctg gca gag gag aac atg caa ctg agg aac caa gta        652
Lys Ser Ser Gln Leu Ala Glu Glu Asn Met Gln Leu Arg Asn Gln Val
155                 160                 165                 170 tcc cag ata cca ata gct ggc aag cca gta gtt gct gat acc gaa aat        700
Ser Gln Ile Pro Ile Ala Gly Lys Pro Val Val Ala Asp Thr Glu Asn
             175                 180                 185 gtt att gct gag gat ggg cag tcc tct gaa tct gtc atg acg gcg ttg        748
Val Ile Ala Glu Asp Gly Gln Ser Ser Glu Ser Val Met Thr Ala Leu
             190                 195                 200 cac tcg gga agc tca cag gat aac gat gat ggt tca gat gta tcc ctg        796
His Ser Gly Ser Ser Gln Asp Asn Asp Asp Gly Ser Asp Val Ser Leu
             205                 210                 215 aaa ttg gga tta ccc tgc agt gcg tgg aag taa ctatataaaa ccgtcacttc      849
Lys Leu Gly Leu Pro Cys Ser Ala Trp Lys
         220                 225 agatctttat ggaactgccc acatcagtgg agaagctctt gtgtaatcga caaacgtacc      909
cgagctgcaa taatcttgca gctgaagcga gatcagttaa cctgatttat catccttgtg      969
gctgcatgac gtgatgttcc cgttttact gtttactagg atgttaacta aacttttaga      1029
tcgatctgat gtccatctta tccccgttgg cactatttgt tcatggtatc catgtacctt      1089
aactgtcagt atatcttaaa cttatggtct agawwwrmaa aaaaaaaaaa aaaaaaaaa      1149 aaaaa                                                                 1154

<210> SEQ ID NO 6
<211> LENGTH: 228
<212> TYPE: PRT
<213> ORGANISM: Lolium perenne

<400> SEQUENCE: 6

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30
```

```
Glu Glu Leu Ser Val Leu Cys Asp Ala Asp Val Ala Leu Ile Val Phe
         35                  40                  45

Ser Ser Thr Gly Lys Leu Ser Gln Phe Ala Ser Ser Met Asn Glu
 50                  55                  60

Ile Ile Asp Lys Tyr Ser Thr His Ser Lys Asn Leu Gly Lys Ala Asp
 65                  70                  75                  80

Gln Pro Ser Leu Asp Leu Asn Leu Glu His Ser Lys Tyr Ala Asn Leu
                 85                  90                  95

Asn Asp Gln Leu Ala Glu Ala Ser Leu Arg Leu Arg Gln Met Arg Gly
                100                 105                 110

Glu Gly Leu Glu Gly Leu Thr Val Asp Glu Leu Gln Gln Leu Glu Lys
            115                 120                 125

Asn Leu Glu Thr Gly Leu His Arg Val Leu Gln Thr Lys Asp Gln Gln
130                 135                 140

Phe Leu Glu Gln Ile Asn Glu Leu Gln Arg Lys Ser Ser Gln Leu Ala
145                 150                 155                 160

Glu Glu Asn Met Gln Leu Arg Asn Gln Val Ser Gln Ile Pro Ile Ala
                165                 170                 175

Gly Lys Pro Val Val Ala Asp Thr Glu Asn Val Ile Ala Glu Asp Gly
            180                 185                 190

Gln Ser Ser Glu Ser Val Met Thr Ala Leu His Ser Gly Ser Gln
        195                 200                 205

Asp Asn Asp Asp Gly Ser Asp Val Ser Leu Lys Leu Gly Leu Pro Cys
210                 215                 220

Ser Ala Trp Lys
225

<210> SEQ ID NO 7
<211> LENGTH: 1121
<212> TYPE: DNA
<213> ORGANISM: Lolium perenne
<220> FEATURE:
<221> NAME/KEY: misc_feature
<222> LOCATION: (986)..(986)
<223> OTHER INFORMATION: N=A, C, G or T
<220> FEATURE:
<221> NAME/KEY: misc_feature
<222> LOCATION: (1046)..(1046)
<223> OTHER INFORMATION: N=A, C, G or T
<220> FEATURE:
<221> NAME/KEY: CDS
<222> LOCATION: (99)..(758)

<400> SEQUENCE: 7
agagcagtct aaatctactc atttgctcgt gcggccaaga gggcggcggc ggcggtgcgc      60
gtgcgcgttg aggtttcccg gcggccggtc agggcgag atg gcg cgg gag agg cgg    116
                                          Met Ala Arg Glu Arg Arg
                                            1               5 gag ata cgg cgg ata gag agc gcg gca gcg cgg cag gtc acc ttc tcc      164
Glu Ile Arg Arg Ile Glu Ser Ala Ala Ala Arg Gln Val Thr Phe Ser
            10                  15                  20 aag cgg agg cgc ggg ctc ttc aag aag gcc gag gag ctc ggc gtg ctc      212
Lys Arg Arg Arg Gly Leu Phe Lys Lys Ala Glu Glu Leu Gly Val Leu
         25                  30                  35 tgc gac gcc gac gtc gcg ctc gtc gtc ttc tcc gcc acc ggc aag ctc      260
Cys Asp Ala Asp Val Ala Leu Val Val Phe Ser Ala Thr Gly Lys Leu
 40                  45                  50 tcc cag ttc gca agc tcc agt atg gac gag atc att gac aag tat agt      308
Ser Gln Phe Ala Ser Ser Ser Met Asp Glu Ile Ile Asp Lys Tyr Ser
 55                  60                  65                  70
```

```
gct cat tca aag aac ctg ggg aaa tca caa gag aag cct gca ctt gat      356
Ala His Ser Lys Asn Leu Gly Lys Ser Gln Glu Lys Pro Ala Leu Asp
            75                  80                  85 ttg aat gta gag cac agc aag tat aac agt ttg aat gaa aaa ctt gct      404
Leu Asn Val Glu His Ser Lys Tyr Asn Ser Leu Asn Glu Lys Leu Ala
        90                  95                 100 gaa gca agt ctt cac ctt aga cac atg aga ggt gag gaa ctt ggg gga      452
Glu Ala Ser Leu His Leu Arg His Met Arg Gly Glu Glu Leu Gly Gly
        105                 110                 115 ctg agt gtt ggg gaa ctg cag cag atg gaa aag gat ctt gaa aca gga      500
Leu Ser Val Gly Glu Leu Gln Gln Met Glu Lys Asp Leu Glu Thr Gly
    120                 125                 130 cta cag agg gtg ctt tgt aca aag gac caa caa ttc atg caa cag atc      548
Leu Gln Arg Val Leu Cys Thr Lys Asp Gln Gln Phe Met Gln Gln Ile
135                 140                 145                 150 agt gac ctc caa caa aag ggc aca cag ctg gca gaa gag aat atg cgc      596
Ser Asp Leu Gln Gln Lys Gly Thr Gln Leu Ala Glu Glu Asn Met Arg
                155                 160                 165 ttg aga aac caa atg cct cag gtg cca acg gcc ggc atg atg gct atc      644
Leu Arg Asn Gln Met Pro Gln Val Pro Thr Ala Gly Met Met Ala Ile
            170                 175                 180 act gaa gat gtt ctt tca tct gaa tct gtg atg acg gca gta cat tcc      692
Thr Glu Asp Val Leu Ser Ser Glu Ser Val Met Thr Ala Val His Ser
        185                 190                 195 gga agc tcg cag gac aat gac gac ggt tct gat ata tcg ctg aaa cta      740
Gly Ser Ser Gln Asp Asn Asp Asp Gly Ser Asp Ile Ser Leu Lys Leu
        200                 205                 210 gcg ttg cct tgg aag taa ggatcatgag gagaccacca tgataagacg             788
Ala Leu Pro Trp Lys
215 acggagttgc cttggtagag aggattgctc aatgctgtgg agactcccaa gctagactga    848 ctggaatggt cccatattag aaaccagatc aatttacccg aattgtcatc gttaagtctg    908 catgcgtatg gtgcagttgt tcacctttgc ttgggtcttc actcaacttg tagcatagtt    968 gtgtgtacgt actgcttntt cgacctgcgt cacgtatcat tcatgcgaac tacgtgcctg   1028 tttcttatgg ctatgtgnac ttatatttat gagaagctta ttggcgcagt ttcttgtgtg   1088 cgttggaaaa aaaaaaaaa aaaaaaaaaa aaa                                 1121

<210> SEQ ID NO 8
<211> LENGTH: 219
<212> TYPE: PRT
<213> ORGANISM: Lolium perenne

<400> SEQUENCE: 8

Met Ala Arg Glu Arg Arg Glu Ile Arg Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Glu Glu Leu Gly Val Leu Cys Asp Ala Asp Val Ala Leu Val Val Phe
        35                  40                  45

Ser Ala Thr Gly Lys Leu Ser Gln Phe Ala Ser Ser Met Asp Glu
    50                  55                  60

Ile Ile Asp Lys Tyr Ser Ala His Ser Lys Asn Leu Gly Lys Ser Gln
65                  70                  75                  80

Glu Lys Pro Ala Leu Asp Leu Asn Val Glu His Ser Lys Tyr Asn Ser
                85                  90                  95

Leu Asn Glu Lys Leu Ala Glu Ala Ser Leu His Leu Arg His Met Arg
```

```
                    100                 105                 110
Gly Glu Glu Leu Gly Gly Leu Ser Val Gly Glu Leu Gln Gln Met Glu
            115                 120                 125

Lys Asp Leu Glu Thr Gly Leu Gln Arg Val Leu Cys Thr Lys Asp Gln
130                 135                 140

Gln Phe Met Gln Gln Ile Ser Asp Leu Gln Gln Lys Gly Thr Gln Leu
145                 150                 155                 160

Ala Glu Glu Asn Met Arg Leu Arg Asn Gln Met Pro Gln Val Pro Thr
                165                 170                 175

Ala Gly Met Met Ala Ile Thr Glu Asp Val Leu Ser Ser Glu Ser Val
            180                 185                 190

Met Thr Ala Val His Ser Gly Ser Ser Gln Asp Asn Asp Asp Gly Ser
            195                 200                 205

Asp Ile Ser Leu Lys Leu Ala Leu Pro Trp Lys
        210                 215

<210> SEQ ID NO 9
<211> LENGTH: 1242
<212> TYPE: DNA
<213> ORGANISM: Lolium perenne
<220> FEATURE:
<221> NAME/KEY: CDS
<222> LOCATION: (12)..(1235)

<400> SEQUENCE: 9
agcgagtgaa g atg ctg ctc tgt gat ctc tct tct tac cag gag gcc acc      50
             Met Leu Leu Cys Asp Leu Ser Ser Tyr Gln Glu Ala Thr
               1               5                  10 gga tcc aac tcc cac ggt gga gac gta gcc gtc agc aac cat gtc ctg      98
Gly Ser Asn Ser His Gly Gly Asp Val Ala Val Ser Asn His Val Leu
 15                  20                  25 ctg agc cct ctc ttt ccg ccg gca gcg acg acg acg ctg cta ccc          146
Leu Ser Pro Leu Phe Pro Pro Ala Ala Thr Thr Thr Leu Leu Pro
 30                  35                  40                  45 agg ccg ccg ccg ctg ctg ctg gag gag ccc gcc agg gcc aag agg aag      194
Arg Pro Pro Pro Leu Leu Leu Glu Glu Pro Ala Arg Ala Lys Arg Lys
                 50                  55                  60 agg agc cag cca gga aac cca gac cct ggc tcg gag gtg atc gcg ctg      242
Arg Ser Gln Pro Gly Asn Pro Asp Pro Gly Ser Glu Val Ile Ala Leu
             65                  70                  75 tcg ccg cgg acg ctg gtg gcg acg aac cgc ttc gtg tgc gag atc tgc      290
Ser Pro Arg Thr Leu Val Ala Thr Asn Arg Phe Val Cys Glu Ile Cys
         80                  85                  90 aac aag ggc ttc cag agg gac cag aac ctg cag ctg cac cgc cgt ggc      338
Asn Lys Gly Phe Gln Arg Asp Gln Asn Leu Gln Leu His Arg Arg Gly
     95                 100                 105 cac aac ctc ccc tgg aag ctc cgg cag cgt agc ctg gcg ccg ctg ccc      386
His Asn Leu Pro Trp Lys Leu Arg Gln Arg Ser Leu Ala Pro Leu Pro
110                 115                 120                 125 agc agg ccc ggc gac gcg cca cgg aag cgc gtc tac gtc tgc ccc gag      434
Ser Arg Pro Gly Asp Ala Pro Arg Lys Arg Val Tyr Val Cys Pro Glu
                130                 135                 140 ccc acc tgt gtc cac cac gac ccg gca agg gcg ctc ggc gac ctc acc      482
Pro Thr Cys Val His His Asp Pro Ala Arg Ala Leu Gly Asp Leu Thr
            145                 150                 155 ggg atc aag aag cac ttc tcc agg aag cac ggc gag aag cgg tgg aag      530
Gly Ile Lys Lys His Phe Ser Arg Lys His Gly Glu Lys Arg Trp Lys
        160                 165                 170 tgc gag cgg tgc ggc aag tgc tac gcc gtg cac tcc gac tgg aag gca      578
Cys Glu Arg Cys Gly Lys Cys Tyr Ala Val His Ser Asp Trp Lys Ala
```

```
                          175                 180                 185
cac gtc aag aac tgc ggc acc cgc gag tac cga tgc gac tgt ggc ata         626
His Val Lys Asn Cys Gly Thr Arg Glu Tyr Arg Cys Asp Cys Gly Ile
190                 195                 200                 205 ctc ttc tca agg aaa gac agt ctg ctg acc cac agg gcc ttc tgt gat         674
Leu Phe Ser Arg Lys Asp Ser Leu Leu Thr His Arg Ala Phe Cys Asp
            210                 215                 220 gcc cta gct gaa gag agt gca agg ctt ctc gca gct gca aac aac agc         722
Ala Leu Ala Glu Glu Ser Ala Arg Leu Leu Ala Ala Ala Asn Asn Ser
225                 230                 235 atc acc atc agt acc acc acc tgc aac aat aac agc ggt agc agc gat         770
Ile Thr Ile Ser Thr Thr Thr Cys Asn Asn Asn Ser Gly Ser Ser Asp
    240                 245                 250 aac agc aac aac aac aat cta atc acg acc agc aac agt tca cca ctc         818
Asn Ser Asn Asn Asn Asn Leu Ile Thr Thr Ser Asn Ser Ser Pro Leu
255                 260                 265 ttc ctt cct ttc tct agt cca cct ccc cct caa agc cct aat ccc ctt         866
Phe Leu Pro Phe Ser Ser Pro Pro Pro Pro Gln Ser Pro Asn Pro Leu
270                 275                 280                 285 atg ttt ctc tcc caa gaa cct caa cat cac cag ctg ttc cct ccg ttc         914
Met Phe Leu Ser Gln Glu Pro Gln His His Gln Leu Phe Pro Pro Phe
                290                 295                 300 caa ccc ctg aca tac ctt gat gag ctc cct atg aac tcc gct atc acc         962
Gln Pro Leu Thr Tyr Leu Asp Glu Leu Pro Met Asn Ser Ala Ile Thr
            305                 310                 315 gac agt gtc tcg acc atc gcc gcc gac acg gtc acc tac cgg ctc agc        1010
Asp Ser Val Ser Thr Ile Ala Ala Asp Thr Val Thr Tyr Arg Leu Ser
320                 325                 330 caa gaa ggt tcg atg act atg cac gcc ggc gga cgc cgt ctc acc agg        1058
Gln Glu Gly Ser Met Thr Met His Ala Gly Gly Arg Arg Leu Thr Arg
335                 340                 345 gac ttc ctc ggc atc gac gat tcc ggg gat cag gtg gat gag ctg cag        1106
Asp Phe Leu Gly Ile Asp Asp Ser Gly Asp Gln Val Asp Glu Leu Gln
350                 355                 360                 365 ctg cca ctg tgt gcc act gca tac cag gga cgc tcc atc gcc acc gcc        1154
Leu Pro Leu Cys Ala Thr Ala Tyr Gln Gly Arg Ser Ile Ala Thr Ala
            370                 375                 380 gcc tgc tgc tcc acc gac atg acc agg cag tac ttc ggc agg ctg ccg        1202
Ala Cys Cys Ser Thr Asp Met Thr Arg Gln Tyr Phe Gly Arg Leu Pro
385                 390                 395 cca gtg aac gag acg tgg agc cac aac ttc tag aagggcg                    1242
Pro Val Asn Glu Thr Trp Ser His Asn Phe
            400                 405

<210> SEQ ID NO 10
<211> LENGTH: 407
<212> TYPE: PRT
<213> ORGANISM: Lolium perenne

<400> SEQUENCE: 10

Met Leu Leu Cys Asp Leu Ser Ser Tyr Gln Glu Ala Thr Gly Ser Asn
1               5                   10                  15

Ser His Gly Gly Asp Val Ala Val Ser Asn His Val Leu Leu Ser Pro
            20                  25                  30

Leu Phe Pro Pro Ala Ala Thr Thr Thr Thr Leu Leu Pro Arg Pro Pro
        35                  40                  45

Pro Leu Leu Leu Glu Glu Pro Ala Arg Ala Lys Arg Lys Arg Ser Gln
    50                  55                  60

Pro Gly Asn Pro Asp Pro Gly Ser Glu Val Ile Ala Leu Ser Pro Arg
65                  70                  75                  80
```

```
Thr Leu Val Ala Thr Asn Arg Phe Val Cys Glu Ile Cys Asn Lys Gly
                85                  90                  95

Phe Gln Arg Asp Gln Asn Leu Gln Leu His Arg Gly His Asn Leu
            100                 105                 110

Pro Trp Lys Leu Arg Gln Arg Ser Leu Ala Pro Leu Pro Ser Arg Pro
        115                 120                 125

Gly Asp Ala Pro Arg Lys Arg Val Tyr Val Cys Pro Glu Pro Thr Cys
    130                 135                 140

Val His His Asp Pro Ala Arg Ala Leu Gly Asp Leu Thr Gly Ile Lys
145                 150                 155                 160

Lys His Phe Ser Arg Lys His Gly Glu Lys Arg Trp Lys Cys Glu Arg
                165                 170                 175

Cys Gly Lys Cys Tyr Ala Val His Ser Asp Trp Lys Ala His Val Lys
            180                 185                 190

Asn Cys Gly Thr Arg Glu Tyr Arg Cys Asp Cys Gly Ile Leu Phe Ser
        195                 200                 205

Arg Lys Asp Ser Leu Leu Thr His Arg Ala Phe Cys Asp Ala Leu Ala
    210                 215                 220

Glu Glu Ser Ala Arg Leu Leu Ala Ala Ala Asn Ser Ile Thr Ile
225                 230                 235                 240

Ser Thr Thr Thr Cys Asn Asn Asn Ser Gly Ser Ser Asp Asn Ser Asn
                245                 250                 255

Asn Asn Asn Leu Ile Thr Thr Ser Asn Ser Ser Pro Leu Phe Leu Pro
            260                 265                 270

Phe Ser Ser Pro Pro Pro Gln Ser Pro Asn Pro Leu Met Phe Leu
        275                 280                 285

Ser Gln Glu Pro Gln His His Gln Leu Phe Pro Phe Gln Pro Leu
    290                 295                 300

Thr Tyr Leu Asp Glu Leu Pro Met Asn Ser Ala Ile Thr Asp Ser Val
305                 310                 315                 320

Ser Thr Ile Ala Ala Asp Thr Val Thr Tyr Arg Leu Ser Gln Glu Gly
                325                 330                 335

Ser Met Thr Met His Ala Gly Gly Arg Arg Leu Thr Arg Asp Phe Leu
            340                 345                 350

Gly Ile Asp Asp Ser Gly Asp Gln Val Asp Glu Leu Gln Leu Pro Leu
        355                 360                 365

Cys Ala Thr Ala Tyr Gln Gly Arg Ser Ile Ala Thr Ala Ala Cys Cys
    370                 375                 380

Ser Thr Asp Met Thr Arg Gln Tyr Phe Gly Arg Leu Pro Pro Val Asn
385                 390                 395                 400

Glu Thr Trp Ser His Asn Phe
                405

<210> SEQ ID NO 11
<211> LENGTH: 1485
<212> TYPE: DNA
<213> ORGANISM: Lolium perenne
<220> FEATURE:
<221> NAME/KEY: CDS
<222> LOCATION: (124)..(1257)

<400> SEQUENCE: 11
gccatgaaag gtagaggaac agaagaagaa acatacacag atatctaggg aaatagtagc      60
tactacaatc attaacaccc cttacatggt ctgtgtggtg caagccacaa ggcctccttg     120 ttc atg aag tcc aat tcc agc agc acc att tac gag gag gcg gtt ggg      168
```

|     | Met | Lys | Ser | Asn | Ser | Ser | Thr | Ile | Tyr | Glu | Glu | Ala | Val | Gly |      |
|     | 1   |     |     |     | 5   |     |     |     |     | 10  |     |     |     | 15  |      |
| caa | gag | ggg | agc | tgg | agc | agg | ctg | tgt | gat | gga | tgt | tgc | atg | gtg | cca  | 216 |
| Gln | Glu | Gly | Ser | Trp | Ser | Arg | Leu | Cys | Asp | Gly | Cys | Cys | Met | Val | Pro  |
|     |     |     |     | 20  |     |     |     |     | 25  |     |     |     |     | 30  |      |
| agc | gtg | gtg | tac | tgc | cac | gcc | gac | tcc | gca | tac | ctc | tgc | gcg | tct | tgt  | 264 |
| Ser | Val | Val | Tyr | Cys | His | Ala | Asp | Ser | Ala | Tyr | Leu | Cys | Ala | Ser | Cys  |
|     |     |     | 35  |     |     |     |     | 40  |     |     |     |     | 45  |     |      |
| gat | gtg | cgg | atc | cac | agt | gca | aac | cgt | gtg | gcc | tcg | cgc | cat | gag | cgc  | 312 |
| Asp | Val | Arg | Ile | His | Ser | Ala | Asn | Arg | Val | Ala | Ser | Arg | His | Glu | Arg  |
|     |     | 50  |     |     |     |     | 55  |     |     |     |     | 60  |     |     |      |
| gtg | tgc | ctc | tcc | gag | gcc | cac | gag | cat | gca | cca | gcg | ctg | ctg | caa | tgc  | 360 |
| Val | Cys | Leu | Ser | Glu | Ala | His | Glu | His | Ala | Pro | Ala | Leu | Leu | Gln | Cys  |
| 65  |     |     |     |     | 70  |     |     |     |     | 75  |     |     |     |     |      |
| cgc | aca | gac | gct | gta | gcg | tct | tgc | gcc | gcc | tat | gaa | gca | cag | gcg | cac  | 408 |
| Arg | Thr | Asp | Ala | Val | Ala | Ser | Cys | Ala | Ala | Tyr | Glu | Ala | Gln | Ala | His  |
| 80  |     |     |     |     | 85  |     |     |     |     | 90  |     |     |     |     | 95   |
| tac | gca | aac | ctg | ctc | gcc | ggg | atg | cac | cag | tgc | gtg | cct | gtg | gtt | tca  | 456 |
| Tyr | Ala | Asn | Leu | Leu | Ala | Gly | Met | His | Gln | Cys | Val | Pro | Val | Val | Ser  |
|     |     |     |     | 100 |     |     |     |     | 105 |     |     |     |     | 110 |      |
| cac | ccg | gcc | aca | gcc | att | ccg | act | gct | tct | tta | ctt | gct | gag | gca | gca  | 504 |
| His | Pro | Ala | Thr | Ala | Ile | Pro | Thr | Ala | Ser | Leu | Leu | Ala | Glu | Ala | Ala  |
|     |     |     | 115 |     |     |     |     | 120 |     |     |     |     | 125 |     |      |
| gtc | acc | act | acc | atc | ctc | agc | tgc | aag | gaa | gag | gag | gcg | tct | tgg | ttg  | 552 |
| Val | Thr | Thr | Thr | Ile | Leu | Ser | Cys | Lys | Glu | Glu | Glu | Ala | Ser | Trp | Leu  |
|     |     | 130 |     |     |     |     | 135 |     |     |     |     | 140 |     |     |      |
| cta | ctc | agc | aaa | aat | tct | gct | aac | cac | aat | tgc | agt | ggc | gac | aac | agg  | 600 |
| Leu | Leu | Ser | Lys | Asn | Ser | Ala | Asn | His | Asn | Cys | Ser | Gly | Asp | Asn | Arg  |
|     | 145 |     |     |     |     | 150 |     |     |     |     | 155 |     |     |     |      |
| agc | agc | agc | aca | tac | ttt | ggt | gaa | gtg | gat | gag | tat | ttt | gat | ctt | gtc  | 648 |
| Ser | Ser | Ser | Thr | Tyr | Phe | Gly | Glu | Val | Asp | Glu | Tyr | Phe | Asp | Leu | Val  |
| 160 |     |     |     |     | 165 |     |     |     |     | 170 |     |     |     |     | 175  |
| ggg | tac | aat | tcc | tac | tat | gat | agc | cgc | atg | aac | aac | aac | cga | gcg | cag  | 696 |
| Gly | Tyr | Asn | Ser | Tyr | Tyr | Asp | Ser | Arg | Met | Asn | Asn | Asn | Arg | Ala | Gln  |
|     |     |     | 180 |     |     |     |     | 185 |     |     |     |     | 190 |     |      |
| tac | gtg | atg | caa | gaa | cag | caa | cat | ctg | cag | ccc | atg | caa | aag | gaa | tat  | 744 |
| Tyr | Val | Met | Gln | Glu | Gln | Gln | His | Leu | Gln | Pro | Met | Gln | Lys | Glu | Tyr  |
|     |     | 195 |     |     |     |     | 200 |     |     |     |     | 205 |     |     |      |
| gca | gag | aag | gaa | ggg | agc | gag | tgt | gtg | gta | cct | tcg | cag | ttt | gct | acc  | 792 |
| Ala | Glu | Lys | Glu | Gly | Ser | Glu | Cys | Val | Val | Pro | Ser | Gln | Phe | Ala | Thr  |
|     | 210 |     |     |     |     | 215 |     |     |     |     | 220 |     |     |     |      |
| gcg | agt | aag | ccc | cag | cag | agt | ggt | tat | gca | ctt | gtg | ggg | gca | gag | cag  | 840 |
| Ala | Ser | Lys | Pro | Gln | Gln | Ser | Gly | Tyr | Ala | Leu | Val | Gly | Ala | Glu | Gln  |
|     | 225 |     |     |     |     | 230 |     |     |     |     | 235 |     |     |     |      |
| gct | gca | tcg | atg | act | gct | ggg | gtc | agt | gtt | tac | aca | gat | tct | gtc | aac  | 888 |
| Ala | Ala | Ser | Met | Thr | Ala | Gly | Val | Ser | Val | Tyr | Thr | Asp | Ser | Val | Asn  |
| 240 |     |     |     | 245 |     |     |     |     | 250 |     |     |     |     | 255 |      |
| aac | agc | ata | tcg | ttc | tca | tca | atg | gaa | ggg | gga | ata | gta | cca | gac | aat  | 936 |
| Asn | Ser | Ile | Ser | Phe | Ser | Ser | Met | Glu | Gly | Gly | Ile | Val | Pro | Asp | Asn  |
|     |     |     | 260 |     |     |     |     | 265 |     |     |     |     | 270 |     |      |
| acg | gtg | gta | gat | ctg | ccc | tac | tcc | atc | atc | cct | acg | cct | gct | gga | gcc  | 984 |
| Thr | Val | Val | Asp | Leu | Pro | Tyr | Ser | Ile | Ile | Pro | Thr | Pro | Ala | Gly | Ala  |
|     |     |     | 275 |     |     |     |     | 280 |     |     |     |     | 285 |     |      |
| agc | agc | ctc | cac | tca | ggt | cct | cca | ctt | cag | atg | cca | cta | cac | ttc | agc  | 1032 |
| Ser | Ser | Leu | His | Ser | Gly | Pro | Pro | Leu | Gln | Met | Pro | Leu | His | Phe | Ser  |
|     |     | 290 |     |     |     |     | 295 |     |     |     |     | 300 |     |     |      |
| tcc | atg | gac | aga | gag | gcc | aaa | gtc | ctg | agg | tac | aag | gag | aag | aag | aag  | 1080 |
| Ser | Met | Asp | Arg | Glu | Ala | Lys | Val | Leu | Arg | Tyr | Lys | Glu | Lys | Lys | Lys  |
|     |     | 305 |     |     |     |     | 310 |     |     |     |     | 315 |     |     |      |
| acc | aga | acg | ttc | gag | aag | acc | aca | cgt | tac | gca | aca | agg | aaa | gcc | tat  | 1128 |

```
Thr Arg Thr Phe Glu Lys Thr Thr Arg Tyr Ala Thr Arg Lys Ala Tyr
320                 325                 330                 335 gct gaa gca cgg ccg agg atc aag ggc cgc ttc gcg aaa ata tca gaa    1176
Ala Glu Ala Arg Pro Arg Ile Lys Gly Arg Phe Ala Lys Ile Ser Glu
                340                 345                 350 gcg gaa atg gaa gtg gac cag atg ttc tcg gct gca gct ctt tct gac    1224
Ala Glu Met Glu Val Asp Gln Met Phe Ser Ala Ala Ala Leu Ser Asp
            355                 360                 365 agt agc tac agt act gtt ccc tgg ttt caa tga gactctatta gacattacat  1277
Ser Ser Tyr Ser Thr Val Pro Trp Phe Gln
            370                 375 tagcatacat atgtacttac cagaacaata aggtccagtg caagcagttc aggtagatcg  1337
gtgctctgaa taattgtgtg gtatgcgaac cttaattgat aaggtatctt agtatctatg  1397
ttttgctttc taaatttgag atagcaaaat atgcattgtg cgatacttgc tcggtcgctt  1457
tgatatttca agtgaacaaa gagcagta                                     1485

<210> SEQ ID NO 12
<211> LENGTH: 377
<212> TYPE: PRT
<213> ORGANISM: Lolium perenne

<400> SEQUENCE: 12

Met Lys Ser Asn Ser Ser Thr Ile Tyr Glu Glu Ala Val Gly Gln
1               5                   10                  15

Glu Gly Ser Trp Ser Arg Leu Cys Asp Gly Cys Cys Met Val Pro Ser
            20                  25                  30

Val Val Tyr Cys His Ala Asp Ser Ala Tyr Leu Cys Ala Ser Cys Asp
            35                  40                  45

Val Arg Ile His Ser Ala Asn Arg Val Ala Ser Arg His Glu Arg Val
        50                  55                  60

Cys Leu Ser Glu Ala His Glu His Ala Pro Leu Leu Gln Cys Arg
65                  70                  75                  80

Thr Asp Ala Val Ala Ser Cys Ala Ala Tyr Glu Ala Gln Ala His Tyr
                85                  90                  95

Ala Asn Leu Leu Ala Gly Met His Gln Cys Val Pro Val Val Ser His
            100                 105                 110

Pro Ala Thr Ala Ile Pro Thr Ala Ser Leu Leu Ala Glu Ala Ala Val
            115                 120                 125

Thr Thr Thr Ile Leu Ser Cys Lys Glu Glu Ala Ser Trp Leu Leu
            130                 135                 140

Leu Ser Lys Asn Ser Ala Asn His Asn Cys Ser Gly Asp Asn Arg Ser
145                 150                 155                 160

Ser Ser Thr Tyr Phe Gly Glu Val Asp Glu Tyr Phe Asp Leu Val Gly
                165                 170                 175

Tyr Asn Ser Tyr Tyr Asp Ser Arg Met Asn Asn Asn Arg Ala Gln Tyr
            180                 185                 190

Val Met Gln Glu Gln Gln His Leu Gln Pro Met Gln Lys Glu Tyr Ala
            195                 200                 205

Glu Lys Glu Gly Ser Glu Cys Val Val Pro Ser Gln Phe Ala Thr Ala
210                 215                 220

Ser Lys Pro Gln Gln Ser Gly Tyr Ala Leu Val Gly Ala Glu Gln Ala
225                 230                 235                 240

Ala Ser Met Thr Ala Gly Val Ser Val Tyr Thr Asp Ser Val Asn Asn
                245                 250                 255

Ser Ile Ser Phe Ser Ser Met Glu Gly Gly Ile Val Pro Asp Asn Thr
```

```
                    260                 265                 270
Val Val Asp Leu Pro Tyr Ser Ile Ile Pro Thr Pro Ala Gly Ala Ser
            275                 280                 285

Ser Leu His Ser Gly Pro Pro Leu Gln Met Pro Leu His Phe Ser Ser
            290                 295                 300

Met Asp Arg Glu Ala Lys Val Leu Arg Tyr Lys Glu Lys Lys Lys Thr
305                 310                 315                 320

Arg Thr Phe Glu Lys Thr Thr Arg Tyr Ala Thr Arg Lys Ala Tyr Ala
                325                 330                 335

Glu Ala Arg Pro Arg Ile Lys Gly Arg Phe Ala Lys Ile Ser Glu Ala
            340                 345                 350

Glu Met Glu Val Asp Gln Met Phe Ser Ala Ala Ala Leu Ser Asp Ser
            355                 360                 365

Ser Tyr Ser Thr Val Pro Trp Phe Gln
    370                 375

<210> SEQ ID NO 13
<211> LENGTH: 1478
<212> TYPE: DNA
<213> ORGANISM: Lolium perenne
<220> FEATURE:
<221> NAME/KEY: CDS
<222> LOCATION: (56)..(1246)

<400> SEQUENCE: 13
ctcgagacta gttcccaaaa acaagagaag cgtctcgttc gttctcgtgt cgtgc atg        58
                                                              Met
                                                                1 gat ccc cac gac gcc ttc ctc gcc gcg cac ccg ttc cgg tgg gac ctc        106
Asp Pro His Asp Ala Phe Leu Ala Ala His Pro Phe Arg Trp Asp Leu
        5                  10                  15 ggc ccg ccg gct ccg gcg gcc gtg ccc gct cct cct cca ctg ccc atg        154
Gly Pro Pro Ala Pro Ala Ala Val Pro Ala Pro Pro Pro Leu Pro Met
        20                  25                  30 cct caa act ccc gcg ctg cct ccg gcg aac tcg ccg agg gag ctg gag        202
Pro Gln Thr Pro Ala Leu Pro Pro Ala Asn Ser Pro Arg Glu Leu Glu
    35                  40                  45 gat ctc gtg gcc ggg tac ggc gtg cgc ggg tcc acg gtt gcg cgg atc        250
Asp Leu Val Ala Gly Tyr Gly Val Arg Gly Ser Thr Val Ala Arg Ile
50                  55                  60                  65 tcc gag ctc ggg ttc act gct agc acg ctc ctg gtc atg acg gac cgc        298
Ser Glu Leu Gly Phe Thr Ala Ser Thr Leu Leu Val Met Thr Asp Arg
                70                  75                  80 gag ctg gac gac atg acg gcc gcg ctc gcc ggc ctg ttc cgc tgg gac        346
Glu Leu Asp Asp Met Thr Ala Ala Leu Ala Gly Leu Phe Arg Trp Asp
            85                  90                  95 ctg ctc atc ggc gag cgg ttc ggc ctg cgc gcc gcg ctg cgg gca gag        394
Leu Leu Ile Gly Glu Arg Phe Gly Leu Arg Ala Ala Leu Arg Ala Glu
        100                 105                 110 cgc ggc cgc ctg atg gca ctg cat ggg ggc cga cac cac ggt cac cag        442
Arg Gly Arg Leu Met Ala Leu His Gly Gly Arg His His Gly His Gln
    115                 120                 125 tcc ggc agc acc atc gac ggc gcc tcc caa gaa gtg ttg tcc aac gaa        490
Ser Gly Ser Thr Ile Asp Gly Ala Ser Gln Glu Val Leu Ser Asn Glu
130                 135                 140                 145 cgg gat ggg gcg gcg agt ggc gag gac gac gct ggc agg atg atg tta        538
Arg Asp Gly Ala Ala Ser Gly Glu Asp Asp Ala Gly Arg Met Met Leu
                150                 155                 160 tcg ggc aag aag ctg aag aat gga tcg gtg gcg agg aag gcc aag aaa        586
Ser Gly Lys Lys Leu Lys Asn Gly Ser Val Ala Arg Lys Ala Lys Lys
```

```
                     165                 170                 175
gca agg agg aag aag gtg gac ggg ctc cgg ctg gac cac atg cag gag       634
Ala Arg Arg Lys Lys Val Asp Gly Leu Arg Leu Asp His Met Gln Glu
        180                 185                 190 gac gag cgc gag gac ggc ggc ggc cgc tcg gag tca acg gag tcg tcg       682
Asp Glu Arg Glu Asp Gly Gly Gly Arg Ser Glu Ser Thr Glu Ser Ser
195                 200                 205 gct ggc gga ggc ggc ggc gtc gga ggg gag cgg cag cgg gag cac ccg       730
Ala Gly Gly Gly Gly Gly Val Gly Gly Glu Arg Gln Arg Glu His Pro
210                 215                 220                 225 ttc gtg gtg acg gag ccc ggg gag gtg gcg agg gcc aag aag aac ggg       778
Phe Val Val Thr Glu Pro Gly Glu Val Ala Arg Ala Lys Lys Asn Gly
                230                 235                 240 ctg gac tac ctg ttc cat ctc tac gag cag tgc cgc ctc ttc ctg ctc       826
Leu Asp Tyr Leu Phe His Leu Tyr Glu Gln Cys Arg Leu Phe Leu Leu
            245                 250                 255 cag gtg cag tcc atg gcc aag ctg cat ggc cac aag tct cca acc aag       874
Gln Val Gln Ser Met Ala Lys Leu His Gly His Lys Ser Pro Thr Lys
        260                 265                 270 gtg acg aac cag gtg ttc agg tac gcg agc aag gtg ggg gcg agc tac       922
Val Thr Asn Gln Val Phe Arg Tyr Ala Ser Lys Val Gly Ala Ser Tyr
275                 280                 285 atc aac aag ccc aag atg cgc cac tac gtg cac tgc tac gcg ctg cac       970
Ile Asn Lys Pro Lys Met Arg His Tyr Val His Cys Tyr Ala Leu His
290                 295                 300                 305 tgc ctc gac cag gag gcc tcc gac gcg ctg cgc cgg gcg tac aag gcg      1018
Cys Leu Asp Gln Glu Ala Ser Asp Ala Leu Arg Arg Ala Tyr Lys Ala
                310                 315                 320 cgc ggc gag aac gtc ggc gcc tgg agg cag gca tgc tac gcg ccg ctc      1066
Arg Gly Glu Asn Val Gly Ala Trp Arg Gln Ala Cys Tyr Ala Pro Leu
            325                 330                 335 gtc gac atc gcc gcc ggc cac ggc ttc gac gtc gac gcc gtc ttc gcc      1114
Val Asp Ile Ala Ala Gly His Gly Phe Asp Val Asp Ala Val Phe Ala
        340                 345                 350 gcg cac ccg cga ctc gcc atc tgg tac gtg ccc acc aga ctc cgc cag      1162
Ala His Pro Arg Leu Ala Ile Trp Tyr Val Pro Thr Arg Leu Arg Gln
355                 360                 365 ctc tgc cac cag gca agg agt gcg cac gac gcc gcc gcc aac gcc           1210
Leu Cys His Gln Ala Arg Ser Ala His Asp Ala Ala Ala Asn Ala
370                 375                 380                 385 aac ggg gcc atg ccg ccg ccg cgg ccc atg ttc tag cctgttgccc            1256
Asn Gly Ala Met Pro Pro Pro Arg Pro Met Phe
                390                 395 ggagcgagag ctggtgctcg tggtttctgt ctgtgggttt cgtgtgcact ctcactcggc     1316
cgtgtttcct tctcctgcgt gggctagaat ccgtgtttgt tgcttaggcc gatccagcag     1376
gctttgtctc tgagcagccc atgcgactat gcgagggacc tgcttgtaat atggatggat     1436
gtttaattct aggacatgaa atgtgatgaa tgttaatctt tg                        1478

<210> SEQ ID NO 14
<211> LENGTH: 396
<212> TYPE: PRT
<213> ORGANISM: Lolium perenne

<400> SEQUENCE: 14

Met Asp Pro His Asp Ala Phe Leu Ala Ala His Pro Phe Arg Trp Asp
1               5                   10                  15

Leu Gly Pro Pro Ala Pro Ala Ala Val Pro Ala Pro Pro Leu Pro
            20                  25                  30
```

```
Met Pro Gln Thr Pro Ala Leu Pro Ala Asn Ser Pro Arg Glu Leu
         35                  40                  45
Glu Asp Leu Val Ala Gly Tyr Gly Val Arg Gly Ser Thr Val Ala Arg
 50                  55                  60
Ile Ser Glu Leu Gly Phe Thr Ala Ser Thr Leu Leu Val Met Thr Asp
 65                  70                  75                  80
Arg Glu Leu Asp Asp Met Thr Ala Ala Leu Ala Gly Leu Phe Arg Trp
                 85                  90                  95
Asp Leu Leu Ile Gly Glu Arg Phe Gly Leu Arg Ala Ala Leu Arg Ala
                100                 105                 110
Glu Arg Gly Arg Leu Met Ala Leu His Gly Arg His His Gly His
            115                 120                 125
Gln Ser Gly Ser Thr Ile Asp Gly Ala Ser Gln Glu Val Leu Ser Asn
            130                 135                 140
Glu Arg Asp Gly Ala Ala Ser Gly Glu Asp Asp Ala Gly Arg Met Met
145                 150                 155                 160
Leu Ser Gly Lys Lys Leu Lys Asn Gly Ser Val Ala Arg Lys Ala Lys
                165                 170                 175
Lys Ala Arg Arg Lys Lys Val Asp Gly Leu Arg Leu Asp His Met Gln
            180                 185                 190
Glu Asp Glu Arg Glu Asp Gly Gly Arg Ser Glu Ser Thr Glu Ser
            195                 200                 205
Ser Ala Gly Gly Gly Gly Val Gly Gly Glu Arg Gln Arg Glu His
210                 215                 220
Pro Phe Val Val Thr Glu Pro Gly Glu Val Ala Arg Ala Lys Lys Asn
225                 230                 235                 240
Gly Leu Asp Tyr Leu Phe His Leu Tyr Glu Gln Cys Arg Leu Phe Leu
                245                 250                 255
Leu Gln Val Gln Ser Met Ala Lys Leu His Gly His Lys Ser Pro Thr
                260                 265                 270
Lys Val Thr Asn Gln Val Phe Arg Tyr Ala Ser Lys Val Gly Ala Ser
            275                 280                 285
Tyr Ile Asn Lys Pro Lys Met Arg His Tyr Val His Cys Tyr Ala Leu
290                 295                 300
His Cys Leu Asp Gln Glu Ala Ser Asp Ala Leu Arg Arg Ala Tyr Lys
305                 310                 315                 320
Ala Arg Gly Glu Asn Val Gly Ala Trp Arg Gln Ala Cys Tyr Ala Pro
                325                 330                 335
Leu Val Asp Ile Ala Ala Gly His Gly Phe Asp Val Asp Ala Val Phe
                340                 345                 350
Ala Ala His Pro Arg Leu Ala Ile Trp Tyr Val Pro Thr Arg Leu Arg
            355                 360                 365
Gln Leu Cys His Gln Ala Arg Ser Ala His Asp Ala Ala Ala Asn
            370                 375                 380
Ala Asn Gly Ala Met Pro Pro Arg Pro Met Phe
385                 390                 395

<210> SEQ ID NO 15
<211> LENGTH: 1266
<212> TYPE: DNA
<213> ORGANISM: Lolium perenne
<220> FEATURE:
<221> NAME/KEY: CDS
<222> LOCATION: (164)..(901)

<400> SEQUENCE: 15
```

```
gttgttgttc gccctcctc tcctcttctt ccccactgga cgaacgccat gacaccggcc      60
ccacggctcc acctgcaccc tcgggactag ccgtcgccgt cgccgtccgg gcgggttgtg     120
gattagggtt tggtctgctc ttcgttcgag ggagggaggc gag atg ggg cgc ggc      175
                                              Met Gly Arg Gly
                                              1 aag gtg cag ctc aag cgg atc gag aac aag atc aac cgc cag gtc acc      223
Lys Val Gln Leu Lys Arg Ile Glu Asn Lys Ile Asn Arg Gln Val Thr
  5              10                  15                  20 ttc tcc aag cgc cgc tcg ggg ctg ctc aag aag gcg cac gag atc tcc      271
Phe Ser Lys Arg Arg Ser Gly Leu Leu Lys Lys Ala His Glu Ile Ser
                25                  30                  35 gtg ctc tgc gac gcc gag gtc ggg ctc atc atc ttc tcc acc aag gga      319
Val Leu Cys Asp Ala Glu Val Gly Leu Ile Ile Phe Ser Thr Lys Gly
             40                  45                  50 aag ctc tac gag ttc gca acc gac tca tgt atg gac aaa att ctt gag      367
Lys Leu Tyr Glu Phe Ala Thr Asp Ser Cys Met Asp Lys Ile Leu Glu
         55                  60                  65 cgg tat gag cgc tac tcc tat gca gag aaa gtg ctc att tca acc gaa      415
Arg Tyr Glu Arg Tyr Ser Tyr Ala Glu Lys Val Leu Ile Ser Thr Glu
     70                  75                  80 tct gaa att cag gga aac tgg tgt cat gaa tat agg aaa ctg aag gcg      463
Ser Glu Ile Gln Gly Asn Trp Cys His Glu Tyr Arg Lys Leu Lys Ala
 85                  90                  95                 100 aag gtt gag aca ata cag aga tgt caa aag cat cta atg gga gag gat      511
Lys Val Glu Thr Ile Gln Arg Cys Gln Lys His Leu Met Gly Glu Asp
                105                 110                 115 ctt gaa tca ttg aat ctc aag gag ttg cag caa cta gag cag cag ctg      559
Leu Glu Ser Leu Asn Leu Lys Glu Leu Gln Gln Leu Glu Gln Gln Leu
            120                 125                 130 gaa agt tca ctg aaa cat att aga gcc aga aag aac cag ctt atg cac      607
Glu Ser Ser Leu Lys His Ile Arg Ala Arg Lys Asn Gln Leu Met His
        135                 140                 145 gaa tcc ata tct gag ctt caa aag aag gag agg tca ctg cag gag gag      655
Glu Ser Ile Ser Glu Leu Gln Lys Lys Glu Arg Ser Leu Gln Glu Glu
    150                 155                 160 aat aaa att ctc cag aag gaa ctc ata gag aag cag aag gcc cac acg      703
Asn Lys Ile Leu Gln Lys Glu Leu Ile Glu Lys Gln Lys Ala His Thr
165                 170                 175                 180 cag caa gcg cag tgg gag caa act cag ccc caa acc agc tct tcc tcc      751
Gln Gln Ala Gln Trp Glu Gln Thr Gln Pro Gln Thr Ser Ser Ser Ser
                185                 190                 195 tcc tcc ttt atg atg ggg gaa gct acc cca gca aca aat tgc agt aat      799
Ser Ser Phe Met Met Gly Glu Ala Thr Pro Ala Thr Asn Cys Ser Asn
            200                 205                 210 ccc cca gca gcg gcc agc gac aga gca gag gat gcg acg ggg cag cct      847
Pro Pro Ala Ala Ala Ser Asp Arg Ala Glu Asp Ala Thr Gly Gln Pro
        215                 220                 225 tca gct cgc acg gtg ctt cca cca tgg atg gtg agt cac atc aac aat      895
Ser Ala Arg Thr Val Leu Pro Pro Trp Met Val Ser His Ile Asn Asn
    230                 235                 240 ggc tga agggccttc cactccatct aaacgtatta ttcagtacgt gtagcgagct        951
Gly
245 gcaccggcct gtcttcttgt ggttgctagc aagctgaccc ctagaggaaa gcagaaaggg    1011 aaaattcgga gaaaggtagc aggttgcaat gtgtatattt cactctgttc tgctcagttt    1071 ccctcctgcg tgagctgact tcacgtaaga gttatttaac ttgtaataca tgtgtagcgt    1131 gagtgacaaa ttttccactt tctacgaccc tcttgggtac cgtctgtttc tgtgaattaa    1191
```

```
actatccaat atgagtatta tgtatattgt gattgttgaa ataaaattaa tctggaccct      1251
tgtctccgtg atctt                                                      1266

<210> SEQ ID NO 16
<211> LENGTH: 245
<212> TYPE: PRT
<213> ORGANISM: Lolium perenne

<400> SEQUENCE: 16

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Thr Glu Ser Glu Ile Gln Gly Asn Trp Cys His Glu Tyr Arg
                85                  90                  95

Lys Leu Lys Ala Lys Val Glu Thr Ile Gln Arg Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Ile Leu Gln Lys Glu Leu Ile Glu Lys Gln
                165                 170                 175

Lys Ala His Thr Gln Gln Ala Gln Trp Glu Gln Thr Gln Pro Gln Thr
            180                 185                 190

Ser Ser Ser Ser Ser Ser Phe Met Met Gly Glu Ala Thr Pro Ala Thr
        195                 200                 205

Asn Cys Ser Asn Pro Pro Ala Ala Ala Ser Asp Arg Ala Glu Asp Ala
    210                 215                 220

Thr Gly Gln Pro Ser Ala Arg Thr Val Leu Pro Pro Trp Met Val Ser
225                 230                 235                 240

His Ile Asn Asn Gly
                245

<210> SEQ ID NO 17
<211> LENGTH: 1055
<212> TYPE: DNA
<213> ORGANISM: Lolium perenne
<220> FEATURE:
<221> NAME/KEY: CDS
<222> LOCATION: (83)..(868)

<400> SEQUENCE: 17
ctccctccgg ccaattcctt ggtagacagc cggcagccgg cagctagatc agggagaatc      60
agaggcacga aatcaaggca ag atg ggt cgc ggc aag gtg cag ctg aag cgg     112
                        Met Gly Arg Gly Lys Val Gln Leu Lys Arg
                        1               5                   10 ata gag aac aag ata aac cgt cag gtg acc ttc tcc aag cgc cgc aac      160
Ile Glu Asn Lys Ile Asn Arg Gln Val Thr Phe Ser Lys Arg Arg Asn
            15                  20                  25
```

| | | | | | | | | | | | | | | | |
|---|---|---|---|---|---|---|---|---|---|---|---|---|---|---|---|
| ggg | cta | ctc | aag | aag | gcg | cac | gag | atc | tcc | gtc | ctc | tgc | gac | gcc | gag | 208
| Gly | Leu | Leu | Lys | Lys | Ala | His | Glu | Ile | Ser | Val | Leu | Cys | Asp | Ala | Glu |
| | | | 30 | | | | 35 | | | | 40 | | | | |

```
gtc gcc gtc gtc gtc ttc tcc ccg aaa ggg aag ctc tat gag tac gcc        256
Val Ala Val Val Val Phe Ser Pro Lys Gly Lys Leu Tyr Glu Tyr Ala
            45                  50                  55 act gac tcc agc atg gac aaa att ctt gaa cgt tat gaa cgc tac tct        304
Thr Asp Ser Ser Met Asp Lys Ile Leu Glu Arg Tyr Glu Arg Tyr Ser
    60                  65                  70 tat gct gaa aag gct ttg att tca gct gaa tct gaa agt gag gga aat        352
Tyr Ala Glu Lys Ala Leu Ile Ser Ala Glu Ser Glu Ser Glu Gly Asn
75                  80                  85                  90 tgg tgc cat gaa tac agg aaa ctg aag gcg aag att gag act ata caa        400
Trp Cys His Glu Tyr Arg Lys Leu Lys Ala Lys Ile Glu Thr Ile Gln
                95                  100                 105 aaa tgt cac aag cac ctc atg ggg gag gat ctg gag tgt cta aac ctg        448
Lys Cys His Lys His Leu Met Gly Glu Asp Leu Glu Cys Leu Asn Leu
            110                 115                 120 aaa gag ctc caa caa cta gag cag cag ctg gag agt tca ttg aag cac        496
Lys Glu Leu Gln Gln Leu Glu Gln Gln Leu Glu Ser Ser Leu Lys His
        125                 130                 135 atc aga tcg aga aag agc cac ctt atg atg gag tcc att tct gag cta        544
Ile Arg Ser Arg Lys Ser His Leu Met Met Glu Ser Ile Ser Glu Leu
    140                 145                 150 cag aag aag gag cgg tca ctc cag gag gag aac aag gct cta cag aag        592
Gln Lys Lys Glu Arg Ser Leu Gln Glu Glu Asn Lys Ala Leu Gln Lys
155                 160                 165                 170 gaa ctg gtg gag agg cag aag gcg gcc agg cag cag cag caa gag cag        640
Glu Leu Val Glu Arg Gln Lys Ala Ala Arg Gln Gln Gln Gln Glu Gln
                175                 180                 185 tgg gac cgt cag acc caa aca caa caa gcc caa aac caa cct cag gcc        688
Trp Asp Arg Gln Thr Gln Thr Gln Gln Ala Gln Asn Gln Pro Gln Ala
            190                 195                 200 cag acg agc tca tca tct tcc tcc ttc atg atg agg gat cag cag gcc        736
Gln Thr Ser Ser Ser Ser Ser Phe Met Met Arg Asp Gln Gln Ala
        205                 210                 215 cat gct caa caa aac atc tgt tac ccg ccg gtg aca atg ggt gga gag        784
His Ala Gln Gln Asn Ile Cys Tyr Pro Pro Val Thr Met Gly Gly Glu
    220                 225                 230 gct gtg gcc gcg gcg cca ggg cag cag ggg cag ctt cgc atc gga ggc        832
Ala Val Ala Ala Ala Pro Gly Gln Gln Gly Gln Leu Arg Ile Gly Gly
235                 240                 245                 250 ctg cca cca tgg atg ctg agc cac ctc aac gct tga ggaagaaga             878
Leu Pro Pro Trp Met Leu Ser His Leu Asn Ala
                255                 260 gggtcaattg ccaaagcagc tgcagctgca ttaatcatag aatctaccaa ttaagctgct     938
atggttatgt ttgcttgccc ccctacccct atatgtatat gatttgcaag aaaagagcag     998
atcgtgagga atgctggtgt acgtacctac gtagctgtat aattttgttg catgttt       1055

<210> SEQ ID NO 18
<211> LENGTH: 261
<212> TYPE: PRT
<213> ORGANISM: Lolium perenne

<400> SEQUENCE: 18

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30
```

His Glu Ile Ser Val Leu Cys Asp Ala Glu Val Ala Val Val Phe
        35                  40                  45

Ser Pro Lys Gly Lys Leu Tyr Glu Tyr Ala Thr Asp Ser Ser Met Asp
 50                  55                  60

Lys Ile Leu Glu Arg Tyr Glu Arg Tyr Ser Tyr Ala Glu Lys Ala Leu
 65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Cys Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Arg Gln Gln Gln Gln Glu Gln Trp Asp Arg Gln Thr Gln
            180                 185                 190

Thr Gln Gln Ala Gln Asn Gln Pro Gln Ala Gln Thr Ser Ser Ser Ser
        195                 200                 205

Ser Ser Phe Met Met Arg Asp Gln Gln Ala His Ala Gln Gln Asn Ile
    210                 215                 220

Cys Tyr Pro Pro Val Thr Met Gly Gly Glu Ala Val Ala Ala Ala Pro
225                 230                 235                 240

Gly Gln Gln Gly Gln Leu Arg Ile Gly Gly Leu Pro Pro Trp Met Leu
                245                 250                 255

Ser His Leu Asn Ala
            260

<210> SEQ ID NO 19
<211> LENGTH: 1245
<212> TYPE: DNA
<213> ORGANISM: Lolium perenne
<220> FEATURE:
<221> NAME/KEY: misc_feature
<222> LOCATION: (1224)..(1224)
<223> OTHER INFORMATION: N=A, C, G or T
<220> FEATURE:
<221> NAME/KEY: misc_feature
<222> LOCATION: (1236)..(1236)
<223> OTHER INFORMATION: N=A, C, G or T
<220> FEATURE:
<221> NAME/KEY: misc_feature
<222> LOCATION: (1240)..(1240)
<223> OTHER INFORMATION: N=A, C, G or T
<220> FEATURE:
<221> NAME/KEY: CDS
<222> LOCATION: (89)..(928)

<400> SEQUENCE: 19
ccgactccct ctccctctcg tcggttcgcc accgtagcag ccagctagct aggtactgca        60
ttcgccgccg agccggaagg aggcggag atg ggg cgc ggg ccg gtg cag ctg          112
                                Met Gly Arg Gly Pro Val Gln Leu
                                 1               5 cgg cgg atc gag aac aag ata aac cgc cag gtc acc ttc tcc aag cgc         160
Arg Arg Ile Glu Asn Lys Ile Asn Arg Gln Val Thr Phe Ser Lys Arg
         10                  15                  20 cgg agc ggg ctg ctc aag aag gcg cac gag atc tcc gtg ctc tgc gac         208

```
        Arg Ser Gly Leu Leu Lys Lys Ala His Glu Ile Ser Val Leu Cys Asp
         25                  30                  35                  40 gct gag gtc gcg ctc atc gta ttc tcc acc aag gga aag ctc tac gag        256
Ala Glu Val Ala Leu Ile Val Phe Ser Thr Lys Gly Lys Leu Tyr Glu
                    45                  50                  55 tac tcc agc cag gac agt aac atg gat gtc att ctt gaa cgt tac cag        304
Tyr Ser Ser Gln Asp Ser Asn Met Asp Val Ile Leu Glu Arg Tyr Gln
                60                  65                  70 cgt tac tca ttc gaa gaa aga gct ata gtg gat caa aat att gga ggc        352
Arg Tyr Ser Phe Glu Glu Arg Ala Ile Val Asp Gln Asn Ile Gly Gly
            75                  80                  85 cag gca aat tgg gga gat gaa ttt gga agt ttg aaa att aaa ctc gat        400
Gln Ala Asn Trp Gly Asp Glu Phe Gly Ser Leu Lys Ile Lys Leu Asp
        90                  95                 100 gca ctc cag aag agt caa agg caa ctc tta ggt gaa caa ttg gac cca        448
Ala Leu Gln Lys Ser Gln Arg Gln Leu Leu Gly Glu Gln Leu Asp Pro
    105                 110                 115                 120 ctg acc aca aaa gaa ctt caa caa ttg gaa cag cag cta gat agt tct        496
Leu Thr Thr Lys Glu Leu Gln Gln Leu Glu Gln Gln Leu Asp Ser Ser
                    125                 130                 135 ttg aag cac ata agg tca aga aag aat cag ctt ctg ttt gag tca ata        544
Leu Lys His Ile Arg Ser Arg Lys Asn Gln Leu Leu Phe Glu Ser Ile
                140                 145                 150 tct gag ctt cag aag aag gag aag tca ctt aaa gat cag aat ggc gtc        592
Ser Glu Leu Gln Lys Lys Glu Lys Ser Leu Lys Asp Gln Asn Gly Val
            155                 160                 165 ctg cag aag cac ctc gtg gag aca gaa aag gag aaa agt aac gtt tta        640
Leu Gln Lys His Leu Val Glu Thr Glu Lys Glu Lys Ser Asn Val Leu
        170                 175                 180 tcg aat att cat cac cga gag cag acg aat gga gca gca aat att cat        688
Ser Asn Ile His His Arg Glu Gln Thr Asn Gly Ala Ala Asn Ile His
    185                 190                 195                 200 cgc cgg gag cag atg aat gaa aca aca cat att cat aac cag gag cag        736
Arg Arg Glu Gln Met Asn Glu Thr Thr His Ile His Asn Gln Glu Gln
                    205                 210                 215 ctc aat gga gca aca aca agc tca ccg tca cct aca cca gtg gcg gtc        784
Leu Asn Gly Ala Thr Thr Ser Ser Pro Ser Pro Thr Pro Val Ala Val
                220                 225                 230 cta gat tcc gtg gca act cta aat att ggg tca tct caa tct aga gaa        832
Leu Asp Ser Val Ala Thr Leu Asn Ile Gly Ser Ser Gln Ser Arg Glu
            235                 240                 245 gca gca gga gag gag cca gaa tct cag ccg tcc ccg gca caa gca aac        880
Ala Ala Gly Glu Glu Pro Glu Ser Gln Pro Ser Pro Ala Gln Ala Asn
        250                 255                 260 agc ggc aag cta cca cca tgg atg ctc cgc acc atc agt aac aga tga        928
Ser Gly Lys Leu Pro Pro Trp Met Leu Arg Thr Ile Ser Asn Arg
    265                 270                 275 tgagatgaag ggttccgacg gggccttgtg tgactccact ggaaggcgat ctcggcacct       988
gactgtccat catggaagct agctgccggt gtgaaatcat ccatatccaa caacagatcc      1048
tggcgtagcc accaataaga ccatgtgtct ttgttacagg gtgaatgggg tcttcccgtt      1108
ctttagcttt tctgcattat aagacactgc gtcttggttc cacgttcctc cctctttttct    1168 ccaattgatg aagctgcgtc ttggtgattg gagttggaat gtatgtttta accggntggt     1228
ttgtttcncg tnttgtg                                                    1245

<210> SEQ ID NO 20
<211> LENGTH: 279
<212> TYPE: PRT
<213> ORGANISM: Lolium perenne
```

<400> SEQUENCE: 20

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Asn Met
    50                  55                  60

Asp Val Ile Leu Glu Arg Tyr Gln Arg Tyr Ser Phe Glu Glu Arg Ala
65                  70                  75                  80

Ile Val Asp Gln Asn Ile Gly Gly Gln Ala Asn Trp Gly Asp Glu Phe
                85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
    130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Ser Asn Val Leu Ser Asn Ile His His Arg Glu Gln
            180                 185                 190

Thr Asn Gly Ala Ala Asn Ile His Arg Arg Glu Gln Met Asn Glu Thr
        195                 200                 205

Thr His Ile His Asn Gln Glu Gln Leu Asn Gly Ala Thr Thr Ser Ser
    210                 215                 220

Pro Ser Pro Thr Pro Val Ala Val Leu Asp Ser Val Ala Thr Leu Asn
225                 230                 235                 240

Ile Gly Ser Ser Gln Ser Arg Glu Ala Ala Gly Glu Glu Pro Glu Ser
                245                 250                 255

Gln Pro Ser Pro Ala Gln Ala Asn Ser Gly Lys Leu Pro Pro Trp Met
            260                 265                 270

Leu Arg Thr Ile Ser Asn Arg
        275

<210> SEQ ID NO 21
<211> LENGTH: 21
<212> TYPE: DNA
<213> ORGANISM: Artificial Sequence
<220> FEATURE:
<223> OTHER INFORMATION: Synthetic Primer

<400> SEQUENCE: 21
tcctggagcc acaacttcta g                                        21

<210> SEQ ID NO 22
<211> LENGTH: 19
<212> TYPE: DNA
<213> ORGANISM: Artificial Sequence
<220> FEATURE:
<223> OTHER INFORMATION: Synthetic Primer

<400> SEQUENCE: 22
ttccagcggg accagaacc                                           19

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
ggatcaagaa gcacttct                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic Primer

<400> SEQUENCE: 24
cagctcgcac ggtgcttc                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic Primer

<400> SEQUENCE: 25
gaaactgagc agaacaga                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic Primer

<400> SEQUENCE: 26
cttcatgatg agggatca                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer

<400> SEQUENCE: 27
aggtacgtac accagcat                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Primer

<400> SEQUENCE: 28
gagcagacga atggagca                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Primer

<400> SEQUENCE: 29
actgatggtg cggagcat                                                18

<210> SEQ ID NO 30
<211> LENGTH: 17
<212> TYPE: DNA
<213> ORGANISM: Artificial Sequence
<220> FEATURE:
<223> OTHER INFORMATION: Synthetic Primer

<400> SEQUENCE: 30
attaccctgc agtgcgt                                                 17

<210> SEQ ID NO 31
<211> LENGTH: 19
<212> TYPE: DNA
<213> ORGANISM: Artificial Sequence
<220> FEATURE:
<223> OTHER INFORMATION: Synthetic Primer

<400> SEQUENCE: 31
agtaccatag gtacatgga                                               19

<210> SEQ ID NO 32
<211> LENGTH: 19
<212> TYPE: DNA
<213> ORGANISM: Artificial Sequence
<220> FEATURE:
<223> OTHER INFORMATION: Synthetic Primer

<400> SEQUENCE: 32
atggcgggga agagggaga                                               19

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
tcactttgag ttgaaaagtg                                              20

<210> SEQ ID NO 34
<211> LENGTH: 18
<212> TYPE: DNA
<213> ORGANISM: Artificial Sequence
<220> FEATURE:
<223> OTHER INFORMATION: Synthetic Primer

<400> SEQUENCE: 34
caatgacgac ggttctga                                                18

<210> SEQ ID NO 35
<211> LENGTH: 18
<212> TYPE: DNA
<213> ORGANISM: Artificial Sequence
<220> FEATURE:
<223> OTHER INFORMATION: Synthetic Primer

<400> SEQUENCE: 35
gcagacttaa cgatgaca                                                18

<210> SEQ ID NO 36
<211> LENGTH: 17

```
<212> TYPE: DNA
<213> ORGANISM: Artificial Sequence
<220> FEATURE:
<223> OTHER INFORMATION: Synthetic Primer

<400> SEQUENCE: 36
caggactgga gaggtgg                                                    17

<210> SEQ ID NO 37
<211> LENGTH: 18
<212> TYPE: DNA
<213> ORGANISM: Artificial Sequence
<220> FEATURE:
<223> OTHER INFORMATION: Synthetic Primer

<400> SEQUENCE: 37
ttcactcgtt gtcgtacc                                                   18

<210> SEQ ID NO 38
<211> LENGTH: 18
<212> TYPE: DNA
<213> ORGANISM: Artificial Sequence
<220> FEATURE:
<223> OTHER INFORMATION: Synthetic Primer

<400> SEQUENCE: 38
gagaagatga cccaratc                                                   18

<210> SEQ ID NO 39
<211> LENGTH: 19
<212> TYPE: DNA
<213> ORGANISM: Artificial Sequence
<220> FEATURE:
<223> OTHER INFORMATION: Synthetic Primer

<400> SEQUENCE: 39
cacttcatga tggagttgt                                                  19

<210> SEQ ID NO 40
<211> LENGTH: 19
<212> TYPE: DNA
<213> ORGANISM: Artificial Sequence
<220> FEATURE:
<223> OTHER INFORMATION: Synthetic Primer

<400> SEQUENCE: 40
gactggcatg aacttcggt                                                  19

<210> SEQ ID NO 41
<211> LENGTH: 20
<212> TYPE: DNA
<213> ORGANISM: Artificial Sequence
<220> FEATURE:
<223> OTHER INFORMATION: Synthetic Primer

<400> SEQUENCE: 41
caatttctgg gcaggaagtc                                                 20

<210> SEQ ID NO 42
<211> LENGTH: 18
<212> TYPE: DNA
<213> ORGANISM: Artificial Sequence
<220> FEATURE:
<223> OTHER INFORMATION: Synthetic Primer

<400> SEQUENCE: 42
catcgcaaga ccggcaac                                                   18
```

<210> SEQ ID NO 43
<211> LENGTH: 25
<212> TYPE: DNA
<213> ORGANISM: Artificial Sequence
<220> FEATURE:
<223> OTHER INFORMATION: Synthetic Primer

<400> SEQUENCE: 43
caccgtggag cctcttattg ttggt                                         25

<210> SEQ ID NO 44
<211> LENGTH: 22
<212> TYPE: DNA
<213> ORGANISM: Artificial Sequence
<220> FEATURE:
<223> OTHER INFORMATION: Synthetic Primer

<400> SEQUENCE: 44
tagatacaac tgctgatggg ta                                            22

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer

<400> SEQUENCE: 45 tagggggttta gatgcaactg t                                            21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
tatctgggaa ctactcacac a                                             21

<210> SEQ ID NO 47
<211> LENGTH: 20
<212> TYPE: DNA
<213> ORGANISM: Artificial Sequence
<220> FEATURE:
<223> OTHER INFORMATION: Synthetic Primer

<400> SEQUENCE: 47
tatttatttg cttggtactg                                               20

<210> SEQ ID NO 48
<211> LENGTH: 18
<212> TYPE: DNA
<213> ORGANISM: Artificial Sequence
<220> FEATURE:
<223> OTHER INFORMATION: Synthetic Primer

<400> SEQUENCE: 48 ctcccccca aatgaagc                                                  18

<210> SEQ ID NO 49
<211> LENGTH: 22
<212> TYPE: DNA
<213> ORGANISM: Artificial Sequence
<220> FEATURE:
<223> OTHER INFORMATION: Synthetic Primer

```
<400> SEQUENCE: 49
gaccttattc acattggtta tg                                              22

<210> SEQ ID NO 50
<211> LENGTH: 26
<212> TYPE: DNA
<213> ORGANISM: Artificial Sequence
<220> FEATURE:
<223> OTHER INFORMATION: Synthetic Primer

<400> SEQUENCE: 50
sarhtgaagm ggatagagaa caagat                                          26

<210> SEQ ID NO 51
<211> LENGTH: 20
<212> TYPE: DNA
<213> ORGANISM: Artificial Sequence
<220> FEATURE:
<223> OTHER INFORMATION: Synthetic Primer

<400> SEQUENCE: 51
ctcgtagagc ttgcccttgg                                                 20

<210> SEQ ID NO 52
<211> LENGTH: 21
<212> TYPE: DNA
<213> ORGANISM: Artificial Sequence
<220> FEATURE:
<223> OTHER INFORMATION: Synthetic Primer

<400> SEQUENCE: 52
tcgagaacaa gatcaaccgc c                                               21

<210> SEQ ID NO 53
<211> LENGTH: 21
<212> TYPE: DNA
<213> ORGANISM: Artificial Sequence
<220> FEATURE:
<223> OTHER INFORMATION: Synthetic Primer

<400> SEQUENCE: 53
tggtggagaa gttgatgagc c                                               21

<210> SEQ ID NO 54
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: N=C or G
<220> FEATURE:
<221> NAME/KEY: misc_feature
<222> LOCATION: (15)..(15)
<223> OTHER INFORMATION: N=C or G or T

<400> SEQUENCE: 54
ttggagaagg tnacncggct                                                 20

<210> SEQ ID NO 55
<211> LENGTH: 17
<212> TYPE: DNA
<213> ORGANISM: Artificial Sequence
<220> FEATURE:
<223> OTHER INFORMATION: Synthetic Primer
```

```
<220> FEATURE:
<221> NAME/KEY: misc_feature
<222> LOCATION: (7)..(7)
<223> OTHER INFORMATION: N=A or G or T
<220> FEATURE:
<221> NAME/KEY: misc_feature
<222> LOCATION: (10)..(10)
<223> OTHER INFORMATION: N=C or T
<220> FEATURE:
<221> NAME/KEY: misc_feature
<222> LOCATION: (16)..(16)
<223> OTHER INFORMATION: N=G or C

<400> SEQUENCE: 55
gttctcnatn cgcttna                                                17

<210> SEQ ID NO 56
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(5)
<223> OTHER INFORMATION: N=A or G or C
<220> FEATURE:
<221> NAME/KEY: misc_feature
<222> LOCATION: (8)..(8)
<223> OTHER INFORMATION: N=AG
<220> FEATURE:
<221> NAME/KEY: misc_feature
<222> LOCATION: (11)..(11)
<223> OTHER INFORMATION: N=G or C

<400> SEQUENCE: 56
gccgncangt naccttcttc caa                                         23

<210> SEQ ID NO 57
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: N=G or C or T
<220> FEATURE:
<221> NAME/KEY: misc_feature
<222> LOCATION: (6)..(6)
<223> OTHER INFORMATION: N= C or T
<220> FEATURE:
<221> NAME/KEY: misc_feature
<222> LOCATION: (7)..(7)
<223> OTHER INFORMATION: N= A or C
<220> FEATURE:
<221> NAME/KEY: misc_feature
<222> LOCATION: (13)..(13)
<223> OTHER INFORMATION: N= G or T

<400> SEQUENCE: 57
gcnctnntcg tcntctc                                                17

<210> SEQ ID NO 58
<211> LENGTH: 23
<212> TYPE: DNA
<213> ORGANISM: Artificial Sequence
<220> FEATURE:
<223> OTHER INFORMATION: Synthetic Primer

<400> SEQUENCE: 58
accgcagcca ccatctcacc tca                                         23
```

<210> SEQ ID NO 59
<211> LENGTH: 21
<212> TYPE: DNA
<213> ORGANISM: Artificial Sequence
<220> FEATURE:
<223> OTHER INFORMATION: Synthetic Primer

<400> SEQUENCE: 59
cctctcgcca ccaccaccag a                                                    21

<210> SEQ ID NO 60
<211> LENGTH: 22
<212> TYPE: DNA
<213> ORGANISM: Artificial Sequence
<220> FEATURE:
<223> OTHER INFORMATION: Synthetic Primer

<400> SEQUENCE: 60
tgctcctgat tggtccacag tt                                                   22

<210> SEQ ID NO 61
<211> LENGTH: 26
<212> TYPE: DNA
<213> ORGANISM: Artificial Sequence
<220> FEATURE:
<223> OTHER INFORMATION: Synthetic Primer

<400> SEQUENCE: 61
gagttgtcgt aaccagcagc atcact                                               26

<210> SEQ ID NO 62
<211> LENGTH: 27
<212> TYPE: DNA
<213> ORGANISM: Artificial Sequence
<220> FEATURE:
<223> OTHER INFORMATION: Synthetic Primer

<400> SEQUENCE: 62
aacatcacgt catgcagcca caaggat                                              27

<210> SEQ ID NO 63
<211> LENGTH: 26
<212> TYPE: DNA
<213> ORGANISM: Artificial Sequence
<220> FEATURE:
<223> OTHER INFORMATION: Synthetic Primer

<400> SEQUENCE: 63
atgggaccat tccagtcagt ctagct                                               26

<210> SEQ ID NO 64
<211> LENGTH: 45
<212> TYPE: DNA
<213> ORGANISM: Artificial Sequence
<220> FEATURE:
<223> OTHER INFORMATION: Synthetic Primer

<400> SEQUENCE: 64
ctaatacgac tcactatagg gcaagcagtg gtatcaacgc agagt                          45

<210> SEQ ID NO 65
<211> LENGTH: 24
<212> TYPE: DNA
<213> ORGANISM: Artificial Sequence
<220> FEATURE:
<223> OTHER INFORMATION: Synthetic Primer

```
<400> SEQUENCE: 65
ctacgagagc ccaargccaa mcat                                          24

<210> SEQ ID NO 66
<211> LENGTH: 25
<212> TYPE: DNA
<213> ORGANISM: Artificial Sequence
<220> FEATURE:
<223> OTHER INFORMATION: Synthetic Primer

<400> SEQUENCE: 66
agcaacacat ccttgtgaag gccca                                         25

<210> SEQ ID NO 67
<211> LENGTH: 24
<212> TYPE: DNA
<213> ORGANISM: Artificial Sequence
<220> FEATURE:
<223> OTHER INFORMATION: Synthetic Primer

<400> SEQUENCE: 67
agctaagtac cgtgtgatgc ggct                                          24

<210> SEQ ID NO 68
<211> LENGTH: 21
<212> TYPE: DNA
<213> ORGANISM: Artificial Sequence
<220> FEATURE:
<223> OTHER INFORMATION: Synthetic Primer

<400> SEQUENCE: 68
tggcggcgac gggctttccg a                                             21

<210> SEQ ID NO 69
<211> LENGTH: 19
<212> TYPE: DNA
<213> ORGANISM: Artificial Sequence
<220> FEATURE:
<223> OTHER INFORMATION: Synthetic Primer

<400> SEQUENCE: 69
gggagcgagt gtgtggtac                                                19

<210> SEQ ID NO 70
<211> LENGTH: 17
<212> TYPE: DNA
<213> ORGANISM: Artificial Sequence
<220> FEATURE:
<223> OTHER INFORMATION: Synthetic Primer

<400> SEQUENCE: 70
accctggcct ccctgtc                                                  17

<210> SEQ ID NO 71
<211> LENGTH: 22
<212> TYPE: DNA
<213> ORGANISM: Artificial Sequence
<220> FEATURE:
<223> OTHER INFORMATION: Synthetic Primer

<400> SEQUENCE: 71
atggtctgtg tggtgcaagc ca                                            22

<210> SEQ ID NO 72
<211> LENGTH: 22
```

<212> TYPE: DNA
<213> ORGANISM: Artificial Sequence
<220> FEATURE:
<223> OTHER INFORMATION: Synthetic Primer

<400> SEQUENCE: 72
accgatctac ctgaactgct tg                                              22

<210> SEQ ID NO 73
<211> LENGTH: 21
<212> TYPE: DNA
<213> ORGANISM: Artificial Sequence
<220> FEATURE:
<223> OTHER INFORMATION: Synthetic Primer

<400> SEQUENCE: 73
tatctgggaa ctactcacac a                                               21

<210> SEQ ID NO 74
<211> LENGTH: 414
<212> TYPE: DNA
<213> ORGANISM: Aspergillus nidulans

<400> SEQUENCE: 74
ctgctgattg tcgatagttg tgatagttcc cacttgtccg tccgcatcgg catccgcagc     60
tcsggatagt tccgacctag gattggatgc atgcggaacc gcacgagggc ggggcggaaa    120
ttgacacacc actcctctcc acgcaccgtt caagaggtac gcgtatagag ccgtatagag    180
cagagacgga gcactttctg gtactgtccg cacgggatgt ccgcacggag agccacaawc    240
gagcggggcc ccgtaacaag atatcttgtt tgaagataga aaataacaag atatcttgtc    300
gtgctctcct accccaggat cgcatccccg catagctgaa catctatata aagaccccca    360
aggttctcag tctcaccaac atcatcaacc aacaatcaac agttctctga gctc          414

<210> SEQ ID NO 75
<211> LENGTH: 20
<212> TYPE: DNA
<213> ORGANISM: Artificial Sequence
<220> FEATURE:
<223> OTHER INFORMATION: Synthetic Primer

<400> SEQUENCE: 75
agcatcaaca gatgatagct                                                 20

<210> SEQ ID NO 76
<211> LENGTH: 19
<212> TYPE: DNA
<213> ORGANISM: Artificial Sequence
<220> FEATURE:
<223> OTHER INFORMATION: Synthetic Primer

<400> SEQUENCE: 76
tgatacagca ccagcacga                                                  19

<210> SEQ ID NO 77
<211> LENGTH: 19
<212> TYPE: DNA
<213> ORGANISM: Artificial Sequence
<220> FEATURE:
<223> OTHER INFORMATION: Synthetic Primer

<400> SEQUENCE: 77
tcgtgctggt gctgtatca                                                  19

```
<210> SEQ ID NO 78
<211> LENGTH: 20
<212> TYPE: DNA
<213> ORGANISM: Artificial Sequence
<220> FEATURE:
<223> OTHER INFORMATION: Synthetic Primer

<400> SEQUENCE: 78
aaggtgggag acatcatcga                                              20

<210> SEQ ID NO 79
<211> LENGTH: 24
<212> TYPE: DNA
<213> ORGANISM: Artificial Sequence
<220> FEATURE:
<223> OTHER INFORMATION: Synthetic peptide

<400> SEQUENCE: 79
gcggatccgg tgtcatgaat atag                                         24

<210> SEQ ID NO 80
<211> LENGTH: 24
<212> TYPE: DNA
<213> ORGANISM: Artificial Sequence
<220> FEATURE:
<223> OTHER INFORMATION: Synthetic peptide

<400> SEQUENCE: 80
gcgtcgacca gtgacctctc cttc                                         24
```